United States Patent [19]

Comb et al.

[11] Patent Number: 5,352,778

[45] Date of Patent: * Oct. 4, 1994

[54] RECOMBINANT THERMOSTABLE DNA POLYMERASE FROM ARCHAEBACTERIA

[75] Inventors: Donald G. Comb, Beverly; Francine Perler, Brookline; Rebecca Kucera, Beverly; William E. Jack, Wenham, all of Mass.

[73] Assignee: New England Biolabs, Inc., Beverly, Mass.

[ * ] Notice: The portion of the term of this patent subsequent to Jun. 21, 2011 has been disclaimed.

[21] Appl. No.: 167,238

[22] Filed: Dec. 15, 1993

Related U.S. Application Data

[63] Continuation of Ser. No. 117,491, Sep. 7, 1993, which is a continuation of Ser. No. 811,421, Dec. 18, 1991, abandoned, which is a continuation-in-part of Ser. No. 686,340, Apr. 17, 1991, which is a continuation-in-part of Ser. No. 626,057, Dec. 11, 1990, abandoned, which is a continuation-in-part of Ser. No. 513,994, Apr. 26, 1990, Pat. No. 5,210,036.

[51] Int. Cl.$^5$ .................. C12N 9/10; C12N 15/11; C12N 15/54; C12N 15/00
[52] U.S. Cl. .................. 536/23.2; 435/69.1; 435/252.3; 435/252.33; 435/320.1; 536/23.7; 536/24.32; 935/10; 935/14; 935/22; 935/66
[58] Field of Search ............ 435/69.1, 194, 252.3, 435/252.33, 320.1; 536/23.2, 24.32

[56] References Cited

U.S. PATENT DOCUMENTS

| | | | |
|---|---|---|---|
| 4,652,639 | 3/1987 | Stabinsky | 435/91.52 |
| 4,683,195 | 7/1987 | Mullis | 435/6 |
| 4,683,202 | 7/1987 | Mullis | 435/91.2 |
| 4,800,159 | 1/1989 | Mullis et al. | 435/91.2 |
| 4,889,818 | 12/1989 | Gelfand et al. | 435/194 |
| 4,935,361 | 6/1990 | Lin et al. | 435/172.3 |
| 4,946,786 | 8/1990 | Tabor et al. | 435/194 |
| 4,952,496 | 8/1990 | Studier et al. | 435/91.41 |
| 5,001,050 | 3/1991 | Blanco et al. | 435/5 |
| 5,002,875 | 3/1991 | Lacks et al. | 435/69.1 |
| 5,047,342 | 9/1991 | Chatterjee | 435/194 |
| 5,079,352 | 1/0792 | Gelfand et al. | 536/23.2 |
| 5,210,036 | 5/1993 | Comb et al. | 435/194 |

FOREIGN PATENT DOCUMENTS

| | | |
|---|---|---|
| 0258017 | 3/1988 | European Pat. Off. . |
| 455430A3 | 11/1991 | European Pat. Off. . |
| 92/09689 | 6/1993 | PCT Int'l Appl. . |

OTHER PUBLICATIONS

Hamel, *European Journal of Biochemistry*, 190:517–521 (1990).
Klimczak, et al., *Nucleic Acids Research*, 13(14):5269–5282 (1985).
Salhi, et al., *Biochemical and Biophysical Research Communications*, 167(3):1341–1347 (1990).
Salhi, et al., *Journal of Molecular Biology*, 209:635–644 (1989).
Klimczak, et al. *Biochemistry*, 25:4850–4855 (1986).
Belkin, et al., *Arch. Microbiology*, 141:181–186 (1985).
Kjems, et al., *Canadian Journal of Microbiology*, 35(1):210–214 (1989).
Wich, et al. *The EMBO Journal* 6(2):523–528 (1987).
Kuhsel, et al., *Science*, 250:1570–1573 (1990).

(List continued on next page.)

*Primary Examiner*—Robert A. Wax
*Assistant Examiner*—William W. Moore
*Attorney, Agent, or Firm*—David G. Conlin; David S. Resnick

[57] ABSTRACT

Recombinant DNA polymeraset from archaebacteria as well as isolated DNA coding for such polymeraset are provided. The isolated DNA is obtained by use of DNA or antibody probet prepared from the DNA encoding *T. litoralis* DNA polymerate and the *T. litoralis* DNA polymerate respectively. Also provided are meshocs for producing recombinant archaebacteria thermostable DNA polymerase and methods for enhancing the expression of such polymeraset by identifying, locating and removing introns from within the DNA coding for such DNA polymerases.

12 Claims, 25 Drawing Sheets

OTHER PUBLICATIONS

Xu, M., et al., *Science,* 250:1566–1570 (1990).
Belfort, et al., *Cell,* 64(1):9–11 (1991).
Kjems, et al., *Cell,* 54(3):693–703 (1988).
Mattila, *Nucleic Acids Research,* 19(18):4967–4973 (1991).
Bessman, et al., *J. Bio. Chem.,* 233:171–177 (1957).
Buttin and Kornberg, *J. Biol. Chem.,* 241:5419–5427 (1966).
Brutlag, and Kornberg, *J. Biol. Chem.,* 247:241–248 (1972).
Chang, et al., *J. Biol. Chem.,* 252:1873–1880 (1977).
Chien, et al., *J. Bacteriol.,* 127:1550–1557 (1976).
Kaledin, et al., *Biokhymiya* 45:644–651 (1980) (Russian Text) English Translation—*Biochem.,* 45(4):494–401.
Saiki, et al., *Science,* 239:487–491 (1988).
Brock, et al., *Science,* 230:132–138 (1985).
Bernstein, H., *J. Bacteriology,* 171(5):2265–2270 (1989).
Goodrich-Blair, *Cell,* 63(2):417–422 (1990).
Lundberg, et al., *Gene,* 108(1):1–6 (1991).
Rüttimann, et al., *Eur. J. Biochem.,* 149:41–46 (1985).
Elie, et al., *J. Biochem.* 178:619–626 (1989).
Bechtereva, et al., *Nucleic Acid Res.,* 17(24):10507 (1989).
Lawyer, et al., *J. Biol. Chem.,* 264(11):6427–6437 (1989).
Bernard, et al., *Cell,* 59:219–228 (1989).
Neuner, et al., *Arch. Microbiol.,* 153:205–207 (1990).
Perlman, et al., *Science,* 246:1106–1109 (1989).
Mathur, et al., *Nucleic Acids Res.,* 19(24):6952 (1991).
Lehman, et al., *J. Biol. Chem.,* 233:163 (1958).
Wang, et al., *FASEB Journal,* 3:14–21 (1989).
Rossi, et al., *System Appl. Microbiol.,* 7:337–341 (1986).
Stetter, et al., *Journal of Chemical Technology and Biotechnology* 42:315–317 (1988).
Lundberg, et al., Derwent Abstract, Abstract No. 91-07714 (1991).
Tang, et al., Abstract Annual Meeting—Am. Soc. Microbiol. (90 Meet., p. 214) 1990.
Mathur, et al., Derwent Abstract, Abstract No. 92-02293 (1992).
Fiala, et al., *Archives of Microbiology,* 145(1):56–61 (1986).
Lundberg, et al., *The FASEB Journal,* 5(6):Abstract, Part III, p. A1549, Abstract No. 6841 (1991).
Bryant, et al., *The Journal of Biological Chemistry,* 264(9):5070–5079 (1989).
Tabor, et al., *The Journal of Biological Chemistry,* 264(11):6447–6458 (1989).
Jung, et al., *Biochemical and Biophysical Research Communications,* 170(3):1294–1300 (1990).
Matsuda, et al., *FEBS Letters,* 126(1):111–113 (1981).
Hewick, et al., *The Journal of Biological Chemistry,* 256(15):7990–7997 (1981).
Xu, et al., *Analytical Biochemistry,* 170(1):19–30 (1988).
Stetter, et al., *FEMS Microbiology Reviews,* 75(1):117–124 (1990).
Mathur, et al., *The Journal of Cell Biology,* 115(3):80A, Abstract No. 463 (1991).
Advertisement, *Science,* 254(26) "Take the *Pyrococcus* Challenge" (1991).
Zillig, et al., *Systematic and Applied Microbiology,* 9(1–2):62–70 (1987).

SIZE DETERMINATION OF T. litoralis DNA POLYMERASE FUNCTIONS

THERMAL STABILITIES OF DNA POLYMERASES

RESPONSE OF DNA POLYMERASES TO THE PRESENCE OR ABSENSE OF DEOXYNUCLEOTIDES

ORGANIZATION OF THE *T. litoralis* DNA POLYMERASE GENE IN NATIVE DNA AND CLONE NEB671 AND NEB687

BOLD LINES REPRESENT *T. litoralis* DNA PRESENT IN EXPRESSION CLONE NEB671 AND CLONE NEB687

DASHED LINES REPRESENT CLONING JUNCTION SITES

HATCHED BOX REPRESENTS DELETED INTRON

```
GAATTCGCGA TAAAATCTAT TTTCTTCCTC CATTTTTCAA TTTCAAAAAC GTAAGCATGA      60

GCCAAACCTC TCGCCCTTTC TCTGTCCTTC CCGCTAACCC TCTTGAAAAC TCTCTCCAAA     120

GCATTTTTTG ATGAAAGCTC ACGCTCCTCT ATGAGGGTCA GTATATCTGC AATGAGTTCG     180

TGAAGGGTTA TTCTGTAGAA CAACTCCATG ATTTTCGATT TGGATGGGGG TTTAAAATT     240

TGGCGGAACT TTTATTTAAT TTGAACTCCA GTTTATATCT GGTGGTATTT ATGATACTGG     300

ACACTGATTA CATAACAAAA GATGGCAAGC CTATAATCCG AATTTTTAAG AAAGAGAACG     360

GGGAGTTTAA AATAGAACTT GACCCTCATT TTCAGCCCTA TATATATGCT CTTCTCAAAG     420

ATGACTCCGC TATTGAGGAG ATAAAGGCAA TAAAGGGCGA GAGACATGGA AAAACTGTGA     480

GAGTGCTCGA TGCAGTGAAA GTCAGGAAAA AATTTTTGGG AAGGAAGTT GAAGTCTGGA     540

AGCTCATTTT CGAGCATCCC CAAGACGTTC CAGCTATGCG GGCAAAATA AGGGAACATC     600

CAGCTGTGGT TGACATTTAC GAATATGACA TACCCTTTGC CAAGCGTTAT CTCATAGACA     660

AGGGCTTGAT TCCCATGGAG GGAGACGAGG AGCTTAAGCT CCTTGCCTTT GATATTGAAA     720

CGTTTTATCA TGAGGGAGAT GAATTTGGAA AGGGCGAGAT AATAATGATT AGTTATGCCG     780

ATGAAGAAGA GGCCAGAGTA ATCACATGGA AAAATATCGA TTTGCCGTAT GTCGATGTTG     840

TGTCCAATGA AAGAGAAATG ATAAAGCGTT TTGTTCAAGT TGTTAAAGAA AAAGACCCCG     900

ATGTGATAAT AACTTACAAT GGGGACAATT TTGATTTGCC GTATCTCATA AAACGGGCAG     960

AAAAGCTGGG AGTTCGGCTT GTCTTAGGAA GGGACAAAGA ACATCCCGAA CCCAAGATTC    1020

AGAGGATGGG TGATAGTTTT GCTGTGGAAA TCAAGGGTAG AATCCACTTT GATCTTTTCC    1080
```

FIG. 6-1

```
CAGTTGTGCG AAGGACGATA AACCTCCCAA CGTATACGCT TGAGGCAGTT TATGAAGCAG    1140

TTTTAGGAAA AACCAAAAGC AAATTAGGAG CAGAGGAAAT TGCCGCTATA TGGGAAACAG    1200

AAGAAAGCAT GAAAAAACTA GCCAGTACT CAATGGAAGA TGCTAGGGCA ACGTATGAGC     1260

TCGGGAAGGA ATTCTTCCCC ATGGAAGCTG AGCTGGCAAA GCTGATAGGT CAAAGTGTAT    1320

GGGACGTCTC GAGATCAAGC ACCGGCAACC TCGTGGAGTG GTATCTTTTA AGGGTGGCAT    1380

ACGCGAGGAA TGAACTTGCA CCGAACAAAC CTGATGAGGA AGAGTATAAA CGGCGCTTAA    1440

GAACAACTTA CCTGGGAGGA TATGTAAAAG AGCCAGAAAA AGGTTTGTGG GAAAATATCA    1500

TTTATTTGGA TTTCCGCAGT CTGTACCCTT CAATAATAGT TACTCACAAC GTATCCCCAG    1560

ATACCCTTGA AAAAGAGGGC TGTAAGAATT ACGATGTTGC TCCGATAGTA GGATATAGGT    1620

TCTGCAAGGA CTTTCCGGGC TTTATTCCCT CCATACTCGG GGACTTAATT GCAATGAGGC    1680

AAGATATAAA GAAGAAAATG AAATCCACAA TTGACCCGAT CGAAAAGAAA ATGCTCGATT    1740

ATAGGCAAAG GCTATTAAA TTGCTTGCAA ACAGCATCTT ACCAACGAG TGGTTACCAA      1800

TAATTGAAAA TGGAGAAATA AAATTCGTGA AAATTGGCGA GTTTATAAAC TCTTACATGG    1860

AAAAACAGAA GGAAAACGTT AAAACAGTAG AGAATACTGA AGTTCTCGAA GTAAACAACC    1920

TTTTTGCATT CTCATTCAAC AAAAAAATCA AAGAAAGTGA AGTCAAAAAA GTCAAAGCCC    1980

TCATAAGACA TAAGTATAAA GGGAAAGCTT ATGAGATTCA GCTTAGCTCT GGTAGAAAAA    2040

TTAACATAAC TGCTGGCCAT AGTCTGTTTA CAGTTAGAAA TGGAGAAATA AAGGAAGTTT    2100

CTGGAGATGG GATAAAAGAA GGTGACCTTA TTGTAGCACC AAAGAAAATT AAACTCAATG    2160

AAAAAGGGGT AAGCATAAAC ATTCCCGAGT TAATCTCAGA TCTTTCCGAG GAAGAAACAG    2220

CCGACATTGT GATGACGATT TCAGCCAAGG GCAGAAAGAA CTTCTTTAAA GGAATGCTGA    2280
```

FIG. 6-2

```
GAACTTTAAG GTGGATGTTT GGAGAAGAAA ATAGAAGGAT AAGAACATTT AATCGCTATT    2340

TGTTCCATCT CGAAAAACTA GGCCTTATCA AACTACTGCC CCGCGGATAT GAAGTTACTG    2400

ACTGGGAGAG ATTAAAGAAA TATAAACAAC TTTACGAGAA GCTTGCTGGA AGCGTTAAGT    2460

ACAACGGAAA CAAGAGAGAG TATTTAGTAA TGTTCAACGA GATCAAGGAT TTTATATCTT    2520

ACTTCCCACA AAAAGAGCTC GAAGAATGGA AAATTGGAAC TCTCAATGGC TTTAGAACGA    2580

ATTGTATTCT CAAAGTCGAT GAGGATTTTG GGAAGCTCCT AGGTTACTAT GTTAGTGAGG    2640

GCTATGCAGG TGCACAAAAA AATAAAACTG GTGGTATCAG TTATTCGGTG AAGCTTTACA    2700

ATGAGGACCC TAATGTTCTT GAGAGCATGA AAAATGTTGC AGAAAAATTC TTTGGCAAGG    2760

TTAGAGTTGA CAGAAATTGC GTAAGTATAT CAAAGAAGAT GGCATACTTA GTTATGAAAT    2820

GCCTCTGTGG AGCATTAGCC GAAAACAAGA GAATTCCTTC TGTTATACTC ACCTCTCCCG    2880

AACCGGTACG GTGGTCATTT TTAGAGGCGT ATTTTACAGG CGATGGAGAT ATACATCCAT    2940

CAAAAAGGTT TAGGCTCTCA ACAAAAAGCG AGCTCCTTGC AAATCAGCTT GTGTTCTTGC    3000

TGAACTCTTT GGGAATATCC TCTGTAAAGA TAGGCTTTGA CAGTGGGGTC TATAGAGTGT    3060

ATATAAATGA AGACCTGCAA TTTCCACAAA CGTCTAGGGA GAAAAACACA TACTACTCTA    3120

ACTTAATTCC CAAAGAGATC CTTAGGGACG TGTTTGGAAA AGAGTTCCAA AAGAACATGA    3180

CGTTCAAGAA ATTTAAAGAG CTTGTTGACT CTGGAAAACT TAACAGGGAG AAAGCCAAGC    3240

TCTTGGAGTT CTTCATTAAT GGAGATATTG TCCTTGACAG AGTCAAAAGT GTTAAAGAAA    3300

AGGACTATGA AGGGTATGTC TATGACCTAA GCGTTGAGGA TAACGAGAAC TTTCTTGTTG    3360

GTTTTGGTTT GCTCTATGCT CACAACAGCT ATTACGGCTA TATGGGGTAT CCTAAGGCAA    3420

GATGGTACTC GAAGGAATGT GCTGAAAGCG TTACCGCATG GGGGAGACAC TACATAGAGA    3480
```

FIG. 6-3

| | | | | | | |
|---|---|---|---|---|---|---|
| TGACGATAAG | AGAAATAGAG | GAAAAGTTCG | GCTTTAAGGT | TCTTTATGCG | GACAGTGTCT | 3540 |
| CAGGAGAAAG | TGAGATCATA | ATAAGGCAAA | ACGGAAAGAT | TAGATTTGTG | AAAATAAAGG | 3600 |
| ATCTTTTCTC | TAAGGTGGAC | TACAGCATTG | GCGAAAAAGA | ATACTGCATT | CTCGAAGGTG | 3660 |
| TTGAAGCACT | AACTCTGGAC | GATGACGGAA | AGCTTGTCTG | GAAGCCCGTC | CCCTACGTGA | 3720 |
| TGAGGCACAG | AGCGAATAAA | AGAATGTTCC | GCATCTGGCT | GACCAACAGC | TGGTATATAG | 3780 |
| ATGTTACTGA | GGATCATTCT | CTCATAGGCT | ATCTAAACAC | GTCAAAAACG | AAACTGCCA | 3840 |
| AAAAAATCGG | GGAAAGACTA | AAGGAAGTAA | AGCCTTTTGA | ATTAGGCAAA | GCAGTAAAAT | 3900 |
| CGCTCATATG | CCCAAATGCA | CCGTTAAAGG | ATGAGAATAC | CAAACTAGC | GAAATAGCAG | 3960 |
| TAAAATTCTG | GGAGCTCGTA | GGATTGATTG | TAGGAGATGG | AAACTGGGT | GGAGATTCTC | 4020 |
| GTTGGGCAGA | GTATTATCTT | GGACTTTCAA | CAGGCAAAGA | TGCAGAAGAG | ATAAAGCAAA | 4080 |
| AACTTCTGGA | ACCCCTAAAA | ACTTATGGAG | TAATCTCAAA | CTATTACCCA | AAAAACGAGA | 4140 |
| AAGGGGACTT | CAACATCTTG | GCAAAGAGCC | TTGTAAAGTT | TATGAAAAGG | CACTTTAAGG | 4200 |
| ACGAAAAAGG | AAGACGAAAA | ATTCCAGAGT | TCATGTATGA | GCTTCCGGTT | ACTTACATAG | 4260 |
| AGGCATTTCT | ACGAGGACTG | TTTTCAGCTG | ATGGTACTGT | AACTATCAGG | AAGGGAGTTC | 4320 |
| CAGAGATCAG | GCTAACAAAC | ATTGATGCTG | ACTTTCTAAG | GGAAGTAAGG | AAGCTTCTGT | 4380 |
| GGATTGTTGG | AATTTCAAAT | TCAATATTTG | CTGAGACTAC | TCCAAATCGC | TACAATGGTG | 4440 |
| TTTCTACTGG | AACCTACTCA | AAGCATCTAA | GGATCAAAAA | TAAGTGGCGT | TTTGCTGAAA | 4500 |
| GGATAGGCTT | TTTAATCGAG | AGAAAGCAGA | AGAGACTTTT | AGAACATTTA | AAATCAGCGA | 4560 |
| GGGTAAAAAG | GAATACCATA | GATTTTGGCT | TTGATCTTGT | GCATGTGAAA | AAAGTCGAAG | 4620 |

FIG. 6-4

```
AGATACCATA CGAGGGTTAC GTTTATGACA TTGAAGTCGA AGAGACGCAT AGGTTCTTTG    4680
CAAACAACAT CCTGGTACAC AATACTGACG GCTTTTATGC CACAATACCC GGGGAAAAGC    4740
CTGAACTCAT TAAAAGAAA GCCAAGGAAT TCCTAAACTA CATAAACTCC AAACTTCCAG    4800
GTCTGCTTGA GCTTGAGTAT GAGGGCTTTT ACTTGAGAGG ATTCTTTGTT ACAAAAAGC    4860
GCTATGCAGT CATAGATGAA GAGGGCAGGA TAACAACAAG GGGCTTGGAA GTAGTAAGGA    4920
GAGATTGGAG TGAGATAGCT AAGGAGACTC AGGCAAAGGT TTTAGAGGCT ATACTTAAAG    4980
AGGGAAGTGT TGAAAAAGCT GTAGAAGTTG TTAGAGATGT TGTAGAGAAA ATAGCAAAAT    5040
ACAGGGTTCC ACTTGAAAAG CTTGTTATCC ATGAGCAGAT TACCAGGGAT TTAAAGGACT    5100
ACAAAGCCAT TGGCCCTCAT GTCGCGATAG CAAAAGACT TGCCGCAAGA GGGATAAAAG    5160
TGAAACGGG CACAATAATA AGCTATATCG TTCTCAAAGG GAGCGGAAAG ATAAGCGATA    5220
GGGTAATTTT ACTTACAGAA TACGATCCTA GAAACACAA GTACGATCCG GACTACTACA    5280
TAGAAAACCA AGTTTTGCCG GCAGTACTTA GGATACTCGA AGCGTTTGGA TACAGAAAGG    5340
AGGATTTAAG GTATCAAAGC TCAAAACAAA CCGGCTTAGA TGCATGGCTC AAGAGGTAGC    5400
TCTGTTGCTT TTTAGTCCAA GTTTCTCCGC GAGTCTCTCT ATCTCTCTTT TGTATTCTGC    5460
TATGTGGTTT TCATTCACTA TTAAGTAGTC CGCCAAAGCC ATAACGCTTC CAATTCCAAA    5520
CTTGAGCTCT TTCCAGTCTC TGGCCTCAAA TTCACTCCAT GTTTTTGGAT CGTCGCTTCT    5580
CCCTCTTCTG CTAAGCCTCT CGAATCTTTT TCTTGGCGAA GAGTGTACAG CTATGATGAT    5640
TATCTCTTCC TCTGGAAACG CATCTTTAAA CGTCTGAATT TCATCTAGAG ACCTCACTCC    5700
GTCGATTATA ACTGCCTTGT ACTTCTTTAG TAGTTCTTTT ACCTTTGGGA TCGTTAATTT    5760
TGCCACGGCA TTGTCCCCAA GCTCCTGCCT AAGCTGAATG CTCACACTGT TCATACCTTC    5820
GGGAGTTCTT GGGATCC                                                    5837
```

FIG. 6-5

```
Region III:        ASP --- --- GLN --- ALA --- LYS --- --- --- ASN SER --- TYR GLY --- --- GLY 11aa ALA --- --- --- THR --- --- GLY ARG Left Junction:     ASP TYR ARG GLN ARG ALA ILE LYS LEU LEU ALA nt 1721  CGAAAGAAA ATGCTCGATT ATAGGCAAAG GCTATTAAA TTGCTTGCAA ACAGCATCTT ACCC....

nt 3375                                           ...TATGCTCACA ACAGCTATTA CGGCTATATG GGGTATCCTAA...

5'  CGAAAAGAAA ATGCTCGATT ATAGGCAAAG GCTATTAAA TTGCTAGCAA ACAGCTATTA CGGCTATATG GGGTACCC 3'

3'  TAGCTTTCTTT TACGAGCTAA TATCCGTTTC CGATAATTT AACGATCGTT TGTCGATAAT GCCGATATAC CCCATGGATT 5'

FIG. 12

```
GGATCCCTCTCTTTTTGGTAACCCCATACGTCATTCCCTCAACCAAAACT
TCAGCATCGTTGCAGTGGTCAGTGTGTCTGTGGGAGATGAAGAGGACGTC
GATTTTCTGGGGTCTATCTTGTATCTCCACATTCTAACTAACGCTCCAG
GCCCAGGATCAACGTAGATGTTTTGCTCGCCTTAATGAAGAAGCCACCA
GTGGCTCTTGCCTGCGTTATCGTGACGAACCTTCCACCACCGCCACCGAG
AAAAGTTATCTCTATCATCTCACACCTCCCCATAACATCACCTGCTCAA
TTTTTAAGCGTTCTTAAAGGCTTAAATACGTGAATTTAGCGTAAATTATT
GAGGGATTAAGTATGATACTTGACGCTGACTACATCACCGAGGATGGGAA
GCCGATTATAAGGATTTTCAAGAAAGAAACGGCGAGTTTAAGGTTGAGT
ACGACAGAAACTTTAGACCTTACATTTACGCTCTCCTCAAAGATGACTCG
CAGATTGATGAGGTTAGGAAGATAACCGCCGAGAGGCATGGGAAGATAGT
GAGAATTATAGATGCCGAAAGGTAAGGAAGAAGTTCCTGGGGAGGCCGA
TTGAGGTATGGAGGCTGTACTTTGAACACCCTCAGGACGTTCCGCAATA
AGGGATAAGATAAGAGCATTCGCAGTTATTGACATCTTTGAGTACGA
CATTCCGTTCGCGAAGAGGTACCTAATAGACAAGGCCTAATTCCAATGG
AAGGCGATGAAGAGCTCAAGTTGCTCGCATTTGACATAGAAACCCTCTAT
CACGAAGGGGAGGAGTTCGCGAAGGGGCCCATTATAATGATAAGCTATGC
TGATGAGGAAGAAGCCAAAGTCATAACGTGGAAAAGATCGATCTCCCGT
ACGTCGAGGTAGTTTCCAGCGAGAGGGAGATGATAAAGCGGTTCCTCAAG
GTGATAAGGGAGAAAGATCCCGATGTTATAATTACCTACAACGGCGATTC
TTTCGACCTTCCCTATCTAGTTAAGAGGGCCGAAAAGCTCGGGATAAAGC
TACCCCTGGGAAGGGACGGTAGTGAGCCAAAGATGCAGAGGCTTGGGGAT
ATGACAGCGGTGGAGATAAAGGGAAGGATACACTTTGACCTCTACCACGT
GATTAGGAGAACGATAAACCTCCCAACATACACCCTCGAGGCAGTTTATG
AGGCAATCTTCGGAAAGCCAAAGGAGAAAGTTTACGCTCACGAGATAGCT
GAGGCCTGGGAGACTGGAAAGGGACTGGAGAGAGTTGCAAAGTATTCAAT
GGAGGATGCAAAGGTAACGTACGAGCTCGGTAGGGAGTTCTTCCCAATGG
AGGCCCAGCTTTCAAGGTTAGTCGGCCAGCCCCTGTGGGATGTTTCTAGG
TCTTCAACTGGCAACTTGGTGGAGTGGTACCTCCTCAGGAAGGCCTACGA
GAGGAATGAATTGGCTCCAAACAAGCCGGATGAGAGGGAGTACGAGAGAA
GGCTAAGGGAGAGCTACGCTGGGGGATACGTTAAGGAGCCGGAGAAAGGG
CTCTGGGAGGGGTTAGTTTCCCTAGATTTCAGGAGCCTGTACCCCTCGAT
AATAATCACCCATAACGTCTCACCGGATACGCTGAACAGGGAAGGGTGTA
GGGAATACGATGTCGCCCCAGAGGTTGGGCACAAGTTCTGCAAGGACTTC
CCGGGGTTTATCCCCAGCCTGCTCAAGAGGTTATTGGATGAAAGGCAAGA
AATAAAAGGAAGATGAAAGCTTCTAAAGACCCAATCGAGAAGAAGATGC
TTGATTACAGGCAACGGGCAATCAAAATCCTGGCAAACAGCATTTTACCG
GAAGAATGGGTTCCACTAATTAAAAACGGTAAAGTTAAGATATTCCGCAT
TGGGGACTTCGTTGATGGACTTATGAAGGCGAACCAAGGAAAAGTGAAGA
AAACGGGGGATACAGAAGTTTTAGAAGTTGCAGGAATTCATGCGTTTTCC
TTTGACAGGAAGTCCAAGAAGGCCCGTGTAATGGCAGTGAAAGCCGTGAT
AAGACACCGTTATTCCGGAAATGTTTATAGAATAGTCTTAAACTCTGGTA
GAAAAATAACAATAACAGAAGGGCATAGCCTATTTGTCTATAGGAACGGG
GATCTCGTTGAGGCAACTGGGGAGGATGTCAAAATTGGGGATCTTCTTGC
AGTTCCAAGATCAGTAAACCTACCAGAGAAAGGGAACGCTTGAATATTG
TTGAACTTCTTCTGAATCTCTCACCGGAAGAGACAGAAGATATAATACTT
ACGATTCCAGTTAAAGGCAGAAAGAACTTCTTCAAGGGAATGTTGAGAAC
```

FIG. 18-1

```
ATTACGTTGGATTTTTGGTGAGGAAAAGAGAGTAAGGACAGCGAGCCGCT
ATCTAAGACACCTTGAAAATCTCGGATACATAAGGTTGAGGAAAATTGGA
TACGACATCATTGATAAGGAGGGGCTTGAGAAATATAGAACGTTGTACGA
GAAACTTGTTGATGTTGTCCGCTATAATGGCAACAAGAGAGAGTATTTAG
TTGAATTTAATGCTGTCCGGGACGTTATCTCACTAATGCCAGAGGAAGAA
CTGAAGGAATGGCGTATTGGAACTAGAAATGGATTCAGAATGGGTACGTT
CGTAGATATTGATGAAGATTTTGCCAAGCTTCTTGGCTACTATGTGAGCG
AGGGAAGTGCGAGGAAGTGGAAGAATCAAACTGGAGGTTGGAGTTACACT
GTGAGATTGTACAACGAGAACGATGAAGTTCTTGACGACATGGAACACTT
AGCCAAGAAGTTTTTGGGAAAGTCAAACGTGGAAAGAACTATGTTGAGA
TACCAAAGAAAATGGCTTATATCATCTTTGAGAGCCTTTGTGGACTTTG
GCAGAAAACAAAGGGTTCCTGAGGTAATCTTTACCTCATCAAAGGGCGT
TAGATGGGCCTTCCTTGAGGGTTATTTCATCGGCGATGGCGATGTTCACC
CAAGCAAGAGGGTTCGCCATCAACGAAGAGCGAGCTTTTAGTAAATGGC
CTTGTTCTCCTACTTAACTCCCTTGGAGTATCTGCCATTAAGCTTGGATA
CGATAGCGGAGTCTACAGGGTTTATGTAAACGAGGAACTTAAGTTTACGG
AATACAGAAGAAAAGAATGTATATCACTCTCACATTGTTCCAAGGAT
ATTCTCAAAGAAACTTTTGGTAAGGTCTTCCAGAAAAATATAAGTTACAA
GAAATTTAGAGAGCTTGTAGAAATGGAAACTTGACAGGGAGAAAGCCA
AACGCATTGAGTGGTTACTTAACGGAGATATAGTCCTAGATAGAGTCGTA
GAGATTAAGAGAGAGTACTATGATGGTTACGTTTACGATCTAAGTGTCGA
TGAAGATGAGAATTTCCTTG
```

FIG. 18-2

```
  1 MILDADYITEDGKPIIRIFKKENGEFKVEYDRNFRPYIYALLKDDSQIDE  50
    ||||.||||.||||||||||||||||||:|.|.:|.||||||||||.|:|
  1 MILDTDYITKDGKPIIRIFKKENGEFKIELDPHFQPYIYALLKDDSAIEE  50

51 VRKITAERHGKIVRIIDAEKVRKKFLGRPIEVWRLYFEHPQDVPAIRDKI 100
    ::  |.:||||.||::||  ||||||||.:|||:|.||||||||:|:||
 51 IKAIKGERHGKTVRVLDAVKVRKKFLGREVEVWKLIFEHPQDVPAMRGKI 100

101 REHSAVIDIFEYDIPFAKRYLIDKGLIPMEGDEELKLLAFDIETLYHEGE 150
    |||.||:||:|||||||||||||||||||||||||||||||||||:||||:
101 REHPAVVDIYEYDIPFAKRYLIDKGLIPMEGDEELKLLAFDIETFYHEGD 150

151 EFAKGPIIMISYADEEEAKVITWKKIDLPYVEVVSSEREMIKRFLKVIRE 200
    ||:||.||||||||||:|||||.||||||:|||.||||||||:.|::|
151 EFGKGEIIMISYADEEEARVITWKNIDLPYVDVVSNEREMIKRFVQVVKE 200

201 KDPDVIITYNGDSFDLPYLVKRAEKLGIKLPLGRDG..SEPKMQRLGDMT 248
    ||||||||||||.||||||:||||||:|.||||    .|||:||:||
201 KDPDVIITYNGDNFDLPYLIKRAEKLGVRLVLGRDKEHPEPKIQRMGDSF 250

249 AVEIKGRIHFDLYHVIRRTINLPTYTLEAVYEAIFGKPKEKVYAHEIAEA 298
    ||||||||||:.|:|||||||||||||||||::||.|.|: |.|||.
251 AVEIKGRIHFDLFPVVRRTINLPTYTLEAVYEAVLGKTKSKLGAEEIAAI 300

299 WETGKGLERVAKYSMEDAKVTYELGREFFPMEAQLSRLVGQPLWDVSRSS 348
    |||:.::.::|.||||||:.|||||:||||||:||||..:|:||..:|||||||
301 WETEESMKKLAQYSMEDARATYELGKEFFPMEAELAKLIGQSVWDVSRSS 350

349 TGNLVEWYLLRKAYERNELAPNKPDEREYERRLRESYAGGYVKEPEKGLW 398
    ||||||||||  ||.|||||||||||  ||.||||..|  |||||||||
351 TGNLVEWYLLRVAYARNELAPNKPDEEEYKRRLRTTYLGGYVKEPEKGLW 400

399 EGLVSLDFRSLYPSIIITHNVSPDTLNREGCREYDVAPEVGHKFCKDFPG 448
    |.::  |||||||||||:||||||||::|||:::|||||  ||.:|||||||
401 ENIIYLDFRSLYPSIIVTHNVSPDTLEKEGCKNYDVAPIVGYRFCKDFPG 450

449 FIPSLLKRLLDERQEIKRKMKASKDPIEKKMLDYRQRAIKILANSILPEE 498
    ||||:|  |:.  ||:||:|||..  ||||||||||||||||:|||||||:|
451 FIPSILGDLIAMRQDIKKKMKSTIDPIEKKMLDYRQRAIKLLANSILPNE 500

499 WVPLIKNGKVKIFRIGDFVDGLMKANQGKVKKTGDTEVLEVAGIHAFSFD 548
    |:|:|.||.:|:..:|:|:::.|. ...:||..::||||||..: ||||:
501 WLPIIENGEIKFVKIGEFINSYMEKQKENVKTVENTEVLEVNNLFAFSFN 550
```

FIG. 19-1

```
549 RKSKKARVMAVKAVIRHRYSGNVYRIVLNSGRKITITEGHSLFVYRNGDL 598
    :|  |..  |.  |||:|||:|.|..|  |  |.|||||.||.|||||.  |||::
551 KKIKESEVKKVKALIRHKYKGKAYEIQLSSGRKINITAGHSLFTVRNGEI 600

599 VEATGEDVKIGDLLAVPRSVNLPEKRERLNIVELLLNLSPEETEDIILTI 648
    |..|:::|  |||:..|:.:.|  ||   .:||.||:  :||.|||.||::||
601 KEVSGDGIKEGDLIVAPKKIKLNEKGVSINIPELISDLSEEETADIVMTI 650

649 PVKGRKNFFKGMLRTLRWIFGEE.KRVRTASRYLRHLENLGYIRLRKIGY 697
    ..||||||||||||||||||:||| :|:||  .|||  |||.||.|:|  .  ||
651 SAKGRKNFFKGMLRTLRWMFGEENRRIRTFNRYLFHLEKLGLIKLLPRGY 700

698 DIIDKEGLEKYRTLYEKLVDVVRYNGNKREYLVEFNAVRDVISLMPEEEL 747
    ::.|.|  |.||:  |||||.:  |:|||||||||  ||.::|.||.:|:.||
701 EVTDWERLKKYKQLYEKLAGSVKYNGNKREYLVMFNEIKDFISYFPQKEL 750

748 KEWRIGTRNGFRMGTFVDIDEDFAKLLGYYVSEGSARKWKNQTGGWSYTV 797
    .||:|||  ||||  ..::|||||:|||||||||||  |  ||.|||  ||.|
751 EEWKIGTLNGFRTNCILKVDEDFGKLLGYYVSEGYAGAQKNKTGGISYSV 800

798 RLYNENDEVLDDMEHLAKKFFGKVKRGKNYVEIPKKMAYIIFESLCGTLA 847
    :||||:..||:.|.::|.||||||:  ::|:|.|.||||||:::.:|||.||
801 KLYNEDPNVLESMKNVAEKFFGKVRVDRNCVSISKKMAYLVMKCLCGALA 850

848 ENKRVPEVIFTSSKGVRWAFLEGYFIGDGDVHPSKRVRLSTKSELLVNGL 897
    ||||:|.||:||...|||.|||:||.||||:|||||.||||||||||.|.|
851 ENKRIPSVILTSPEPVRWSFLEAYFTGDGDIHPSKRFRLSTKSELLANQL 900

898 VLLLNSLGVSAIKLGYDSGVYRVYVNEELKFTEYRKKKNVYHSHIVPKDI 947
    |:|||||:.:|:|:|||||||||:|:|.|.:  .:.||.|.|:::||:|
901 VFLLNSLGISSVKIGFDSGVYRVYINEDLQFPQTSREKNTYYSNLIPKEI 950

948 LKETFGKVFQKNISYKKFRELVENGKLDREKAKRIEWLLNGDIVLDRVVE 997
    |::.|||  ||||:.:|||  |||:.|||  ||||||  :|:::||||||||||  .
951 LRDVFGKEFQKNMTFKKFKELVDSGKLNREKAKLLEFFINGDIVLDRVKS 1000

998  IKREYYDGYVYDLSVDEDENFL 1019
     :|  .  |:||||||||:::||||
1001 VKEKDYEGYVYDLSVEDNENFL 1022
```

FIG. 19-2.

RECOMBINANT THERMOSTABLE DNA POLYMERASE FROM ARCHAEBACTERIA

"This is a continuation of copending application(s) Ser. No. 08/117,491 filed on Sep. 7, 1993 which is a Continuation of 07/811,421 filed on Dec. 18, 1991 now abandoned, which is a Continuation-In-Part of 07/686,340 filed Apr. 17, 1991 which is a Continuation-In-Part of 07/626,057 filed Dec. 11, 1990 (now abandoned), which is a Continuation-In-Part of 07/513,994 filed on Apr. 26, 1990 (now Pat. No. 5,210,036).

FIELD OF THE INVENTION

The present invention relates to recombinant DNA polymerases from archaebacterium, to isolated DNA coding for said DNA polymerases which hybridizes to DNA probes prepared from the DNA sequence coding for *T. litoralis* DNA polymerase, to DNA and antibody probes employed in the isolation of said DNA, as well as to related methods for isolating said DNA and methods of identifying, locating and removing intervening nucleotide sequences within said DNA in order to enhance expression of said DNA polymerases

BACKGROUND OF THE INVENTION

DNA polymerases are a family of enzymes involved in DNA repair and replication. Extensive research has been conducted on the isolation of DNA polymerases from mesophilic microorganisms such as *E. coli*. See, for example, Bessman, et al., *J. Biol. Chem.* (1957) 233:171–177 and Buttin and Kornberg *J. Biol. Chem.* (1966) 241:5419–5427.

Examples of DNA polymerases isolated from *E. coli* include *E. coli* DNA polymerase I, Klenow fragment of *E. coli* DNA polymerase I and T4 DNA polymerase. These enzymes have a variety of uses in recombinant DNA technology including, for example, labelling of DNA by nick translation, second-strand cDNA synthesis in cDNA cloning, and DNA sequencing. See Maniatis, et al., *Molecular Cloning: A Laboratory Manual* (1982).

Recently, U.S. Pat. Nos. 4,683,195, 4,683,202 and 4,800,159 disclosed the use of the above enzymes in a process for amplifying, detecting, and/or cloning nucleic acid sequences. This process, commonly referred to as polymerase chain reaction (PCR), involves the use of a polymerase, primers and nucleotide triphosphates to amplify existing nucleic acid sequences.

Some of the DNA polymerases discussed above possess a 3'–5' exonuclease activity which provides a proofreading function that gives DNA replication much higher fidelity than it would have if synthesis were the result of only a one base-pairing selection step. Brutlag, D. and Kornberg, A., *J. Biol. Chem.*, (1972) 247:241–248. DNA polymerases with 3'–5' proofreading exonuclease activity have a substantially lower base incorporation error rate when compared with a non-proofreading exonuclease-possessing polymerase. Chang, L.M.S., *J. Biol. Chem.*, (1977) 252:1873–1880.

Research has also been conducted on the isolation and purification of DNA polymerases from thermophiles, such as *Thermus aquaticus*. Chien, A., et al. *J. Bacteriol.* (1976) 127:1550–1557, discloses the isolation and purification of a DNA polymerase with a temperature optimum of 80° C. from *T. aquaticus* YT1 strain. The Chien, et al., purification procedure involves a four-step process. These steps involve preparation of crude extract, DEAE-Sephadex chromatography, phosphocellulose chromatography, and chromatography on DNA cellulose. Kaledin, et al., *Biokhymiyay* (1980) 45:644–651 also discloses the isolation and purification of a DNA polymerase from cells of *T. aquaticus* YT1 strain. The Kaledin, et al. purification procedure involves a six-step process. These steps involve isolation of crude extract, ammonium sulfate precipitation, DEAE-cellulose chromatography, fractionation on hydroxyapatite, fractionation on DEAE-cellulose, and chromatography on single-strand DNA-cellulose.

U.S. Pat. No. 4,889,818 discloses a purified thermostable DNA polymerase from *T. aquaticus*, Taq polymerase, having a molecular weight of about 86,000 to 90,000 daltons prepared by a process substantially identical to the process of Kaledin with the addition of the substitution of a phosphocellulose chromatography step in lieu of chromatography on single-strand DNA-cellulose. In addition, European Patent Application 0258017 discloses Taq polymerase as the preferred enzyme for use in the PCR process discussed above. Research has indicated that while the Taq DNA polymerase has a 5'–3' polymerase-dependent exonuclease function, the Taq DNA polymerase does not possess a 3'–5' proofreading exonuclease function. Lawyer, F.C., et al. *J. Biol. Chem.*, (1989) 264:11, p. 6427–6437. Bernard, A., et al. Cell (1989) 59:219. As a result, Taq DNA polymerase is prone to base incorporation errors, making its use in certain applications undesirable. For example, attempting to clone an amplified gene is problematic since any one copy of the gene may contain an error due to a random misincorporation event. Depending on where in the replication cycle that error occurs (e.g., in an early replication cycle), the entire DNA amplified could contain the erroneously incorporated base, thus, giving rise to a mutated gene product. Furthermore, research has indicated that Taq DNA polymerase has a thermal stability of not more than several minutes at; 100° C.

Accordingly, other DNA polymerases with comparable or improved thermal stability and/or 3' to 5' exonuclease proofreading activity would be desirable for the scientific community. One such enzyme (described in more detail below), DNA polymerase from *Thermococcus litoralis*, an archaebacterium that grows at temperatures close to 100° C. near submarine thermal vents, has been cloned into *E. coli*. The production of large amounts of this recombinant enzyme protein from this gene is complicated, however, by the presence of two introns, one of which must be removed by genetic engineering techniques, and the other which encodes an endonuclease which is spliced out in *E. coli*.

It would be desirable to obtain and produce other highly thermostable DNA polymerases from archaebacterium which have a 3' to 5' proofreading activity and/or comparable or improved thermal stability so as to improve the DNA polymerase processes described above.

SUMMARY OF THE INVENTION

In accordance with the present invention, there is provided methods and products for identifying, isolating and cloning DNA which encodes DNA polymerases from archaebacteria. The present invention also relates to recombinant DNA polymerases from archaebacteria as well as to methods of improving expression of said recombinant DNA polymerases by identifying, locating and removing intervening nucleotide sequences or introns which occur within the DNA coding for said polymerases.

More specifically, in accordance with the present invention, it has been discovered that DNA coding for DNA polymerases from archaebacterium have substantial homology both at the DNA and amino acid level. It has also been discovered that the DNA from archaebacterium coding for such enzymes appear to have one or more intervening nucleotides or introns which also share substantially homology at the DNA level.

Thus, in accordance with the present invention, DNA probes can be constructed from the DNA sequence coding for one DNA polymerase from archaebacterium, such as *Thermococcus litoralis*, and used to identify and isolate DNA coding for DNA polymerases from other Archaebacterium such as *Pyrococcus*. Similarly, antibody probes which are cross-reactive with *T. litoralis* DNA polymerase can also be used to identify DNA coding coding sequences which express such other DNA polymerases.

Once the DNA coding for the target DNA polymerase has been isolated, it can be used to construct expression vectors in order to produce commercial quantitatives of the target DNA polymerase. In this regard, the present invention also provides methods of increasing expression levels of the target DNA polymerase by identifying, locating and removing any intervening nucleotide sequences or introns which occur in the DNA sequence coding for the DNA polymerase. As discussed below, while certain introns are spliced out in *E. coli.*, expression of the recombinant DNA polymerase can be enhanced by removal of such intervening nucleotide sequences prior to expression in *E. coli.*

BRIEF DESCRIPTION OF THE DRAWINGS

FIG. 6 is a partial nucleotide sequence of the 14 kb BamHI restriction fragment of bacteriophage NEB619 inclusive of the 1.3 kb, 1.6 kb and 1.9 kb Eco RI fragments and part of the Eco RI/BamHI fragment.

FIG. 7 is a comparison of the amino acids in the DNA polymerase consensus homology region III with the amino acids of the *T. litoralis* homology island III.

FIG. 12 is a nucleotide sequence of the primers used in Example III.

FIG. 16A is an autoradiograph of a Southern blot in which the 5' coding region of the *T. litoralis* DNA polymerase gene, bp 1-1274 was used as a hybridization probe.

FIG. 16B is an autoradiograph of a Southern blot in which the 3' coding region of *T. litoralis* DNA polymerase gene, bp 4718-5437 was used as a hybridization probe.

FIG. 16C-1 and FIG. 16C-2 are autoradiographs of a Southern blot in which bp 3666-4242 of IVS2 was used as a hybridization probe; the lower panel, FIG. 16C-2, represents a longer exposure of the same blot.

FIG. 16D-1 and FIG. 16D-2 are radioautographs of a Southern blot in which bp 2448-2882 of IVS1 was used as a hybridization probe; the lower panel, FIG. 16D-2, represents a longer exposure.

FIG. 18-1 and FIG. 18-2 collectively depict a partial DNA nucleotide sequence of the gene coding for the *Pyrococcus sp.* DNA polymerase.

FIG. 19-1 and FIG. 19-2 collectively depict is a comparison of the deduced amino acid sequence of *Pyrococcus sp.* DNA polymerase to *T. litoralis* DNA polymerase.

Figure 1A:
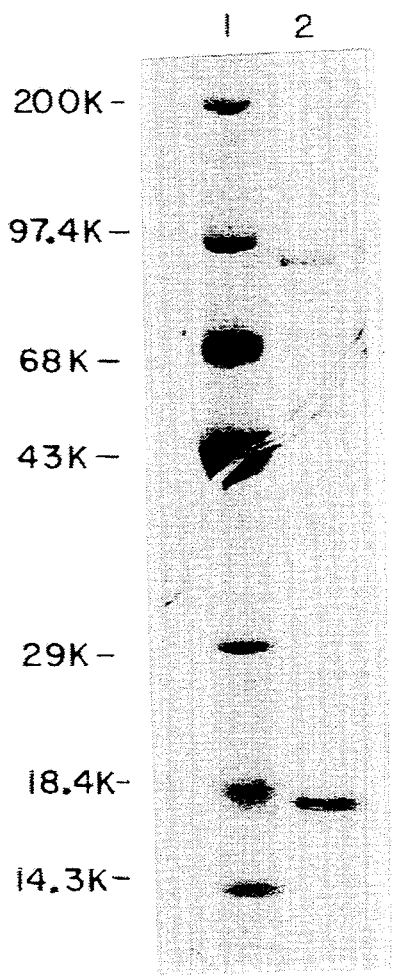
FIG. 1A is a photograph of the SDS-polyacrylamide gel of example 1.
Figure 1B:
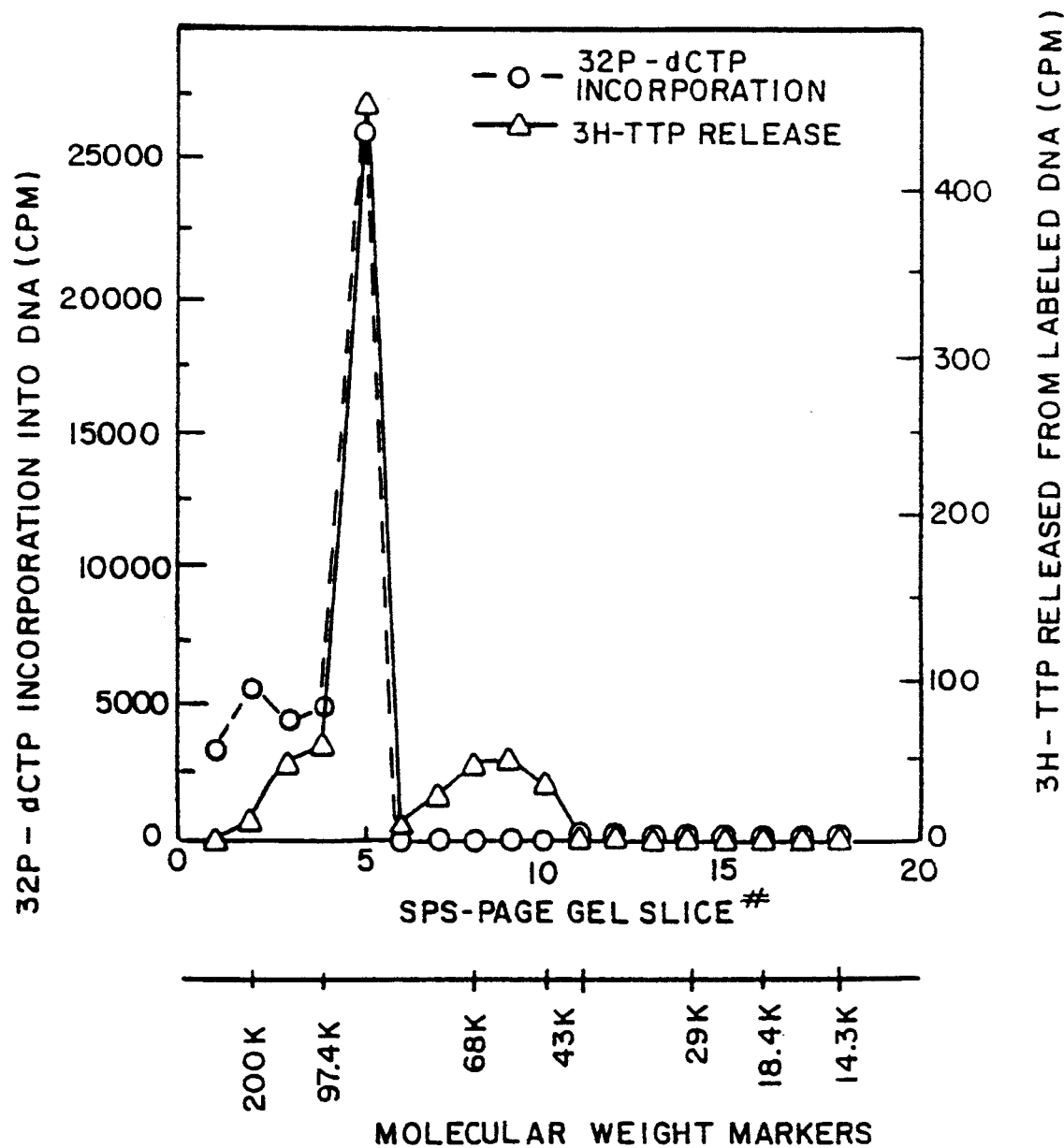
FIG. 1B is a graph showing the polymerase activity and exonuclease activity of the proteins eluted from lane 2 of the gel in FIG. 1A.
Figure 2:
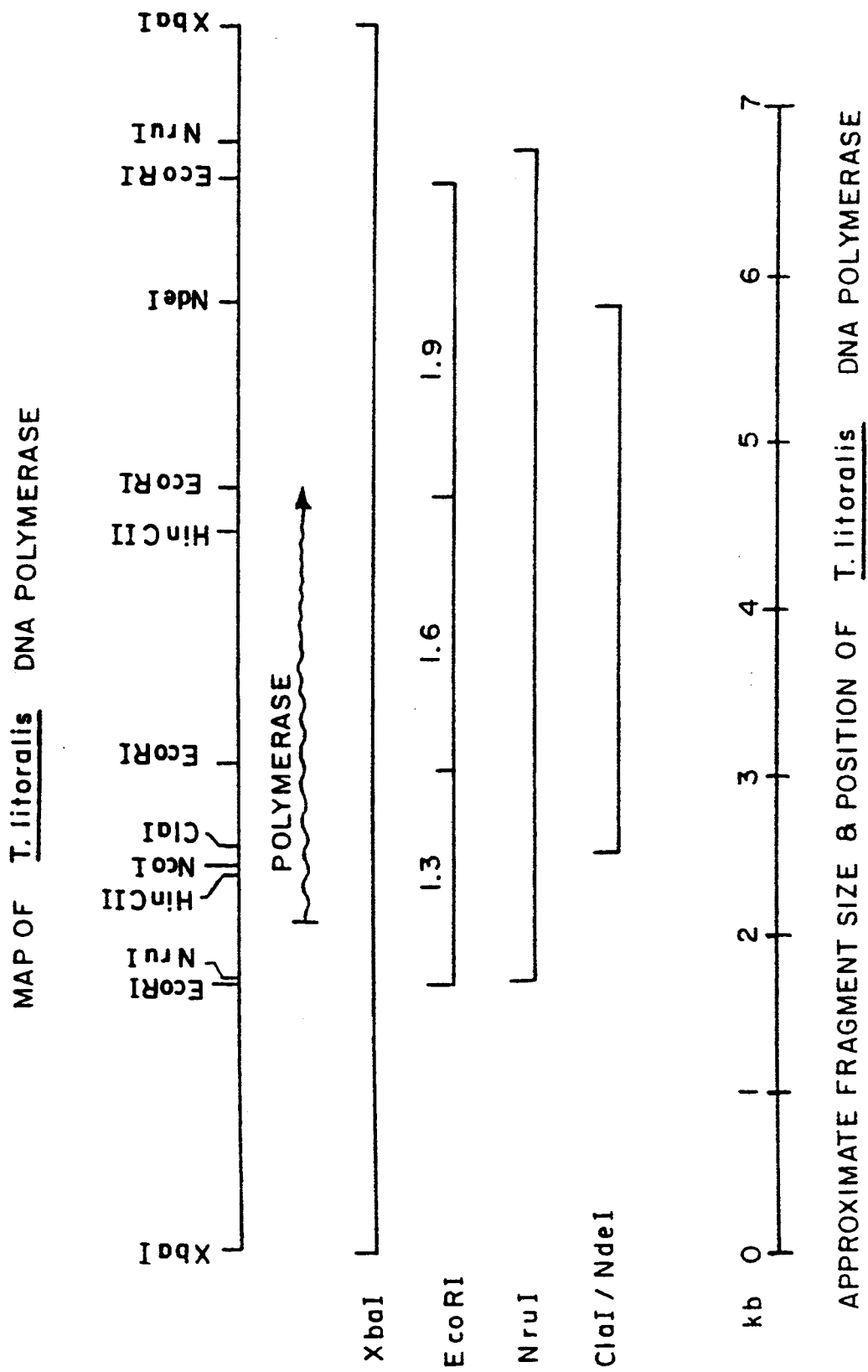
FIG. 2 is a restriction site map of the Xba fragment containing the gene encoding the *T. litoralis* DNA Polymerase which is entirely contained within the BamHI fragment of bacteriophage NEB 619.

The deduced amino acid sequences of the *Pyrococcus* DNA polymerase and *thermococcus litoralis* DNA polymerase are set froth on the top and bottom lines, respectively. Parent similarity was 83.219 and percent identify was 68.302.

DETAILED DESCRIPTION OF THE INVENTION

In accordance with one preferred embodiment of the present invention, there is provided a method of producing recombinant DNA polymerase from archaebacterium. The preferred process comprises 1) forming a genomic library from the target archaebacterium, 2) transforming or transfecting an appropriate host cell, 3) either i) reacting the DNA from the transformed or transfected host cells with a DNA probe which hybridizes to the DNA coding for the DNA polymerase from *T. litoratis,* or ii) reacting the extract from the transformed or transfected host cells with an antibody probe which is cross-reactive with *T. litoralis* DNA polymerase, 4) assaying the transformed or transfected cells of step 3 which either hybridize to the DNA probe or cross react with the *T. litoralis* specific antibody for thermostable DNA polymerase activity.

The aforementioned method allows for the production of recombinant DNA polymerases from archaebacterium, as well as for the isolation of DNA coding for said polymerases.

In accordance with another preferred embodiment, there is provided a method for enhancing the expression of recombinant DNA polymerases from archaebacterium. As noted above, it is believed that the DNA coding for DNA polymerases from archaebacterium may possess one or more introns which may complicate expression of the target recombinant DNA polymerase. Location and removal of these introns prior to constructing the expression system has been found to enhance expression of the target DNA polymerase, even when the intron is normally spliced out in its host cell. As discussed in more detail below, the intron can be identified and removed in a number of ways. In particular, it has also been found that the introns of *T. litoralis* share substantial homology at the DNA level with other genuses of archaebacteria such as *Pyrococcus.* Knowledge of this fact should facilitate the identification, location and removal of introns by the methods described in more detail below.

In practicing certain embodiments of the present invention it is preferable to employ either i) DNA probes which hybridize to the DNA coding for *T. litoralis* DNA polymerase, or ii) antibodies which cross-react with *T. litoralis* DNA polymerase. DNA probes are preferably constructed based on the DNA sequence coding for the *T. litoralis* DNA polymerase (See FIG. 6), while the antibody probes are preferably made from the purified *T. litoralis* enzyme itself. Following the procedures of the present invention, one could, of course construct probes based on the DNA polymerase or its DNA from other sources of archaebacterium. However, the preferred DNA polymerase and DNA used to construct such probes is from *T. litoralis.*

Production Of Native *T. litoralis* DNA Polymerase

*T. litoralis* DNA polymerase is obtainable from *T. litoralis* strain NS-C (DSM No. 5473, a sample of which has also been deposited at the American Type Culture Collection on Sep. 17, 1991 under ATCC Accession No. 55233). *T. litoralis* was isolated from a submarine thermal vent near Naples, Italy in 1985. This organism, *T. litoralis,* is an extremely thermophilic, sulfur metabolizing, archaebacteria, with a growth range between 55° C. and 98° C. Neuner, et al., *Arch. Microbiol.* (1990) 153:205–207.

For recovering the native protein, *T. litoralis* may be grown using any suitable technique, such as the technique described by Belkin, et al., *Arch Microbiol.* (1985) I42:181–186, the disclosure of which is incorporated by reference. Briefly, the cells are grown in the media described above containing 10 mg/ml of sulfur and 0.01M cysteine in 15 ml screw cap tubes at 95° C. for 2 days. When larger amounts of cells are required, 1 liter screw cap bottles are used and after sterilization are inoculated with a fresh 10 ml culture and grown at 90°–95° C. for 2 days.

After cell growth, one preferred method for isolation and purification of the enzyme is accomplished using the multi-step process as follows:

First, the cells, if frozen, are thawed, suspended in a suitable buffer such as buffer A (10 mM $KPO_4$ buffer, pH 7.4; 1.0 mM EDTA, 1.0 mM beta-mercaptoethanol), sonicated and centrifuged. The supernatant is then passed through a column which has a high affinity for proteins that bind to nucleic acids such as Affigel blue column (Biorad). The nucleic acids present in supernatant solution of *T. litoralis* and many of the proteins pass through the column and are thereby removed by washing the column with several column volumes of low salt buffer at pH of about 7.0. After washing, the enzyme is eluted with a linear gradient such as 0.1 to 2.0 M NaCl buffer A. The peak DNA polymerase activity is dialyzed and applied to a phosphocellulose column. The column is washed and the enzyme activity eluted with a linear gradient such as 0.1 to 1.0 M NaCl in buffer A. The peak DNA polymerase activity is dialyzed and applied to a DNA cellulose column. The column is washed and DNA polymerase activity is eluted with a linear gradient of 0.1 to 1.0 M NaCl in buffer A. The fractions containing DNA polymerase activity are pooled, dialyzed against buffer A, and applied to a high performance liquid chromatography column (HPLC) mono-Q column (anion exchanger). The enzyme is again eluted with a linear gradient such as 0.05 to 1.0 M NaCl in a buffer A. The fractions having thermostable polymerase activity are pooled, diluted and applied to HPLC mono-S column (cation exchanger). The enzyme is again eluted with a linear gradient such as 0.05 to 1.0 M NaCl in buffer A. The enzyme is about 50% pure at this stage. The enzyme may be further purified by precipitation of a contaminating lower molecular weight protein by repeated dialysis against buffer A supplemented with 50 mM NaCl.

The apparent molecular weight of the ONA polymerase obtainable from *T. litoralis* is between about 90,000 to 95,000 daltons when compared with protein standards of known molecular weight, such as phosphorylase B assigned a molecular weight of 97,400 daltons. It should be understood, however, that as a protein from an extreme thermophile, *T. litoralis* DNA polymerase may electrophorese at an aberrant relative molecular weight due to failure to completely denature or other intrinsic properties. The exact molecular weight of the thermostable enzyme of the present invention may be determined from the coding sequence of the *T. litoralis* DNA polymerase gene. The molecular weight of the eluted product may be determined by any technique, for example, by SDS-polyacrylamide gel electrophoresis (SDS-PAGE) using protein molecular weight markers.

Polymerase activity is preferably measured by the incorporation of radioactively labeled deoxynucleotides into DNAse-treated, or activated, DNA; following subsequent separation of the unincorporated deoxynucleotides from the DNA substrate, polymerase activity is proportional to the amount of radioactivity in the acid-insoluble fraction comprising the DNA. Lehman, I.R., et el., *J. Biol. Chem.* (1958) 233:163, the disclosure of which is incorporated herein by reference.

The half-life of the DNA polymerase of the present invention at 100° C. is about 60 minutes. The thermal stability or half-life of the DNA polymerase is determined by preincubating the enzyme at the temperature of interest in the presence of all assay components (buffer, $MgCl_2$, deoxynucleotides, and activated DNA) except the single radioactively-labeled deoxynucleotide. At predetermined time intervals, ranging from 4–180 minutes, small aliquots are removed, and assayed for polymerase activity using the method described above.

The half-life at 100° C. of the DNA polymerase can also be determined in the presence of stabilizers such as the nonionic detergent octoxynol, commonly known as TRITON X-100 (Rohm & Haas Co.), or the protein bovine serum albumin (BSA). The non-ionic detergents polyoxyethylated (20) sorbitan monolaurate (Tween 20, ICI Americas Inc.) and ethoxylated alkyl Phenol (nonyl) (ICONOL NP-40, BASF Wyandotte Corp.) can also be used. Stabilizers are used to prevent the small amount of enzyme added to the reaction mixture from adhering to the sides of the tube or from changing its structural conformation in some manner that decreases its enzymatic activity. The half-life at 100° C. of the DNA polymerase obtainable from *T. litoralis* in the presence of the stabilizer TRITON X-100 or BSA is about 95 minutes.

Preparation Of Recombinant *T. litoralis* DNA Polymerase

*T. litoralis* DNA polymerase may also be produced by recombinant DNA techniques, as the gene encoding this enzyme has been cloned from *T. litoralis* genomic DNA. The complete coding sequence for the *T. litoralis* DNA polymerase (FIG. 6) can be derived from bacteriophage NEB #619 on an approximately 14 kb BamHI restriction fragment. This phage was deposited with the American Type Culture Collection (ATCC) on Apr. 24, 1990 and has Accession No. ATCC 40795.

The production of a recombinant form of *T. litoralis* DNA polymerase generally includes the following steps: DNA is isolated which encodes the active form of the polymerase, either in its native form or as a fusion with other sequences which may or may not be cleaved away from the native form of the polymerase and which may or may not effect polymerase activity. Next, the gene is operably linked to appropriate control sequences for expression in either prokaryotic or eukaryotic host/vector systems. The vector preferably encodes all functions required for transformation and maintenance in a suitable host, and may encode selectable markers and/or control sequences for *T. litoralis* polymerase expression. Active recombinant thermostable polymerase can be produced by transformed host cultures either continuously or after induction of expression. Active thermostable polymerase can be recovered either from within host cells or from the culture media if the protein is secreted through the cell membrane.

While each of the above steps can be accomplished in a number of ways, it has been found that for cloning the DNA encoding *T. litoralis* DNA polymerase, expression of the polymerase from its own control sequences in *E. coli* results in instability of the polymerase gene, high frequency of mutation in the polymerase gene, slow cell growth, and some degree of cell mortality.

While not wishing to be bound by theory, it is believed that this instability is due at least in part to the presence of a 1614 bp intron that splits the *T. litoralis* DNA polymerase gene from nucleotides 1776 to 3389 of FIG. 6, and a second 1170 bp intron that splits the *T. litoralis* DNA polymerase gene from nucleotides 3534 to 4703. As discussed below, intervening sequences are also believed to be present in the DNA coding for DNA polymerases from other archaebacteria. Introns from a number of archaebacteria are also believed to share substantial homology to the introns present in the DNA for coding for *T. litoralis* DNA polymerase, which, in accordance with one aspect of the present invention, will facilitate their identification, location and removal.

Introns are stretches of intervening DNA which separate coding regions of a gene (the protein coding regions are called exons). Introns can contain nonsense sequences or can code for proteins. In order to make a functional protein, the intron must be spliced out of the pre-mRNA before translation of the mature mRNA into protein. Introns were originally identified in ·eukaryotes, but have been recently described in certain prokaryotes. (See, e.g., Krainer and Maniatis (*Transcription and Splicing* (1988) B.D. Hames and P.M. Glover, eds. IRL Press, Oxford and Washington, D.C. pp. 131–206)). When a gene with an intron is transcribed into mRNA the intron may self-splice out to form a mature mRNA or cellular factors may be required to remove the intron from the pre-mRNA. Id. Bacterial introns often require genus specific co-factors for splicing. For example, a *Bacillus* intron may not be spliced out in *E. coli*. (Id).

However, there is some evidence that suggests that the. intervening DNA sequence within the gene coding for the *T. litoralis* DNA polymerase is transcribed and translated, and that the peptide produced therefrom is spliced out at the protein level, not the mRNA level. Therefore, regardless of where the splicing event occurs, in order to express *T. litoralis* DNA polymerase in *E. coli*, it is preferable to delete the intervening sequence prior to expression of the polymerase in an *E. coli* system. Of course, the recombinant vector containing the *T. litoralis* DNA polymerase gene could be expressed in systems which possess the appropriate factors for splicing the intron, for example, a thermococcus system.

It is also preferable that the *T. litoralis* thermostable polymerase expression be tightly controlled in *E. coli* during cloning and expression. Vectors useful in practicing the present invention should provide varying degrees of controlled expression of *T. litoralis* polymerase by providing some or all of the following control features: (1) promoters or sites of initiation of transcription, either directly adjacent to the start of the polymerase or as fusion proteins, (2) operators which could be used to turn gene expression on or off, (3) ribosome binding sites for improved translation, and (4) transcription or translation termination sites for improved stability. Appropriate vectors used in cloning and expression of *T. litoralis* polymerase include, for example, phage and plasmids. Example of phage include λgt11 (Promega), λ Dash (Stratagene) λ ZapII (Stratagene).

Examples of plasmids include pBR322, pBluescript (Stratagene), pSP73 (Promega), pGW7 (ATCC No. ¢0166), pET3A (Rosenberg, et al., Gene, (1987) 56:125–135), and pET11C (*Methods in Enzymology* (1990) 185:60–89).

Transformation and Infection

Standard protocols exist for transformation, phage infection and cell culture. Maniatis, et al., *Molecular Cloning: A Laboratory Manual* (1982). Of the numerous *E. coli* strains which can be used for plasmid transformation, the preferred strains include JM101 (ATCC No. 33876), XL1 (Stratagene), and RRI (ATCC No. 31343), and BL21(DE3) plysS (*Methods in Enzomology* (1990) supra). *E. coli* strain XL1, ER1578 and ER1458 (Raleigh, et el., *N.A. Research* (1988) 16:1563–1575) are among the strains that can be used for lambda phage, and Y1089 can be used for lambda gtll lysogeny. When preparing transient lysogens in Y1089 (Arasu, et el., *Experimentel Parasitology* (1987) 64:281–289), a culture is infected with lambda gtll recombinant phage either by a single large dose of phage or by co-culturing with a lytic host. The infected Y1089 cells are preferably grown at 37° C. in the presence of the inducer IPTG resulting in buildup of recombinant protein within the lysis-defective host/phage system.

Construction of Genomic DNA Expression Library and Screening for Thermostable Polymerase The most common methods of screening for a gene of choice are (1) by hybridization to homologous genes from other organisms, (2) selection of activity by complementation of a host defect, (3) reactivity with specific antibodies, or (4) screening for enzyme activity. For *T. litoralis*, antibody detection is preferred since it initially only requires expression of a portion of the enzyme, not the complete active enzyme. The instability of the *T. litoralis* polymerase gene in *E. coli* would have made success by other methods more difficult.

*T. litoralis* DNA can be used to construct genomic libraries as either random fragments or restriction enzyme fragments. The latter approach is preferred. Preferably, Eco RI partials are prepared from *T. litoralis* genomic DNA using standard DNA restriction techniques such as described in Maniatis, et el., Molecular Cloning: A Laboratory Manual (1982), the disclosure of which is incorporated herein by reference. Other restriction enzymes such as BamHI, NruI and XbaI can also be used.

Although methods are available to screen both plasmids and phage using antibodies (Young and Davis, PNAS, (1983) 80:1194–1198), in accordance with the present invention it has been found that phage systems tend to work better and are therefore preferred for the first libraries. Since it is uncertain whether *T. litoralis* control regions function in *E. coli*, phage vectors which supply all necessary expression control regions such as lambda gt11 and lambda Zap II, are preferred. By cloning *T. litoralis* DNA into the Eco RI site of lambda gt11, *T. litoralis* polymerase may be expressed either as a fusion protein with beta-galactosidase or from its own endogenous promoter.

Once formed, the expression libraries are screened with mouse anti- *T. litoralis* DNA polymerase antiserum using standard antibody/plaque procedures such as those described by Young and Davis, PNAS (1983), supra.

The mouse anti-*T. litoralis* DNA polymerase antiserum used to screen the expression libraries can be prepared using standard techniques, such as the techniques described in Harlow and Cane, *Antibodies: A Laboratory Manual* (1988) CSH Press, the disclosure of which is incorporated herein by reference. Since most sere react with *E. coli* proteins, it is preferable that the *T. litoralis* polymerase antisera be preabsorbed by standard methods against *E. coli* proteins to reduce background reactivity when screening expression libraries. Phage reacting with anti-*T. litoralis* polymerase antiserum are picked and plaque purified. Young and Davis, PNAS (1983), supra.

The *T. litoralis* DNA polymerasa DNA, coding for part or the whole gene, can then be subcloned in, for example, pBR322, pBluescript, MI3 or pUC19. If desired, the DNA sequence can be determined by, for example, the Sanger dideoxy chain-terminating method (Sanger, F., Nicklen, S. & Coulson, A.R. PNAS (1977) 74:5463–5467).

Identification of DNA Encodino and Expression of the *T. litoralis* DNA Polymerase Several methods exist for determining that the DNA sequence coding for the *T. litoralis* Ils DNA polymerase has been obtained. These include, for example, comparing the actual or deduced amino-terminal sequence of the protein produced by the recombinant DNA to the native protein, or determining whether the recombinant DNA produces a protein which binds antibody specific for native *T. litoralis* DNA polymerase. In addition, research by Wang, et el., FASEB Journal (1989) 3:20 suggests that certain regions of DNA polymerase sequences are highly conserved among many species. As a result, by comparing the predicted amino acid sequence of the cloned gene product with the amino acid sequence of known DNA polymerases, such as human DNA polymerase and *E. coli* phage T4 DNA polymerase, the identification of these islands of homology provides strong evidence that the recombinant DNA indeed encodes a DNA polymerase. Once identified, the DNA sequence coding for the *T. litoralis* DNA polymerase, can be cloned into an appropriate expression vector such as a plasmid derived from *E. coli*, for example, pET3A, pBluescript or pUC19, the plasmids derived from the Becillus subtills such as pUB110, pTP5 and pC194, plasmids derived from yeast such as pSH19 and pSH15, bacteriophage such as lambda phage, bacteria such as *Agrobacterium tumefeciens*, animal viruses such as retroviruses and insect viruses such as Baculovirus.

As noted above, in accordance with the present invention, it has been found that DNA coding for *T. litoralis* DNA polymerase contains two introns: i) an 1614 bp intron or intervening sequence, spanning from nucleotides 1776 to 3389 in FIG. No. 6, and ii) an 1170 bp intron, spanning nucleotides 3534 to 4703 in FIG. 6. This 1170 bp intron codes for an endonuclease and is found to self-splice out in *E. coli*. Prior to overexpression in host cells such as *E. coli*, it is preferable to delete the DNA sequence coding for both the 1614 and 1170 bp introns. Even though the 1170 bp intron splices out in *E. coli.*, it has been found that expression vectors which do not contain this intron result in increased production of the desired polymerase.

In general, once an intron has been identified and located within a nucleotide sequence, there are a number of approaches known in the art which can be used to delete DNA sequences and therefore splice out an intron in-vitro. One method involves identifying unique restriction enzyme sites in the coding region which are near the splice junction or area to be deleted. A duplex oligomer is synthesized to bridge the gap between the two restriction fragments. A three-part ligation consisting of the amino end restriction fragment, the bridging oligo and the carboxy end restriction fragment yields an intact gene with the intron deleted.

Another method is a modification of the above-described method. The majority of the intron is deleted by cutting with restriction enzymes with unique sites within the intron, but close to the coding sequence border. The linear plasmid containing a deletion of the majority of the intron is ligated together. Single strand phage are generated from the pBluescript vector recombinant by super infection with the f1 helper phage IR1. A single strand oligomer is synthesized with the desired final sequence and is annealed to the partially deleted intron phage DNA. The remainder of the intron is thus looped out. By producing the original phage in E. coli strain CJ236 the Kunkel method of mutagenesis Methods in Enymology 154:367 (1987)) can be used to select for the full deleted intron constructs.

Yet another method which can be used to delete the intron uses DNA amplification. See, for example, Maniatis, et el., Molecular Cloning: A Laboratory Manual, (1989) Vol. 2, 2nd edition, the disclosure of which is herein incorporated by reference. Briefly, primers are generated to amplify and subsequently join the amino and carboxyl halves of the gene.

When an intron is deleted in-vitro, using the methods discussed above, the native splice junction may be unknown. Accordingly, one skilled in the art would predict that several possible artificial splice junctions exist that would result in the production of an active enzyme.

Once the intron is deleted, overexpression of the T. litoralis DNA polymerase can be achieved, for example, by separating the T. litoralis DNA polymerase gene from its endogenous control elements and then operably linking the polymerase gene to a very tightly controlled promoter such as a T7 expression vector. See, Rosenberg, et al., Gene (1987) 56:125–135, which is hereby incorporated by reference. Insertion of the strong promoter may be accomplished by identifying convenient restriction targets near both ends of the T. litoralis DNA polymerase gene and compatible restriction targets on the vector near the promoter, or generating restriction targets using site directed mutagenesis (Kunkel (1984), supra), and transferring the T. litoralis DNA polymerase gene into the vector in such an orientation as to be under transcriptional and translational control of the strong promoter.

T. litoralis DNA polymerase may also be overexpressed by utilizing a strong ribosome binding site placed upstream of the T. litoralis DNA polymerase gene to increase expression of the gene. See, Shine and Dalgarno, Proc. Natl. Aced. Sci. USA (1974) 71:1342–1346, which is hereby incorporated by reference.

The recombinant vector is introduced into the appropriate host using standard techniques for transformation and phage infection. For example, the calcium chloride method, as described by Cohen, S.N., PNAS (1972) 69:2110 is used for E. coli, the disclosure of which is incorporated by reference. The transformation of Bacillus is carried out according to the method of Chang, S., et al., Molecular and General Genetics (1979) 168:111, the disclosure of which is incorporated by reference. Transformation of yeast is carried out according to the method of Parent, et el., Yeast (1985) 1:83–138, the disclosure of which is incorporated by reference. Certain plant cells can be transformed with Agrobacterium tumefaciens, according to the method described by Shaw, C.H., et el., Gene (1983) 23:315, the disclosure of which is incorporated by reference. Transformation of animal cells is carried out according to, for example, the method described in Virology (1973) 52:456, the disclosure of which is incorporated by reference. Transformation of insect cells with Baculovirus is carried out according to, for example, the method described in Biotechnology (1988) 6:47, the disclosure of which is incorporated herein by reference.

The transformants are cultivated, depending on the host cell used, using standard techniques appropriate to such cells. For example, for cultivating E. coli, cells are grown in LB media (Maniatie, supra) at 30° C. to 42° C. to mid log or stationary phase.

The T. litoralis DNA polymerase can be isolated and purified from a culture of transformed host cells, for example, by either extraction from cultured cells or the culture solution.

When the T. litoralis DNA polymerase is to be extracted from a cultured cell, the cells are collected after cultivation by methods known in the art, for example, centrifugation. Then, the collected cells are suspended in an appropriate buffer solution and disrupted by ultrasonic treatment, lysozyme and/or freeze-thawing. A crude extract containing the T. litoralis DNA polymerise, is obtained by centrifugation and/or filtration.

When the T. litoralis DNA polymerase is secreted into the culture solution, i.e., alone or as a fusion protein with a secreted protein such as maltose binding protein, the supernatant is separated from the cells by methods known in the art.

The separation and purification of the T. litoralis DNA polymerase contained in the culture supernatant or the cell extract can be performed by the method described above, or by appropriate combinations of known separating and purifying methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse-phase high performance liquid chromatography and methods utilizing a difference in isoelectric point such as isoelectric focusing electrophoresis.

One preferred method for isolating and purification of the recombinant enzyme is accomplished using the multi-stage process as follows.

First, the cells, if frozen are thawed, suspended in a suitable buffer such as Buffer A (100 mM NaCl, 25 mM Tris pH 7.5, 0.1 mM EDTA, 10% glycerol, 0.05% Triton X-100), lysed and centrifuged. The clarified crude extract is then heated to 75° C. for approximately 30 minutes. The denatured proteins are removed by centrifugation.. The supernatant is then passed through a column that has high affinity for proteins that bind to nucleic acids such as Affigel Blue column (Biorad). The nucleic acids present in the supernatant solution and many of proteins pass through the column and are thereby removed by washing the column with several column volumes with low-salt buffer at pH of about 7.0. After washing, the enzyme is el uted with a 1 i near gradient such as 0.1 M to 1.5 M NaCl Buffer A. The active fractions are pooled, dialyzed and applied to a phosphocellulose column. The column is washed and DNA polymerase activity eluted with a linear gradient of 0.1 to 1.0 M NaCl in Buffer B (100 M NaCl, I5 mM KPO$_4$, 0.1 mM EDTA, 10% glycerol, 0.05% Triton X-100, pH 6.8). The fractions are collected and BSA is added to each fraction. The fractions with DNA polymerase activity are pooled. The *T. litoralis* DNA polymerase obtained may be further purified using the standard product purification techniques discussed above.

Stabilization and Use of the *T. litoralis* DNA Polymerase

For long-term storage, the thermostable enzyme of the present invention is stored in the following buffer: 0.05 M NaCl, 0.01M KPO$_4$ (pH 7.4), 0.1 mM EDTA and 50% glycerol at $-20°$ C.

The *T. litoralis* DNA polymerase of the present invention may be used for any purpose in which such an enzyme is necessary or desirable. For example, in recombinant DNA technology including, second-strand cDNA synthesis in cDNA cloning, and DNA sequencing. See Maniatis, et al., supra.

The *T. litoralis* DNA polymerase of the present invention may be modified chemically or genetically to inactivate the 3'-5' exonuclease function and used for any purpose in which such a modified enzyme is desirable, e.g., DNA sequencing.

For example, genetically modified *T. litoralis* DNA polymerase may be isolated by randomly mutagenizing the *T. litoralis* DNA polymerase gone and then screening for those mutants that have lost exonuclease activity, without loss of polymerase activity. Alternatively, genetically modified *T. litoralis* DNA polymerase is preferably isolated using the-site-directed mutagenesis technique described-in Kunkel, T.A., PNAS (1985) 82:488–492, the disclosure of which is herein incorporated by reference.

In addition, the *T. litoralis* DNA polymerase of the present invention may also be used to amplify DNA, e.g., by the procedure disclosed in U.S. Pat. Nos. 4,683,195, 4,683,202 and 4,800,159.

Construction of Genomic. DNA Library and Screening for Thermostable Polymerase From Archaebacteria other than *T. litoralis*

In accordance with the present invention, cross hybridization of a target Archaebacterium genomic DNA library using an DNA probe prepared from the DNA polymerase gone of *T. litoralis* and/or cross-reactivity with mouse anti-*T. litoralis* antiserum allows for the identification and isolation of the DNA polymerase genes from other archaebacterium, such as Methanococcus, Methanobacter, Methanomicrobium, Halobacter, Thermoplasma, *Thermococcus, Pyrococcus,* and the like (see, e.g. Woese, C., *Microbiological Reviews,* pp. 221–270, June 1987, the disclosure of which is hereby incorporated by reference).

In general, DNA from other archaebacterium can be isolated using the method described above. As with *T. litoralis* The archaebacterium DNA once isolated can be used to construct genomic libraries as either random fragments or restriction enzyme fragments. The latter approach is preferred. This approach generally entails cutting the target genomic DNA with various restriction enzymes and probing the fragments so formed with, for example, a *T. litoralis* DNA probe. A library is thereafter formed from one or more of the enzymes which produce a single hybridization band and which are about 4Kb or large enough to at least code for the molecular weight of the target DNA polymerase.

Although methods are available to screen both plasmids and phage using antibodies or DNA probes (Young and Davis, PNAS (1983) 80:1194–1198; Maniatis et al, supra) in accordance with the present invention it has been found that phage systems tend to work better and are therefore preferred for the first libraries.

Genomic libraries can be screened using the colony or plaque hybridization procedure (Maniatis, et al. supra) or using the antibody plaque DNA procedures. In the colony or plaque hybridization procedure, DNA probes may be formed by labelling a polymerase gene from a related organism, for example, *T. litoralis*. The genomic library is hybridized with labeled probe under conditions which depend on the stringency desired, which may be experimentally determined in each case as described below.

Specifically, although each archaebacterium will require its own set of hybridization conditions, in order to maximize the detectability of the target DNA, several basic approaches can be followed. Optimum hybridization conditions and probes can be determined for each target archaebacterium, for example, by performing test Southern blots at various temperatures. Hybridization is typically carried out in 4X SET, 0.1 M sodium phosphate, pH 7.0, 0.1% Na pyrophosphate, 0.1% SDS, 1X Denhardts solution (Maniatis, supra). Probe selection can also vary with respect to size and regions of the *T. litoralis* DNA polymerase gene (FIG. 6). Optimum probes can be determined for a target archaebacterium by performing test Southern blots as described above with large or small DNA fragments, or even oligomerso One could, for example, select probes that are totally within one of the intervening sequences of *T. litoralis* to screen for intervening sequences in the target archaebacterium's DNA polymerase gene, or such probes could be limited to mature polymerase coding regions.

In general, the DNA probe could be the entire sequence of FIG. 6, or a portion thereof. The DNA probe should be at least 20 nucleotides in length, preferably at least about 50 nucleotides in length, most preferably at least about 150 nucleotides in length. Three such DNA probes which may be used are the 1.3 kb fragment (nucleotides 1 to 1274 of FIG. 6), the 1.6 kb fragment (nucleotides 1269 to 2856 of FIG. 6), and the 1.9 kb fragment (nucleotides 2851 to 4771 of FIG. 6).

As with *T. litoralis,* the DNA coding for the target archaebacterium DNA polymerase may also be obtained using an antibody/plaque procedure. When genomic expression libraries are screened using the antibody/plaque procedure, since it is uncertain whether the target archaebacterium's control regions will function in *E. coli*, phage vectors which supply all necessary expression control regions such as λgt11 and λZap II are preferred for antibody screening. By cloning archaebacterium DNA into an appropriate site such as the EcoR I site of λgt11, the archaebacterium's DNA polymerase may be expressed either as a fusion protein with beta-galactosidase in λgt11 and λZapII or from its own endogenous promoter.

Once formed, the expression libraries can be screened either with anti-archaebacterium DNA polymerase antiserum from the target archaebacterium or, by antibody against the DNA polymerase of a closely related organism (i.e. *T. litoralis*, another extreme thermophile) using standard antibody/plaque procedures such as those described by Young and David, PNAS (1983), supra.

Using either procedure, the archaebacterium DNA polymerase DNA, coding for part or the whole gene, once identified can then be subcloned in, for example, pBR322, pBluescript, M13 or pUC19. If desired, the DNA sequence can be determined by, for example, the Sanger dideoxy chain-terminating method (Sanger, F., Nicklen, S. & Coulson, A.R. PNAS (1977) 74:5463–5467).

Identification of the DNA Encoding the DNA Polymerase

Once the genomic DNA expression library has been constructed and the target DNA coding for the archaebacterium DNA has been identified by use of DNA probes or antibody cross-reactivity from *T. litoralis*, one may confirm that a DNA polymerase sequence has been obtained as described above for *T. litoralis*. The resulting clone may be sequenced by standard methods such as by Sanger dedioxy sequencing.

Identification, Location and Removal of Intervening Sequencing and Overexpression of the DNA Polymerase In accordance with another aspect of the present invention, it has been found that the DNA coding for DNA polymerases from other archaebacterium also contain one or more intervening nucleotide sequences or introns. Moreover, it has been found that not only do such introns share substantial homology with the introns found in *T. litoralis*, they appear to be located in the same positions. More specifically, in accordance with the present invention, introns have been identified in the Pol α conserved region motifs in both *T. litoralis* and Pyrococcus sp. DNA polymerase genes. Without wishing to be bound by theory, it is believed that other archaebacteria also possess one or more intervening sequences in the coding region for their DNA polymerases. These introns can be identified in two ways. If the intron(s) is related to the intron(s) located in *T. litoralis* and/or *Pyrococcus sp.* DNA polymerases genes, they can be identified by low stringency hybridization to DNA probes derived from the intron sequences of *T. litoralis* or *Pyrococcus sp.* DNA polymerase genes. Secondly, once the archaebacterium DNA polymerase gene has been identified and isolated as described above, its DNA polymerase gene can be sequenced at the DNA level and the sequence compared to (1) other DNA polymerases to identify non-similar segments, or (2) conserved motifs to look for the absence of one or more of Regions I–VI, followed by identification of interruption points in the Region(s) which are absent.

Once identified, the intron(s) can be removed in vitro by, for example, the techniques described above and in the Examples for removal of the two introns in the *T. litoralis* DNA polymerase gene.

The following examples are given to illustrate embodiments of the present invention as it is presently preferred to practice. It will be understood that the examples are illustrative, and that the invention is not to be considered as restricted except as indicated in the appended claims.

EXAMPLE I

Purification of a Thermostable DNA Polymerase From Thermoccoccus Litoralis

*T. litoralis* strain NS-C (DSM No. 5473) was grown in the media described by Belkin, et el. supra, containing 10 g/1 of elemental sulfur in a 100 liter fermentor at its maximal sustainable temperature of approximately 80° C. for two days. The cells were cooled to room temperature, separated from unused sulfur by decanting and collected by centrifugation and stored at −70° C. The yield of cells was 0.8 g per liter.

183 g of cells obtained as described above, were suspended in 550 ml of buffer A (10 mM $KPO_4$ buffer, pH 7.4; 1.0 mM EDTA, 1.0 mM beta-mercaptoethanol) containing 0.1 M NaCl and sonicated for 5 minutes at 4° C. The lysate was centrifuged at 15,000 g for 30 minutes at 4° C. The supernatant solution was passed through a 470 ml Affigel blue column (Biorad). The column was then washed with 1000 ml of buffer A containing 0.1 M NaCl. The column was eluted with a 2000 ml linear gradient from 0.1 to 2.0 M NaCl in buffer A. The DNA polymerase eluted as a single peak at approximately 1.3 M NaCl and represented 80% of the activity applied. The peak activity of DNA polymerase (435 ml) was dialyzed against 4 liters of buffer A, and then applied to 80 ml Phosphocellulose column, equilibrated with buffer A containing 0.1 M NaCl. The column was washed with 160 ml of buffer A containing 0.1 M NaCl, and the enzyme activity was eluted with 1000 ml linear gradient of 0.1 to 1.0 M NaCl in buffer A. The activity eluted as a single peak at 0.6 M NaCl and represented 74% of the activity applied. The pooled activity (150 ml) was dialyzed against 900 ml of buffer A and applied to a 42 ml DNA-cellulose column. The column was washed with 84 ml of buffer A containing 0.1 M NaCl, and the enzyme activity eluted with a linear gradient of buffer A from 0.1 to 1.0 M NaCl. The DNA polymerase activity eluted as a single peak at 0.3 M NaCl, and represented 80% of the activity applied. The activity was pooled (93 ml). The pooled fractions were dialyzed against 2 liters of buffer A containing 0.05 M NaCl and then applied to a 1.0 ml HPLC mono-Q column (Pharmacia). The DNA polymerase activity was eluted with a 100 ml linear gradient of 0.05 M to 1.0 M NaCl in buffer A. The DNA polymerase activity eluted as a single peak at 0.1 M NaCl and represented 16% of the activity applied. The pooled fractions (3.0 ml) were diluted to 6 ml with buffer A and applied to an 1.0 ml HPLC mono-S column (Pharmacia) and eluted with a 100 ml linear gradient in buffer A from 0.05 to 1.0 M NaCl. The activity eluted as a single peak at 0.19 M NaCl and represented 75% of the activity applied.

By SDS-polyacrylamide gel electrophoresis (SDS-PAGE) and subsequent staining of the proteins using a colloidal stain (ISS Problue) more sensitive than Coomassie Blue (Neuhoff, et el., Electrophoresis (1988) 9:255–262), it was determined that the DNA polymerase preparation was approximately 50% pure: two major bands were present, one at 90,000 to 95,000 daltons and a doublet at 18,000 daltons. FIG. No. 1A. A very minor band was evident at approximately 80,000 to 85,000 daltons. At this level of purification the polymerase had a specific activity of between 30,000 and 50,000 units of polymerase activity per mg of polymerase protein. On a separate SDS-polyacrylamide gel verification of the identity of the stained band at 90,000 to 95,000 daltons was obtained by cutting the gel lane containing the purified *T. litoralis* polymerase into 18 slices. Embedded proteins were eluted from the gel by crushing the gel slices in a buffer containing 0.1% SDS and 100/μg/ml BSA. The eluted proteins were denatured by exposure to guanidine HCl, then renatured via dilution of the denaturant as described by Hager and Burgess *Analytical Biochemistry* (1980) 109:76–86. Polymerase activity as measured by incorporation of radioactivity labeled $^{32}$P-dCTP into acid-insoluble DNA (as previously described) and assayed for exonuclease activity (as measured by the release of $^3$H-labelled DNA to an acid soluble form as described in Example V). As shown in FIG. No. 1B, only the 90,000 to 95,000 daltons band alone showed either significant polymerase activity or exonuclease activity.

The DNA polymerase preparation was dialyzed against buffer A containing 0.05 M NaCl. As was determined by SDS-PAGE, much of the 18,000 dalton protein precipitated out of the solution. The yield of *T. litoralis* DNA polymerase was determined to be 0.5 mg by quantitative protein analysis, and this represented 6.5% of the total activity present in the starting crude extract.

Purified *T. litoralis* polymerase was electrophoresed and stained with either Coomassie Blue or the colloidal stain (ISS Problue) previously described to detect protein. One deeply staining protein band was seen at about 90,000 to 95,000 daltons; this molecular weight determination was obtained by comparison on the same gel to the migration of the following marker proteins (Bethesda Research Laboratories): myosin, 200,000 daltons; phosphorylase B, 97,400 daltons; BSA, 68,000 daltons; ovalbumin, 43,000 daltons, carbonic anhydrase 29,000 daltons; b-lactoglobulin, 18,400 daltons; lysoyzme 14,300 daltons.

EXAMPLE II

CLONING OF *T. LITORALIS* DNA POLYMERASE GENE

A. PRODUCTION OF MOUSE ANTI-T. LITORALIS DNA POLYMERASE ANTISERA

Immunization of Mice

A 3 ml solution containing 0.4 mg of polymerase protein (obtained by the method of Example I) was concentrated at 4° C. to approximately 0.3 ml and used to inoculate two mice. The purified *T. litoralis* polymerase preparation consisted of four bands of approximately 85–95, 75–85, and a doublet of 10–25 kDal on Coomassie blue stained SDS-PAGE gels. As shown in Example I, the *T. litoralis* polymerase is approximately 90–95 kDal. Both *T. litoralis* polymerase antisera recognize all four proteins present in the immunogen.

The immunization schedule was as follows: mouse one was immunized intraperitioneally (IP) with 20 μg of *T. litoralis* polymerase, prepared as above, in Freunds' complete adjuvant (FCA). Seven days later, both mice were immunized IP with 50 μg *T. litoralis* polymerase in FCA. Twenty-seven days later both mice were immunized IP with 30 μg *T. litoralis* polymerase for mouse one and 50 μg *T. litoralis* polymerase for mouse two in Freunds' incomplete adjuvant. Mouse one was bled two weeks later and mouse two was bled 20 days later. Sera was prepared from blood by standard methods (Harlow and Lane, *Antibodies: A. Laboratory Manual*, 1988).

Anti-*T. litoralis* polymerase antisera was diluted in TBSTT (20 mM Tri s pH 7.5, 150 mM NaCl, 0. 2% Tween 20, and 0.05Tri ton-X 100) containing 1% BSA, 0.1% NaAzide, 0.1% PMSF.

Preabsorption of Anti-*T. litoralis* Polymerase Antiserum Against *E. coli* Lysates Since most sera react with *E. coli* proteins, *T. litoralis* polymerase antisera were preabsorbed, using the following method, against *E. coli* proteins to reduce background reactivity when screening libraries or recombinant antigens. *E. coli* cell paste was thawed and lysed by sonication and soluble protein was bound to Affigel 10 (Biorad) as described by the manufacturer. 4 ml of *E. coli* resin were washed two times in TBS (TBSTT without detergents). 0.35 ml of sera was diluted approximately 1 to 5 in TBSTT, 1% BSA, 0.1% NaAzide and mixed with resin overnight at 4° C. The resin was pelleted by centrifugation and washed. The recovered preabsorbed sera was at a 1 to 17 dilution and was stored frozen at −20° C. until use. For screening, preabsorbed sera was diluted as above to a final concentration of 1:200.

B. IDENTIFICATION OF A PROBE FOR THE T. LITORALIS POLYMERASE GENE

Construction of a Lambda gt11 Expression Library

A probe for the *T. litoralis* polymerase gene was obtained following immunological screening of a lambda gt11 expression library.

*T. litoralis* DNA was partially digested as follows: four μg of *T. litoralis* DNA was digested at 37° C. with five units of Eco RI in a 40 μl reaction using Eco RI buffer (Eco RI buffer = 50 mM NaCl, 100 mM Tris pH 7.5, 20 mM MgCl2, 10 mM BME). Three μl of 100 mM EDTA was added to 15 μl samples at 30, 45 and 60 minutes. 2 μg of *T. litoralis* DNA was digested for 90 minutes at 37° C. with 20 units of Eco RI in 20 μl reaction using Eco RI buffer and the reaction was stopped by adding 2 μl of 100 mM EDTA. 0.2 μg of each digest was electrophoresed on an agarose gel to monitor the extent of digestion. Approximately 3 μg of *T. litoralis* DNA Eco RI partials (14 μl from the 60-minute digest and 19 μl from the 90-minute digest) were pooled to form the "Eco RI pool" and heated at 65° C. for 15 minutes.

0.5 μl of the Eco RI pool were ligated to 0.28 μg of Eco RI cut, bacterial alkaline phosphatase treated lambda gt11 DNA in a five μl reaction using standard ligation buffer (ligation buffer = 66 mM Tris pH 7.5, I mM ATP, 1 mM spermidine, 10 mM MgCl2, 15 mM DTT, and 2 mg/ml gelatin) and 0.5 μl T4 DNA ligase (New England Biolabs No. 202). The ligation was performed at 16° C. overnight. 4 μl of this ligation reaction were packaged using Gigapack Gold (Stratagene) according to the manufacturers instructions. After incubation at room temperature for two hours, the packaged phage were diluted in 500 μl of SM (SM = 100 mM NaCl, 8 mM MgSO4, 50 mM Tris pH 7.5, 0.01% gelatin) plus three drops chloroform. The packaged Eco RI library was called sample V6-1 and consisted of $1.1 \times 10^5$ individual phage. *E. coli* strain ER1578 was used for phage infection.

Immunological Screening of Lambda gt11 Expression Library

The initial phage library was screened (Young, R.A. and R.W. Davis Science, (1983) 222:778–782) with a 1:200 dilution of the antiserum produced above. 36 phage (V10-22 through V10-55) which reacted with the anti-*T. litoralis* DNA polymerase antiserum were picked and 16 phage were plaque purified.

The 16 antibody positive phage were used to lysogenize E. coli K-12 strain Y1089. Lysogens were screened for thermostable DNA polymerase activity, no activity was detected.

Western blots (Towbin, et al., PNAS, (1979) 76:4350-4354) from these 16 lysates were probed with anti-T. litoralis polymerase antiserum. All proteins from these lysates which reacted with T. litoralis polymerase antiserum were smaller than T. litoralis polymerase, and were-also smaller than beta-galactosidase, indicating that none were fusion proteins with beta-gal actosidase.

Eight of the 16 antibody positive phage were used to affinity purify epitope-specific antibodies from total antiserum (Beall and Mitchell, J. Immunological Methods, (1986) 86:217-223).

The eight affinity purified sera were used to probe Western blots of both purified T. litoralis polymerase and T. litoralis crude lysates. Antibody purified from NEB 618 plaques specifically reacted with T. litoralis polymerase in purified and T. litoralis crude lysates. This was strong evidence that phage NEB 618 encodes approximately 38 kDal of the amino terminus of the T. litoralis polymerase.

Characterization of Phage NEB 618 and Subcloning of Eco RI Inserts

Western blot analysis indicated that phage NEB 618 synthesized several peptides ranging in size from approximately 15–40 kDal which bound T. litoralis polymerase antisera. DNA from phage NEB 618 was purified from liquid culture by standard procedures (Maniatis, et al., supra.) Digestion of NEB 618 DNA with Eco RI yielded fragments of 1.3 and 1.7 kb. An Eco RI digest of NEB 618 DNA was ligated to Eco RI cut pBluescript ONA. 20 µg of pBluescriptSK+ were digested with 40 units of Eco RI in 40 µl Eco RI buffer at 37° C. for three hours, followed by 65° for 15 minutes. 10 µg of NEB 618 DNA were digested with 40 units of Eco RI in 40 µl Eco RI buffer at 37° C. for 75 minutes, followed by 65° C. for 15 minutes. 1.75 µg of Eco RI cut NEB 618 DNA were ligated to 20 ng Eco RI cut pBluescriptSK+ with one µl T4 DNA ligase (New England Biolabs No. 202) in 10 µl ligation buffer. The ligation was performed overnight at 16° C. JM101 CaCl competent cells (Maniatis, et al., supra) were transformed with 5 µl of the ligation mixture. Of 24 recombinants examined, all but one contained the 1.7 kb fragment; clone V27-5.4 contained the 1.3 kb T. litoralis DNA fragment.

Antibodies from T. litoralis polymerase mouse antisera were affinity purified, as described above, on lysates from V27-5.4 (encoding the 1.3 kb Eco RI fragment) and V27-5.7 (encoding the 1.7 kb Eco RI fragment in pBluescript) and reacted with Western blot strips containing either purified or crude T. litoralis polymerase. Antibodies selected on lysates of V27-5.4 reacted with T. litoralis polymerase in both crude and purified preparations. In addition, the first three amino acids from the N-terminal protein sequence of native T. litoralis polymerase (methionine-isoleucine-leucine) are the same as in the predicted open reading frame (ORF) in the V27-5.4 clone.

From these results it was concluded that V27-5.4 encoded the amino terminal of T. litoralis polymerase. The 1.3 kb Eco RI fragment of V27-5.4 comprises nucleotides 1 to 1274 of FIG. No. 6. The insert DNA was large enough to encode the biggest peptides synthesized by this clone, but not the entire T. litoralis polymerase.

C. Construction and Screening of T. Litoralis Secondary Libraries

Antibody screening discussed above, had identified the DNA fragment coding the amino terminal half of the T. litoralis polymerase. In order to find a fragment large enough to code for the entire gene, restriction digests of T. litoralis DNA were probed with the amino terminal half of the polymerase gene contained in clone V27-5.4. Restriction digests were performed in separate tubes using a master mix which contained 1.2 µg of T. litoralis DNA in 39 µl of restriction enzyme buffer (REB, restriction enzyme buffer =50 mM NaCl, 10 mM Tris pH 7.5, 20 mM MgCl2, 10 mM BME), to which 1.5-200 U of enzyme were added as followed: 1.5 U AvrII, 9 U EaeI, 10 U NheI, 20 U NotI, g U SpeI, 20 U XhoI, 30 U XbaI, 20 U SacI, 10 U BamHI, 20 U ClaI, 20 U HindIII, 20 U PstI, 12 U NaeI, 10 U ScaI, 12 U XmnI, 20 U EcoRV, 20 U Sal, 20 U Eco RI, 200 U EagI, 20 U DraI, 5 U HapI, 8 U NruI, 4 U SnaBI, 8 U StuI, 10 U BclI, 8 U BglII, 10 U RsaI, 10 U HaeIII, 8 U AluI, 4 U HincII, 10 U PvuII, 6 U SspI. One µl 10 mg/ml BSA was added to the HincII digest. Bali digest was prepared as above except there was 0 mM NaCl in the buffer. All digests were overnight at 37° C. except BclI which was incubated at 50° C. Digests were electrophoresed on agarose gels and transferred to NC (Southern, J. Mol. Biol. (1975) 98:503-517). The filters were probed with radiolabeled V27-5.4 DNA and hybridization was detected by autoradiography. In most digests, V27-5.4 DNA hybridized to fragments greater than 20 kb, except BamHI (approximately 14 kb), Eco RI (1.3 kb), HindIII (approximately 2.4, 5.4 kb), XbaI (approximately 8 kb), ClaI (approximately 4.4, 5.5 kb), Bali (approximately 8.5 kb), HinctI (approximately 2.1, approximately 2.4 kb), NruI (approximately 5.5 kb), BglII (approximately 2.9 kb), HaeIII (approximately 1.3, approximately 1.4 kb) and RsaI which gave numerous small bands.

Digests yielding single fragments large enough to encode the entire polymerase gene, estimated to be 2.4-3 kb, based on the size of the native protein, were BamHI, XbaI, and NruI.

BamHI Library

A BamHI genomic library was constructed using lambda DashII. Lambda DashII is a BamHI substitution vector that can be used to clone 10-20 kb BamHI DNA fragments. 25-75 nanograms of T. litoralis genomic DNA digested with BamHI, as described above, was ligated to 0.5 µg BamHI digested, calf intestine phosphatase treated lambda DashII DNA in five µl of standard ligation buffer including 0.5 µl T4 DNA ligase (New England Biolabs No. 202). Three µl of the ligation reaction was packaged (Gigapack Plus, Stratagene) as described above. Plaque lifts of 8,000 plaques from the lambda DashII library were probed with labeled gel purified 1.3 kb Eco RI fragment from clone V27-5.4 (Maniatis, et al., supra). 2.5% of the phage hybridized to the 1.3 kb Eco RI DNA fragment, two of which were plaque purified (clones lambda NEB 619 and lambda V56-9). Both phage contained a 12-15 kb BamHI fragment which hybridized to the 1.3 kb Eco RI fragment and contained the approximately 8 kb XbaI and approximately 5.5 kb NruI fragments. The BamHI insert was subcloned into pBR322. Colonies containing this fragment grew very poorly and, based on the polymerase assay described above, failed to produce detectable levels of thermostable DNA polymerase.

XbaI Library

*T. litoralis* DNA digested with XbaI was cloned into the XbaI site of pUC19. Colony lifts were probed with radiolabeled V27-5.4 DNA. No positive clones were detected.

The XbaI fragment from the BamHI insert in lambda NEB 619 (BamHI library above) was subcloned into the XbaI site of pUC19. Approximately 0.3 μg of NEB 619 DNA digested with BamHI was ligated to 0.1 μg pUC19 DNA digested with BamHI using two μl T4 DNA ligase (New England Biolabs No. 202) in 20 μl of standard ligation buffer. The ligation was incubated overnight at 16° C. CaCl$_2$ competent JM101 and XL-I cells were transformed with five μl of ligation mix and incubated overnight at 37° C. (Maniatis, et al., supra). Colony lifts were probed with radiolabeled purified 1.3 kb Eco RI fragment from V27-5.4 DNA. No positives were detected. Competent RRI cells were transformed with 10 μl of ligation mix and incubated overnight at 30° C. Micro-colonies were picked and mini-plasmid preparations (boiling method, Maniatis, et al., *supra*) analyzed. Most of these clones contained the approximately 8 kb XbaI fragment. The rationale for this latter experiment was that since the BamHI clones grew poorly, there would be an increased chance of isolating a plasmid containing the *T. litoralis* polymerase gene from an XbaI colony that also grew slowly. Also, lower temperature of incubation results in less copies of pUC19 plasmids per cell. These results provided evidence that the *T. litoralis* polymerase gene was toxic to *E. coli*. Using the polymerase activity assay described above, no thermostable polymerase activity was detected in these clones. Restriction analysis indicated that the XbaI clones should contain the entire polymerase gene. See FIG. No. 2.

NruI Libraries

Approximately 0.3 μg of NEB 619 DNA (BamHI library above) cut with NruI was ligated to 0.1 μg of pUC19 DNA cut with HincII exactly as described for the XbaI library. Again, no positives were found by hybridization when cells were incubated at 37° C., but when transformants were incubated at 30° C., many micro-colonies were observed. The majority of these micro-colonies contained the approximately 5.5 kb NruI insert. Using the polymerase activity assay described above, no thermostable polymerase activity was detected in these colonies. Analysis of these colonies determined that when the direction of *T. litoralis* polymerase transcription was the same as lacZ in pUC19, the colonies failed to grow at 37° C. and were extremely unstable. However, colonies in which the direction of *T. litoralis* polymerase transcription was opposite of lacZ in pUC19, such as in clone Nru21, were more stable. This indicated that transcription of *T. litoralis* polymerase is detrimental to *E. coli*, and may explain why it was so difficult to clone the entire gene. Restriction mapping analysis indicated that the NruI clones should contain the entire polymerase gene. See FIG. No. 2.

Conclusions Concerning direct Cloning of the Polymerase

The *T. litoralis* is approximately 90–95 kDal which would require approximately 2.4–3.0 kb DNA to encode the entire gene. Restriction mapping analysis of the 1.3 kb Eco RI fragment, coding for the amino-terminus of the *T. litoralis* polymerase gene, found within the BamHI, XbaI and NruI clones, discussed above, indicates that all three clones contain the entire polymerase gene. All of these larger clones were unstable in *E. coli*. Therefore, alternate methods, as discussed below, for cloning the polymerase were tested.

D. CLONING THE SECOND HALF OF T. LITORALIS POLYMERASE GENE

It is believed that when the entire *T. litoralis* polymerase gene was cloned in *E. coli* while under its endogenous control, mutations in the gene arose. To prevent selection of inactive mutants, the polymerase gene was cloned from the *T. litoralis* genome in 2 or more pieces which should each separably be inactive and therefore not selected against. Restriction mapping of the *T. litoralis* genome was used to determine which restriction enzymes would produce fragments that would be appropriate for cloning the second half of the *T. litoralis* polymerase gene. Although the above data indicates that expression of *T. litoralis* polymerase was toxic for *E. coli*, it was also possible that DNA sequences themselves, in or outside of the coding region, were toxic. Therefore, the minimum sized fragment which could encode the entire gene was determined to be the best choice. Restriction analysis indicated that there was an approximately 1.6 kb F-co RI fragment adjacent to the 3' end of the amino terminal 1.3 kb F-co RI fragment (see FIG. No. 2) which could possibly complete the polymerase gene.

Hybridization Probe for the Second Half of the *T. litoralis* DNA Polymerase Gene Since none of the previous clones expressed thermostable polymerase activity, it was possible that they had accumulated mutations in the coding sequence and would therefore not be suitable sources of the second half of the gene. Hybridization probes were therefore required in order to clone the downstream fragments from the genome. The approximately 3.2 kb NdeI/ClaI fragment from clone Nru21 (the Nru21 clone contains an approximately 5.5 kb insert, beginning approximately 300 bp upstream from the start of the polymerase gene) was subcloned into pSP73 (Promega) creating clone NC11. CaCl$_2$ competent RRI cells were transformed, as above, with the ligation mixture. Mini-plasmid preps of transformants were analyzed by digestion with NdeI and ClaI and clone NC11 containing the *T. litoralis* 3.2 kb NdeI/ClaI fragment was identified. This clone was stable in *E. coli*. The NC11 insert was sequenced (Sanger, et al., PNAS, (1977) 74:5463–5467). The ClaI end was identical to the V27-5.4 sequence (1.3 kb Eco RI fragment coding for the amino-terminus of the *T. litoralis* polymerase). The 1.3 kb Eco RI junction and beyond was sequenced using primers derived from the 1.3 kb Eco RI fragment sequence. The NdeI end was sequenced from primers within the vector.

Screen of Eco RI Genomic Libraries

10 μg of NC11 were digested with 30 U of Eco RI in 100 μl of Eco RI buffer at 37° C. for two hours. The approximately 1.5 kb Eco RI fragment was purified on DE-81 paper (Whatman) after electrophoresis. The approximately 1.6 kb Eco RI fragment was radiolabeled and used to probe the original Eco RI lambda gtll library. Infection and plaque lifts were performed as above. Three positives were identified and plaque purified. All contain the approximately 1.6 kb Eco RI fragment, but some also contain other inserts.

An Eco RI library was also constructed in lambda ZapII. 2 μg of *T. litoralis* DNA were digested with 20 U Eco RI for five hours at 37° C. in 20 μl Eco RI buffer and then heat treated at 55° C. for 15 minutes. Approximately 15 nanograms of *T. litoralis* DNA/Eco RI was ligated to 0.5 μg of Eco RI cut, phosphatased lambda ZapII DNA (Stratagene) with 0.5 μl T4 DNA ligase (New England Biolabs No. 202) in 5 μl of ligation buffer at 16° C. overnight. 4 μl of ligated DNA was packaged (GigaPack Gold, Stratagene). Infection and plaque lifts were performed as above. Approximately 1,500 phage were probed with radiolabeled approximately 1.5 kb Eco RI fragment as above. Five hybridization positive plaques were picked and three were plaque purified. Two phage (NEB 620 and V109-2) were rescued as pBluescript recombinants (V117-1 and V117-2) by in-vivo excision according to the manufacturer's instructions (Stratagene). Both contained the approximately 1.6 kb Eco RI fragment plus different second fragments. The 5' end was sequenced and corresponds to the sequence determined from NC11 (ClaI/NdeI fragment). See FIG. No. 2. This Eco RI fragment contains 3/6 of the T4 DNA polymerase family homology islands as described by Wang, et al., supra. The 1.6 kb Eco RI fragment comprises nucleotides 1269 to 2856 of FIG. No. 6.

The sequence of the 1.6 kb Eco RI and ClaI/NdeI fragments indicated that the 1.9 kb Eco RI fragment may be necessary to complete the polymerase gene. Lambda ZapII phage, V110-1 through V110-7, containing the 1.9 kb Eco RI fragment were identified as described above for NEB 620 using labeled probes. Two phage (V110-2 and V110-4) were rescued as pBluescript recombinants (V153-2 and V153-4) by in-vivo excision according to the manufacturers instructions (Stratagene). Both contained the approximately 1.9 kb Eco RI fragment plus different second fragments. The 1.9 kb Eco RI fragment had sequence identity with the overlapping region in NC11. The 1.9 kb Eco RI fragment comprises nucleotides 2851 to 4771 of FIG. No. 6.

The entire *T. litoralis* polymerase gene has been cloned as BamHI, XbaI and NruI fragments which were unstable and from which the active enzyme was not detected. The gene has also been cloned in four pieces (1.3 kb Eco RI fragment, approximately 1.6 kb Eco RI fragment, approximately 1.9 kb Eco RI fragment and an Eco RI/BamHI fragment containing the stop codon). The 1.3 kb Eco RI fragment stably expresses the amino terminal portion of the polymerase.

EXAMPLE III

Cloning of Active *T. Litoralis* DNA Polymerase

The *T. litoralis* polymerase gene found on the 14 kb BamHI restriction fragment of bacteriophage NEB619 (ATCC No. 40795), was sequenced using the method of Sanger, et al., PNAS (1977) 74:5463–5467. 5837 bp of continuous DNA sequence (SEQ ID NO:1) was determined beginning from the 5' end of the 1.3 kb EcoRI fragment (position NT 1), see FIG. No. 6.

From analysis of the DNA sequence, it was determined that the polymerase gene begins at NT 291 in the 1.3 kb EcoRI fragment. A translation termination site beginning at NT 5397 was also located. Since the apparent molecular weight of *T. litoralis* polymerase was approximately 90–95 Kdal, it was predicted that the gene should be ~2900 bp. Instead, a 5106 bp open reading frame (ORF) was identified with a coding capacity of 1702 amino acids (aa) or ~185 Kdal.

By sequence homology with other DNA polymerases, an example of which is set out in FIG. No. 7, it was discovered that the *T. litoralis* polymerase gene was interrupted by an intron or intervening sequence in DNA polymerase consensus homology region III (hereinafter "IVSI") (Wang, T., et al., FASEB *Journal* (1989) 3:14-21 the disclosure of which is herein incorporated by reference). The conserved amino acids of the consensus DNA polymerase homology region III are shown in FIG. No. 7. In the Figure, the conserved amino acids are underlined. As can be seen in FIG. No. 7, the left side of the *T. litoralis* homology island III (SEQ ID NO:2) begins at NT 1737, and homology to the consensus sequence is lost after the Asn and Ser residues. The right side of the *T. litoralis* homology island III (SEQ ID NO:3) can be picked up at NT 3384, at the Asn and Ser residues. When the two *T. litoralis* polymerase amino acid sequences were positioned so that the Asn and Set residues overlap, as in FIG. No. 7, it was evident that a good match to the DNA polymerase homology region III existed.

Using the homology data, it was therefore predicted that an intervening sequence existed in the *T. litoralis* DNA separating the left and right halves of the DNA polymerase homology region III.

In one preferred embodiment, the intervening sequence was deleted by identifying unique restriction enzyme sites in the coding region which were near the intervening sequence splice junction. A synthetic duplex oligonucleotide was synthesized, and used to bridge the gap between the two restriction fragments. A multi-part sequential ligation of the carboxy end restriction fragments, the bridging oligonucleotide, the amino end restriction fragment, and the expression vector, resulted in the formation of an expression vector containing an intact polymerase gene with the intervening sequence deleted.

Specifically, the DNA fragments or sequences used to construct the expression vector of the present invention containing the *T. litoralis* DNA polymerase gene with the intervening sequence deleted were as follows:

1. An NdeI site was created by oligonucleotide directed mutagenesis (Kunkel, et al., *Methods in Enzomology* (1987) 154:367:382) in plasmid V27-5.4 (Example II, Part B) such that the initiation codon of the polymerase coding region is contained within the NdeI site.

| Original sequence (nucleotides 288–293) | ...TTT ATG... |
|---|---|
| New Sequence | ...<u>CAT ATG</u>... |

Sequences from the newly created NdeI site to the ClaI site (approximately 528 base pairs) were utilized in the construction of the expression vector.

2. An approximately 899 bp sequence between the ClaI and PvuI site of NC11 (Example II, Part D).
3. A synthetic duplex which spans the intervening sequence, connecting PvuI and Bsu36I sites derived from other fragments, as set out in FIG. No. 12.

In FIG. No. 12, the first line indicates the original sequence at the 5' end of the splice Junction. (nucleotides 1721-1784, SEQ ID NO:1), the second line indicates the original sequence of the 3' end of the splice junction (nucleotides 3375–3415, SEQ ID NO:1), and the third and fourth lines indicate the sequence of the synthetic duplex oligonucleotide.

4. A Bsu361 to BamHI fragment, approximately 2500 base pairs, derived from bacteriophage NEB 619 (Example II, Part C).
5. A BamHI to NdeI fragment of approximately 6200 base pairs representing the vector backbone, derived from pET11c (Studier, *Methods in Enzomology*, (1990) 185:66–89), and which includes:
   a) The T7 phi 10 promoter and ribosome binding site for the gene 10 protein
   b) Ampicillin resistance gene
   c) lacI$^q$ gene
   d) Plasmid origin of replication
   e) A four-fold repeat of the ribosomal transcription terminators (rrnb), Simons, et al., Gene (1987) 53:85–96.

The above DNA fragments, 1–5, were sequentially ligated under appropriate conditions using T4 DNA ligase. The correct construct was identified by restriction analysis and named pPR969. See FIG. No. 8. pPR969 was used to transform *E. coli* strain RRI, creating a strain designated NEB 687. A sample of NEB 687 was deposited with the American Type Culture Collection on Dec. 7, 1990 and bears ATCC No. 68487.

In another preferred embodiment, the *T. litoralis* polymerase gene, with the intervening sequence deleted, was cloned into a derivative of the Studier T7 RNA polymerase expression vector pET11c (Studier, (1990) supra). The recombinant plasmid V174–181 was used to transform *E. coli* strain BL21(DE3) pLysS, creating strain 175–181, designated NEB671. See FIG. Nos. 5 and 10.

A sample of NEB671 was deposited with the American Type Culture Collection on Oct. 17, 1990 and bears ATCC No. 68447.

A comparison between the predicted and observed molecular weights of the polymerase, even with the IVS1 deleted, revealed a discrepancy. The predicted molecular weight of the polymerase after removal of IVS1 in region III is 132 Kb, while the observed molecular weight of either the native (see Example I) or recombinant (see Example IV) polymerase is about 95 kD. The molecular weight discrepancy is due to an intron (hereinafter "IVS2") in homology region I. This finding is based on the following observations: The distance between homology regions III and I varies from 15–135 amino acids in members of the pol alpha family (Wang, (1989) supra). In *T. litoralis* there are 407 amino acids or ~44-kD separating these regions. *T. litoralis* DNA polymerase is very similar to human pol alpha except for 360 amino acids between conserved homology regions I and III where no similarity exists. Finally, no consensus region I is observed.

In addition, as determined by SDS-PAGE, a thermostable endonuclease of approximately 42–47 kD is also produced by the *T. litoralis* DNA polymerase clones of the present invention (see Example X). This endonuclease was purified to homogeneity by standard ion exchange chromatography, and was sequenced at its amino-terminal. The first 30 amino acids of the endonuclease correspond to the amino acids encoded beginning at nucleotide 3534 of the polymerase clone (SEQ ID NO:1). This corresponds to the portion of the polymerase which lacks homology with other known polymerases. This endonuclease does not react with anti-*T. litoralis* DNA polymerase antisera. While the exact mechanism by which the endonuclease is spliced out of the polymerase is unknown, it occurs spontaneously in both *E. coli* and *T. litoralis*.

EXAMPLE IV

Purification of Recombinant *t. Litoralis* DNA Polymerase

*E. coli* NEB671 (ATCC No. 68447) was grown in a 100 liter fermentor in media containing 10 g/liter tryprone, 5 g/liter yeast extract, 5 g/liter NaCl and 100 rag/liter ampicillin at 35° C. and induced with 0.3 mM IPTG at midexponential growth phase and incubated an additional 4 hours. The cells were harvested by centrifugation and stored at −70° C.

580 grams of cells were thawed and suspended in Buffer A (100 mM NaCl, 25 mM KPO$_4$ at pH 7.0, 0.1 mM EDTA, 0.05% Triton X-100 and 10% glycerol) to a total volume of 2400 ml. The cells were lysed by passage through a Gaul in homogenizer. The crude extract was clarified by centrifugation. The clarified crude extract volume was adjusted to 2200 mls with the above buffer and was heated to 75° C. for 30 minutes. The particulate material was removed by centrifugation and the remaining supernatant contained about 3120 mg of soluble protein.

The supernatant was applied to a DEAE-sepharose column (5×13 cm; 255 ml bed volume) linked in series to a phosphocellulose column (5×11 cm; 216 ml bed volume). The DEAE-sepharose flow-through fraction, containing the bulk of the enzyme, passed immediately onto the phosphocellulose column. Both columns were washed with 300 mls Buffer A, the two columns were disconnected, and the protein on the phosphocellulose column was eluted with a 2 liter linear gradient of NaCl from 0.1 M to 1 M formed in Buffer A.

The column fractions were assayed for DNA polymerase activity. Briefly, 1–4 µl of fractions were incubated for 5–10 minutes at 5° C. in 50 µl of 1X *T. litoralis* DNA polymerase buffer (10 mM KCl, 20 mM Tris-HCl (ph 8.8 at 24° C.), 10 mM (NH$_4$)$_2$SO$_4$, 2 mM MgSO$_4$ and 0.1% Triton X-100) containing 30 µM each dNTP and $^3$H-labeled TTP, 0.2 mg/ml activated calf thymus DNA and 100 µg/ml acetylated BSA, although it has been found that non-acetylated BSA is preferred. The mixtures were applied to Whatman 3 mm filters and the filters were subjected to three washes of 10% TCA followed by two washes of cold isopropanol. After drying of the filters, bound radioactivity representing incorporation of $^3$H-TTP into the DNA was measured. The active fractions were pooled and the enzyme activity levels in each pool were assessed using the above assay conditions except the dNTP level was raised to 200 µM each dNTP. Under these conditions one unit of enzyme activity was defined as the amount of enzyme that will incorporate 10 nmoles of dNTP into acid-insoluble material at 75° C. in 30 minutes.

The active fractions comprising a 300 ml volume containing 66 mg protein, were applied to a hydroxylapatite column (2.5×5 cm; 25 ml bed volume) equilibrated with Buffer B (400 mM NaCl, 10 mM KPO$_4$ at pH 7.0, 0.1 mM EDTA, 0.05% Triton X-100 and 10% glycerol). The protein was eluted with a 250 ml linear gradient of KPO$_4$ from 10 mM to 500 mM formed in Buffer B. The active fractions, comprising a 59 ml volume containing 27 mg protein, was pooled and dialyzed against Buffer C (200 mM NaCl, 10 mM Tris-HCl at pH 7.5, 0.1 mM EDTA, 0.05% Triton X-100 and 10% glycerol).

The dialysate was applied to a heparin-sepharose column (1.4×4 cm; 6 ml bed volume) and washed with 20 ml Buffer C. A 100 ml linear gradient of NaCl from 200 mM to 700 mM formed in Buffer C was applied to the column. The active fractions, comprising a 40 ml volume containing 16 mg protein was pooled and dialyzed against Buffer C.

The dialysate was applied to an Affi-gel Blue chromatography column (1.4×4 cm; 6 ml bed volume), washed with 20 mls Buffer C, and the protein was eluted with a 95 ml linear gradient from 0.2 M to 2 M NaCl formed in Buffer C. The active fractions, comprising a 30 ml volume containing 11 mg of protein, was dialyzed against a storage buffer containing 200 mM KCl, 10 mM Tris-HCl (pH 7.4), 1 mM DTT, 0.1 mM EDTA, 0.1% Triton X-100, 100 µg/ml BSA and 50% glycerol.

The T. litoralis DNA polymerase obtained above had a specific activity of 20,000–40,000 units/mg.

Characterization of recombinant T. litoralis polymerase

Recombinant and native T. litoralis polymerase had the same apparent molecular weight when electrophoresed in 5–10% SDS-PAGE gradient gels. Recombinant T. litoralis polymerase maintains the heat stability of the native enzyme. Recombinant T. litoralis polymerase has the same 3'→5' exonuclease activity as native T. litoralis polymerase, which is also sensitive to inhibition by dNTPs.

EXAMPLE V

OVER-EXPRESSION OF THE THERMOCOCCUS LITORALIS DNA POLYMERASE GENE

The T. litoralis DNA polymerase gene, with IVS1 deleted, e.g., V174–1B1 obtained in Example III, may be used in a number of approaches, or combinations thereof, to obtain maximum expression of the cloned T. litoralis DNA polymerase.

One such approach comprises separating the T. litoralis DNA polymerase gene from its endogenous control elements and then operably linking the polymerase gene to a very tightly controlled promoter such as a T7 expression vector (Rosenberg, et al., Gene (1987) 56:125–135). Insertion of the strong promoter may be accomplished by identifying convenient restriction targets near both ends of the T. litoralis DNA polymerase gene and compatible restriction targets on the vector near the promoter, or generating restriction targets using site directed mutagenesis (Kunkel, (1984), supra), and transferring the T. litoralis DNA polymerase gene into the vector in such an orientation as to be under transcriptional and translational control of the strong promoter.

T. litoralis DNA polymerase may also be overexpressed by utilizing a strong ribosome binding site placed upstream of the T. litoralis DNA polymerase gene to increase expression of the gene. See, Shine and Dalgarno, Proc. Natl. Acad. Sci. USA (1974) 71:1342–1346, which is hereby incorporated by reference.

Another approach for increasing expression of the T. litoralis DNA polymerase gene comprises altering the DNA sequence of the gene by site directed mutagenesis or resynthesis to contain initiation codons that are more efficiently utilized than E. coli.

Finally, T. litoralis DNA polymerase may be more stable in eukaryote systems like yeast and Baculovirus.

The T. litoralis DNA polymerase may be produced from clones carrying the T. litoralis DNA polymerase gene by propagation in a fermentor in a rich medium containing appropriate antibiotics. Cells are thereafter harvested by centrifugation and disrupted by sonication to produce a crude cell extract containing the T. litoralis DNA polymerase activity.

The crude extract containing the T. litoralis DNA polymerase activity is purified by the method described in Example I, or by standard product purification techniques such as affinity-chromatography, or ion-exchange chromatography.

EXAMPLE VI

PRODUCTION OF A T. LITORALIS DNA POLYMERASE 3' TO 5'EXONUCLEASE MUTANT

T. litoralis DNA polymerase lacking 3' to 5' exonuclease activity was constructed using site-directed mutagenesis to alter the codons for asp141 and glu143 to code for alanine. Site-directed mutagenesis has been used to create DNA polymerase variants which are reported to have reduced exonuclease activity, including phi29 (Cell (1989) 59:219–228 ) DNA polymerase I (Science (1988) 240:199–201) and T7 DNA polymerases (U.S. Pat. No. 4,942,130).

Site-directed mutagenesis of the polymerase of the present invention was accomplished using a modification of the technique described by Kunkel, T.A., PNAS (1985) 82:488–492, the disclosure of which is herein incorporated by reference. The V27-5.4 plasmid (see Example 2, Part B) was used to construct the site-directed mutants. V27-5.4 encodes the 1.3 kb EcoRI fragment in pBluescript SK+. E. coli strain CJ236 (Kunkel, et al., Methods in Enymology (1987) 154:367–382), a strain that incorporates deoxyuracil in place of deoxythymidine, containing the V27-5.4 plasmid was superinfected with the f1 helper phage IR1 (Virology, (1982) 122:222–226) to produce single stranded versions of the plasmid.

Briefly, the site-directed mutants were constructed using the following approach. First, a mutant oligonucleotide primer, 35 bases in length, was synthesized using standard procedures. The oligonucleotide was hybridized to the single-stranded template. After hybridization the oligonucleotide was extended using T4 DNA polymerase. The resulting double-stranded DNA was converted to a closed circular dsDNA by treatment with T4 DNA ligase. Plasmids containing the sought after mutations were identified by virtue of the creation of a PvuI site overlapping the changed bases, as set out below. One such plasmid was identified and named pAJG2.

The original and revised sequences for amino acid residues are 141,142, and 143:

| | ...asp | ile | glu |
|---|---|---|---|
| Original: | ...GAT | ATT | GAA |
| | ...ala | ile | ala |
| Altered: | ...GCG | ATC | GCA |

The newly created PvuI site, used to screen for the alteration, is underlined. Note that the middle codon was changed but that the amino acid encoded by this new codon is the same as the previous one.

An approximately 120 bp ClaI to NcoI fragment from V174-1B1 (see Example III) was replaced by the corresponding fragment bearing the above substitutions from pAJG2, creating pCAS4 (see FIG. No. 9). pCAS4 thus differs from V174-1B1 by 4 base pairs, namely those described above.

*E. coli* BL21 (DE3) plysS (*Methods in Enzomology*, (1990) 185:60–89) was transformed with pCAS4, creating strain NEB681. Expression of the mutant *T. litoralis* polymerase was induced by addition of IPTG.

A sample of NEB681 has been deposited with the American Type Culture Collection on Nov. 8, 1990, and bears ATCC No. 68473.

Relative exonuclease activities in the native *T. litoralis* DNA polymerase and the exonuclease minus variant isolated from *E. coli* NEB681 was determined using a uniformly [$^3$H]labeled *E. coli* DNA substrate. Wild type *T. litoralis* DNA polymerase was from a highly purified lot currently sold by New England Biolabs, Inc. The exonuclease minus variant was partially purified through DEAE sepharose and phosphocellulose columns to remove contaminants which interfered with the exonuclease assays. The indicated number of units of POLYMERASE were added to a 0.1 ml reaction containing *T. litoralis* DNA polymerase buffer [20 mM Tris-Hcl (pHB.8 at 25° C.), 10 mM KCl, 10 mM (NH$_4$)$_2$SO$_4$, 5 mM MgSO$_4$, 0.1% Triton X-100], 0.1 mg/ml bovine serum albumin, and 3 µg/ml DNA substrate (specific activity 200,000 cpm//µg) and the reaction was overlaid with mineral oil to prevent evaporation of the reaction. Identical reactions contained in addition 20 µM dNTP, previously shown to inhibit the exonuclease activity of the wild type enzyme. The complete reaction mixture was incubated at 70° C. for 60 minutes, following which 0.08 ml was removed and mixed with 0.02 ml 0.5 mg/ml sonicated herring sperm DNA (to aid in precipitation of intact DNA) and 0.2 ml of 10% trichloroacetic acid at 4° C. After mixing, the reaction was incubated on ice for 5 minutes, and the DNA then pelleted at 4° C. for 5 minutes in an Eppendorf centrifuge. 0.25 ml of supernatant was mixed with scintillation fluid and counted. The results of the sample counting, corrected for background, are shown in FIG. No. 11.

As illustrated in FIG. No. 11, the exonuclease minus variant was substantially free of exonuclease activity in the presence or absence of dNTPs under conditions where the native polymerase clearly demonstrated exonuclease activity. Conservatively estimating that a level of activity two-fold above background could have been detected, this implies that the exonuclease activity is decreased at least 60-fold in this variant.

EXAMPLE VII

*T. LITORALIS* DNA POLYMERASE HALF-LIFE DETERMINATION

The thermostability or half-life of the *T. litoralis* DNA polymerase purified as described above in Example I was determined by the following method. Purified *T. litoralis* DNA polymerase (25 units) was preincubated at 100° C. in the following buffer: 70 mM tris-HCl (pH 8.8 at 25° C.), 17 mM ammonium sulfate, 7 mM MgCl$_2$, 10 mM beta-mercaptoethanol, 200 µM each deoxynucleotide and 200 µg/ml DNAse-treated DNA. An initial sample was taken at time zero and a small aliquot equivalent to 5% of the enzyme mixture was removed at 10, 20, 40, 60, 90, 120, 150, and 180 minutes. The polymerase activity was measured by determining incorporation of deoxynucleotide into DNA as described previously.

A sample of Taq DNA polymerase obtained from New England Biolabs was subjected to the above assay. An initial sample was taken at time zero and a small aliquot equivalent to 5% of the enzyme mixture was removed at 4, 7, and 10 minutes. As shown in the FIG. No. 3, the half-life of the *T. litoralis* DNA polymerase at 100° C. was 60 minutes, while the half-life of the Taq polymerase at 100° C. was 4.5 minutes.

As shown in FIG. No. 3A, the half-life of *T. litoralis* DNA polymerase at 100° C. in the absence of stabilizers was 60 minutes, while in the presence of the stabilizers TRITON X-100 (0.15%) or BSA (100 µg/ml) the half-life was 95 minutes. This was in stark contrast to the half-life of Taq DNA polymerases at 100° C., which in the presence or absence of stabilizers was 4.5 minutes.

Figure 3A:
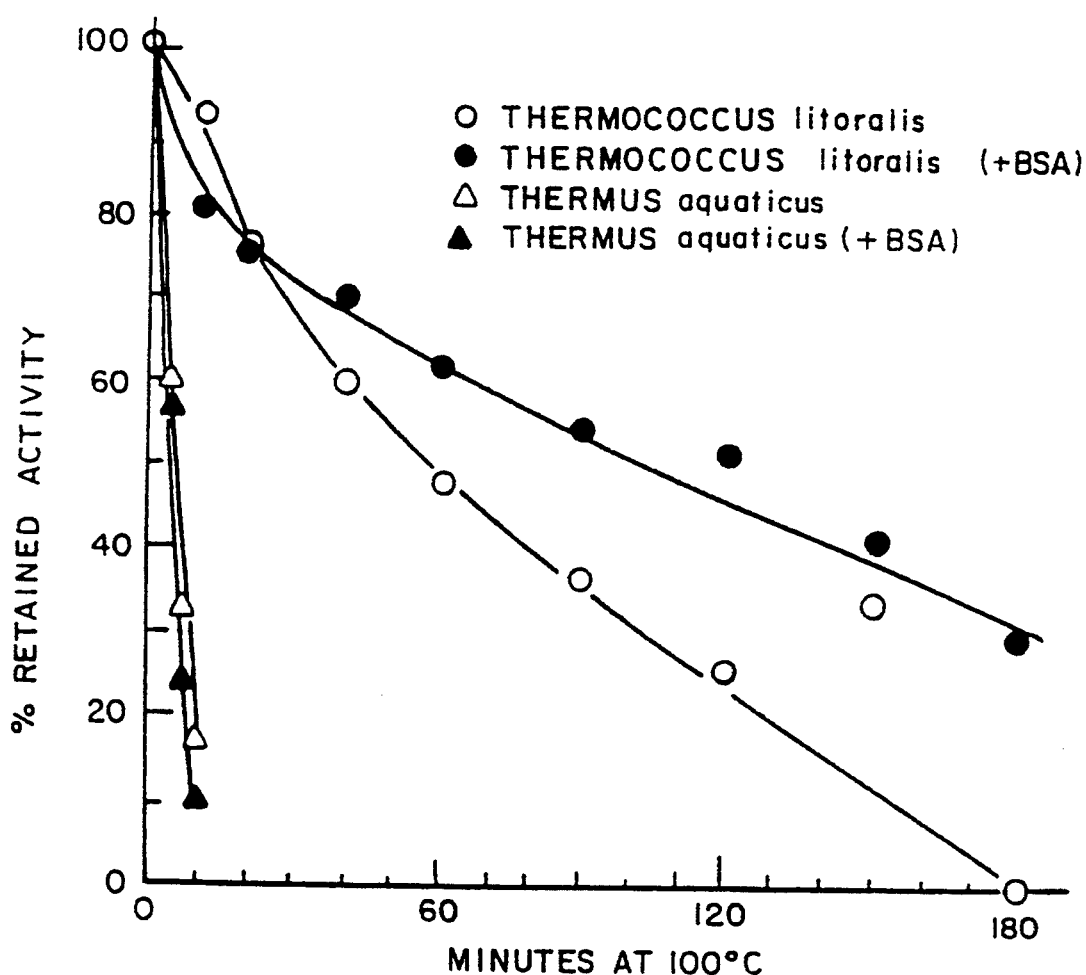
FIGS. 3A and 3B are graphs showing the half-life of native and recombinant *T. litoralis* DNA, respectively.
Figure 3B:
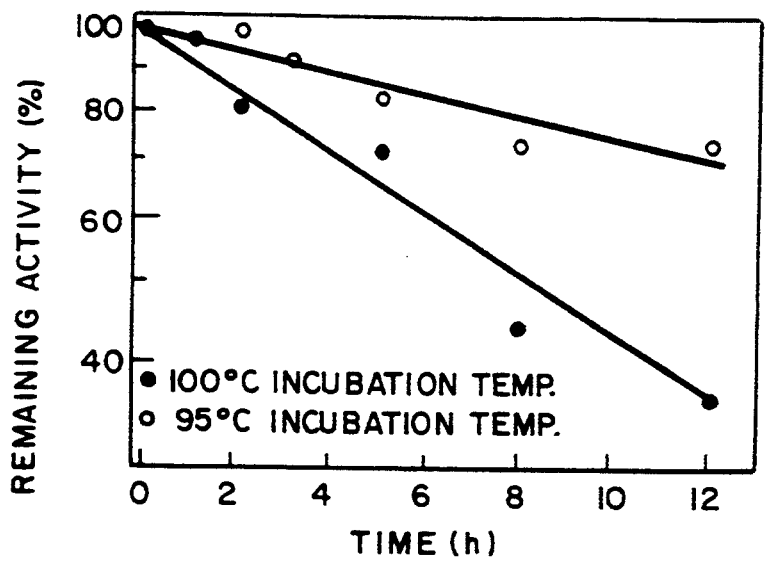
Figure 4:
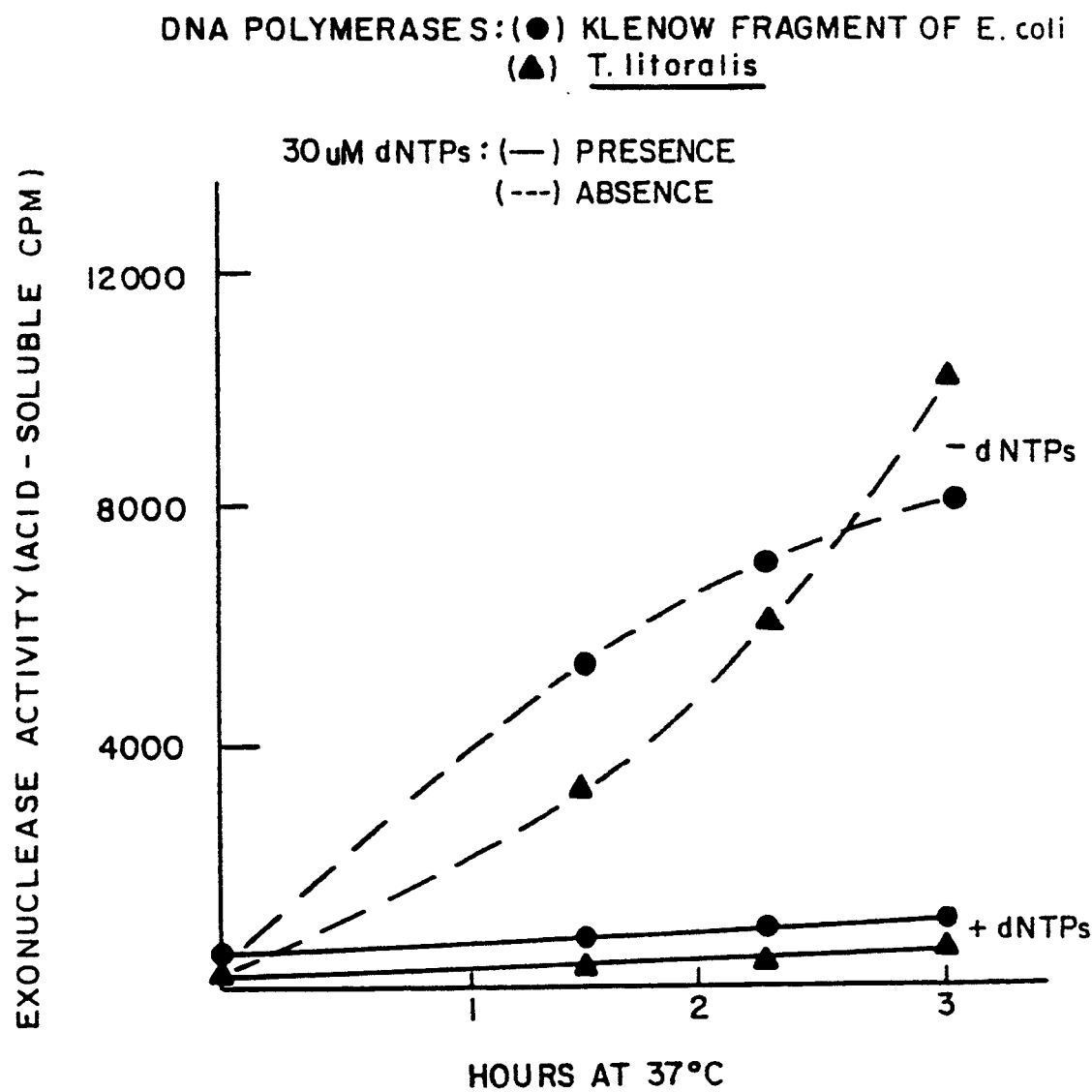
FIG. 4 is a graph showing the response of *T. litoralis* DNA polymerase and Klenow fragment to the presence or absence of deoxynucleotides.
Figure 5:
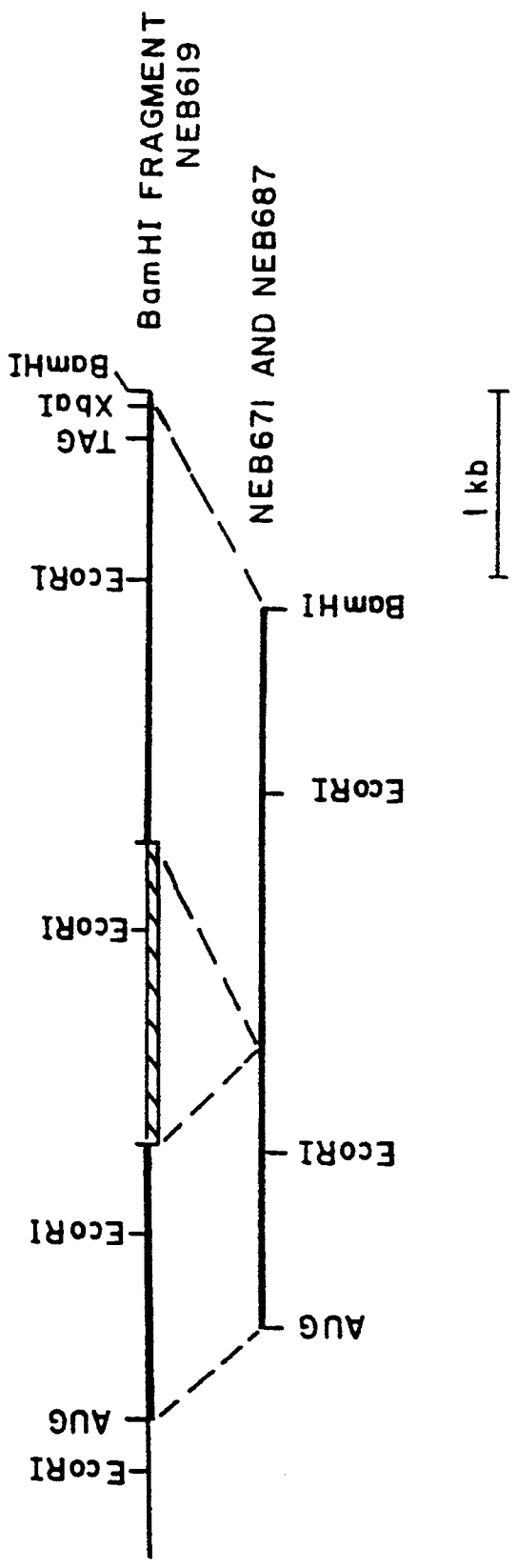
FIG. 5 is a restriction site map showing the organization of the *T. litoralis* DNA polymerase gene in native DNA (BamHI fragment of NEB 619) and in *E. coli* NEB671 and NEB687.
Figure 8:
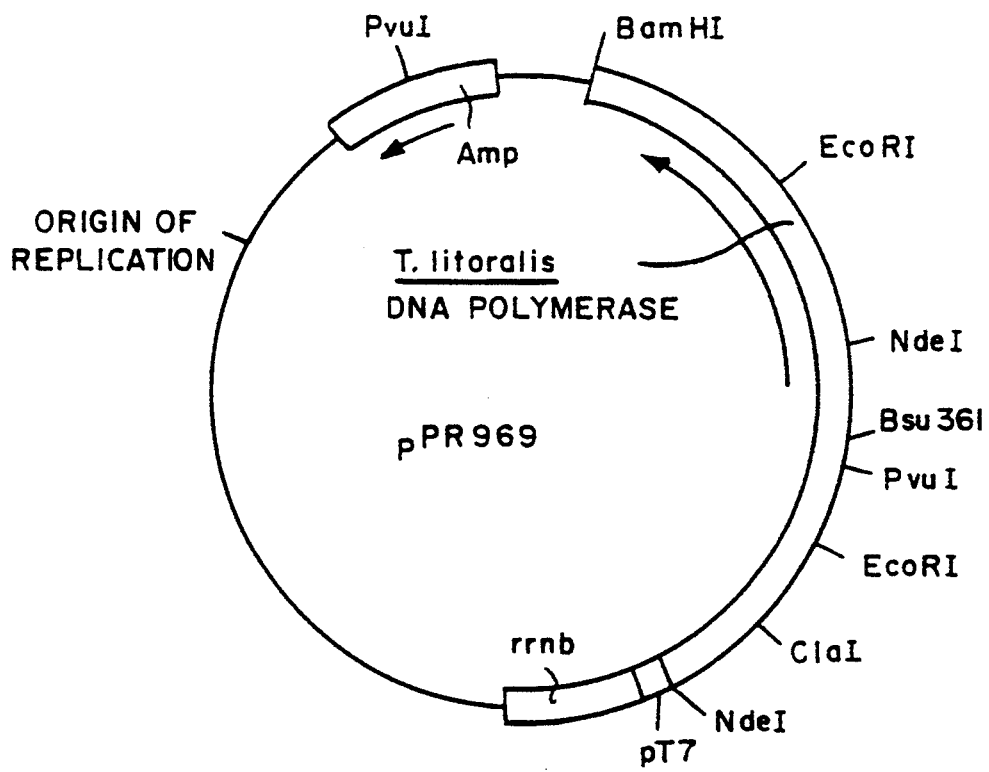
FIGS. 8-10 are representations of the vectors pPR969 and pCAS4 and V174-1B1, respectively.
Figure 9:
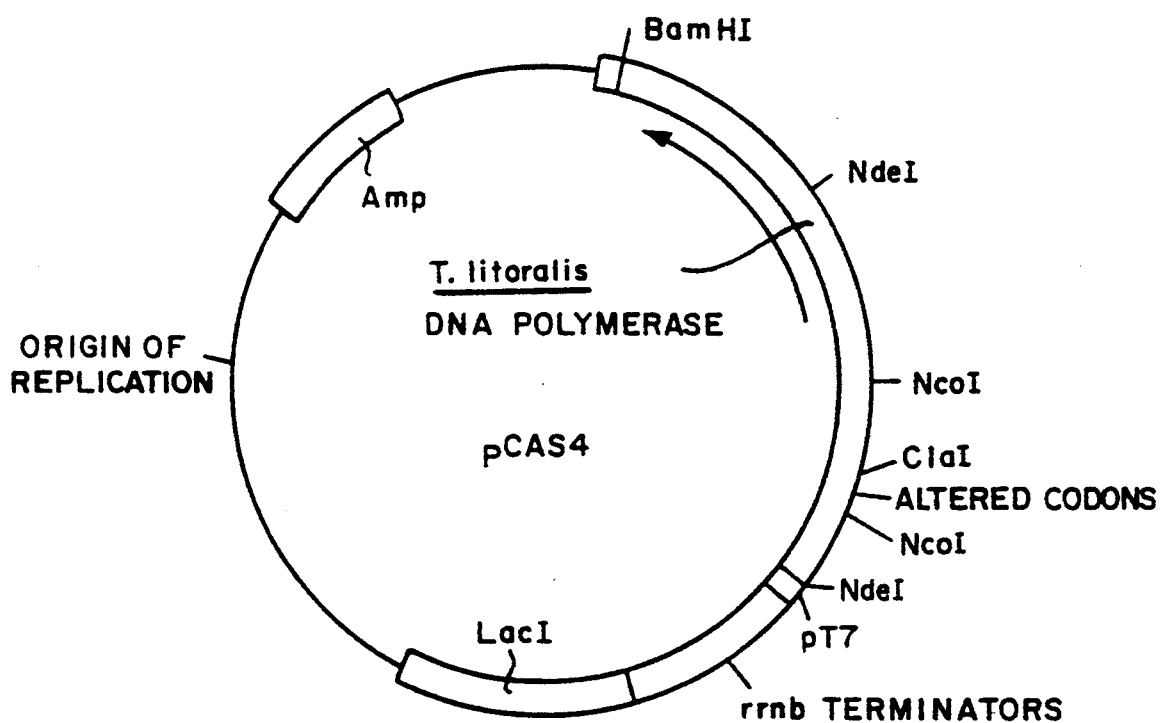
Figure 10:
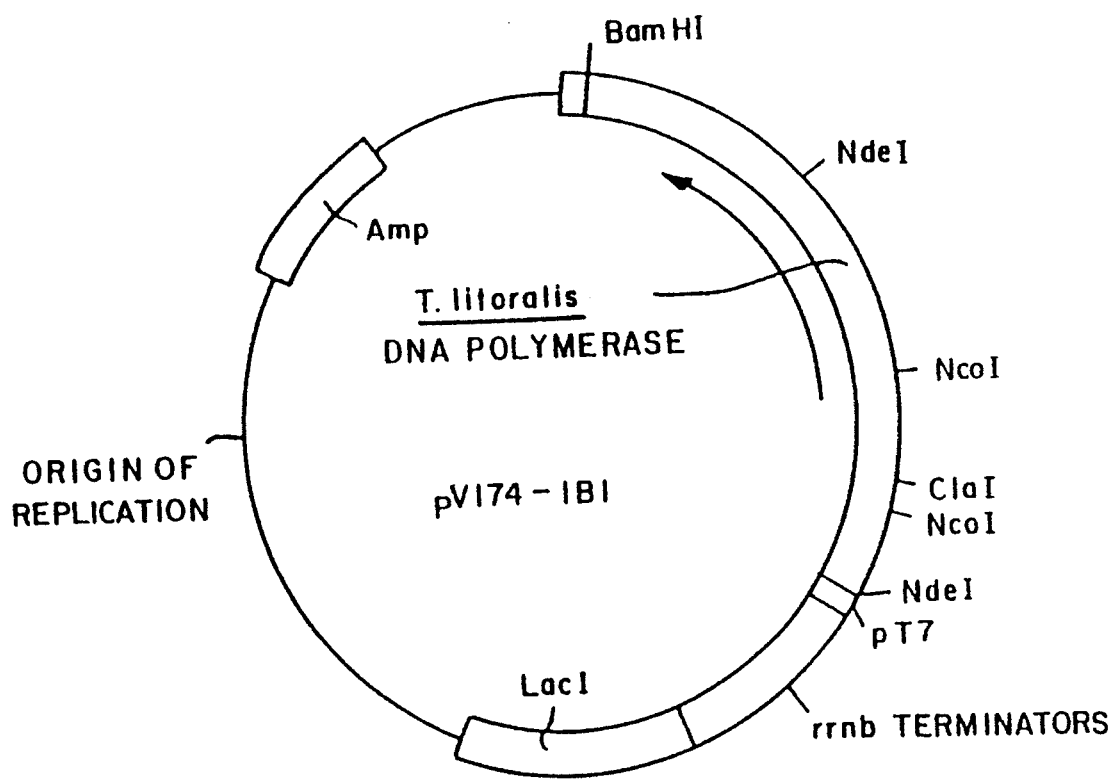
Figure 11:
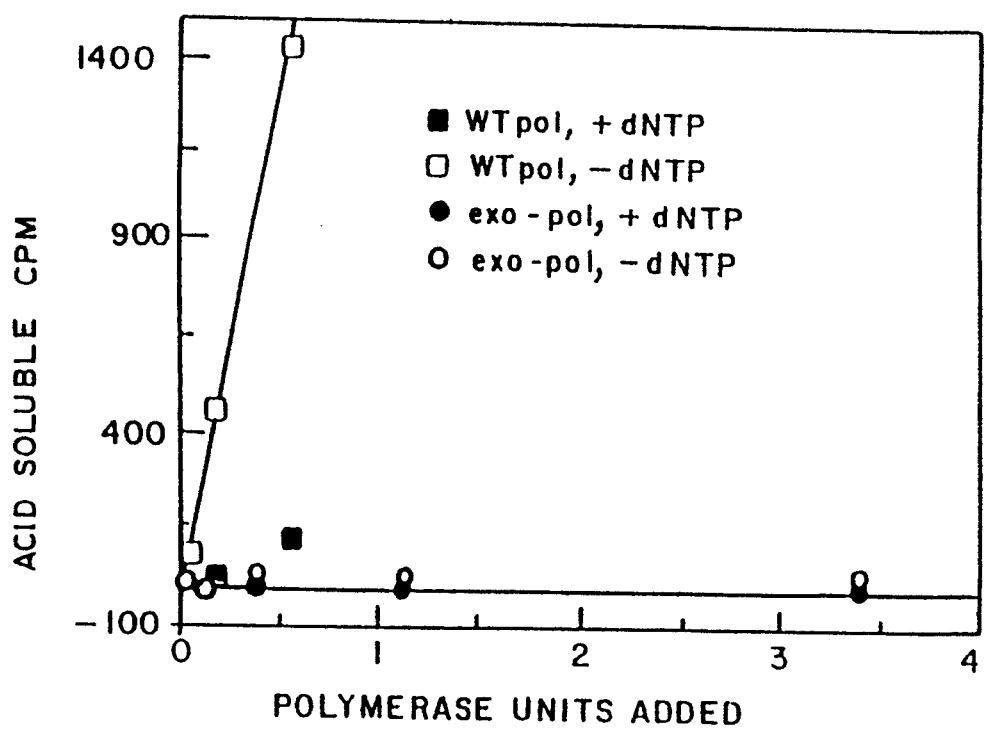
FIG. 11 is a graph illustrating the *T. litoralis* DNA polymerase variant constructed in Example VI lacks detectable 3' to 5' exonuclease activity.

The thermostability or half-life of recombinant *T. litoralis* DNA polymerase purified as described above in Example IV was found to have a biphasic heat inactivation curve at temperatures greater than about 90° C. These two phases were characterized by half-lives of about 5 minutes and 7 hours (FIG. 3B). To provide more consistent behavior at extreme temperatures, an additional purification step may be used to eliminate the more heat sensitive component of the polymerase.

Specifically, the final enzyme preparation of Example IV was heated at 100° C. for 15 minutes then cooled on ice for 30 minutes. Precipitated proteins were removed by centifugation at 12,000 xg for 10 minutes at 4° C. Approximately 20% of the initial polymerase activity was lost in this procedure. The remaining DNA polymerase showed a monophasic heat inactivation profile, with a half-life at 95° C. of about 7 hours. The resulting polymerase also showed kinetic characteristics at 75° C. which were similar to the native enzyme and to the recombinant enzyme prepared in accordance with Example IV.

EXAMPLE VIII

DETERMINATION OF 3'-5' PROOFREADING ACTIVITY

1. Response of *T. litoralis* DNA Polymerase to the Absence or Presence of Deoxynucleotides The levels of exonuclease activities associated with polymerases show very different responses to deoxynucleotides. Nonproofreading 5'-3' exonucleases are stimulated tenfold er greater by concomitant polymerization afforded by the presence of deoxynucleotides, while proofreading 3'-5' exonucleases are inhibited completely by concomitant polymerization. Lehman, I.R. ARB (1967) 36:645.

The *T. litoralis* DNA polymerase or polymerases with well-characterized exonuclease functions (T4 Polymerase, Klenow fragment) were incubated with 1 µg $^3$H-thymidine-labeled double-stranded DNA (10$^5$ CPM/µg) in polymerization buffer (70 mM tris (pH 8.8 at 24° C.), 2 mM MgCl$_2$, 0.1% Triton and 100 µg/ml bovine serum albumin). After an incubation period of three hours (experiment 1) or four hours (experiment 2) at either 70° C. (thermophilic polymerases) or 37° C. (mesophilic polymerases), the exonuclease-hydrolyzed bases were quantified by measuring the acid-soluble radioactively-labeled bases.

As shown in Table 1, the Taq DNA polymerase, with its 5'-3' exonuclease activity, shows stimulation of exonuclease activity when deoxynucleotides were present at 30 uM. However, polymerases with 3'-5' proofreading exonuclease activities, such as the T4 polymerase, Klenow fragment of *E. coli* polymerase I, or the *T. litoralis* DNA polymerase showed the reverse, an inhibitory response to the presence of deoxynucleotides.

The similarity of responses to the presence or absence of deoxynucleotides of the *T. litoralis* DNA polymerase and the well-characterized Klenow fragment of the *E. coli* DNA polymerase is further shown in FIG. No. 4. Twenty units of either polymerase was incubated with 9 μg ³H-thymidine-labeled double-stranded DNA ($10^5$ CPM/μg) in 350 μl polymerization buffer as described above in the presence, or absence of, 30 μM deoxynucleotides. At each time point, 50 μl was removed and the level of acid-soluble radioactively-labeled bases were measured. As FIG. No. 4 documents, the behavior of *T. litoralis* DNA polymerase and the Klenow fragment of *E. coli* DNA polymerase, which contains a well-characterized 3'-5' proofreading exonuclease activity, are very similar.

2. Response of *T. litoralis* DNA Polymerase to Increasing Deoxynucleotide Concentrations Exonuclease activities of polymerases are affected by the level of deoxynucleotides present during polymerization, in as much as these levels affect polymerization. As deoxynucleotide levels are increased towards the Km (Michaelis constant) of the enzyme, the rate of polymerization is increased. For exonuclease functions of polymerases sensitive to the rate of polymerization, changes in exonuclease activity are parallel with increases in deoxynucleotide concentrations. The increase in polymerization rate drastically decreases proofreading 3'-5' exonuclease activity with a concomitant increase in polymerization-dependent 5'-3' exonuclease activity.

The exonuclease function of the *T. litoralis* DNA polymerase was compared to those of well-characterized exonuclease functions of other polymerases as the deoxynucleotide concentration was increased from 10 uM to 100 uM. The exonuclease activity was measured as described in (1) with an incubation period of 30 minutes. As summarized in Table 2, the *T. litoralis* DNA polymerase responded to increases in deoxynucleotide levels similarly to a polymerase known to possess a 3'-5' proofreading exonuclease (Klenow fragment of *E. coli* DNA Pol. I). This

TABLE 2

| | | Acid-Soluble CPM (Exonuclease Activity) | | |
|---|---|---|---|---|
| Amount | Type of DNA Polymerase | 10 uM dNTPS | 100 uM dNTPS | Effect on Hydrolysis with Increasing dNTPS |
| 5 units | Taq Polymerase | 350 | 610 | 1.7X increase |
| 5 units | Klenow fragment of *E. coli* Pol. I | 650 | 300 | 2.2X decrease |
| 5 units | *T. litoralis* Polymerase | 180 | 110 | 1.6X decrease | response was in contradiction to that of a polymerase known not to possess this proofreading function, Taq DNA polymerase. This polymerase responded to an increase in deoxynucleotide levels with an increase in exonuclease function due to its 5'-3' exonuclease activity.

TABLE 1

| Experiment # | Amount | Type of DNA Polymerase | Acid-Soluble CPM (Exonuclease Activities)* | | Effect Upon Adding NTPS |
|---|---|---|---|---|---|
| | | | no dNTPS | 30 uM dNTPS | |
| 1 | 2.5 units | Taq Polymerase | 241 | 1936 | 8X increase |
| | 3 units | T4 Polymerase | *47608 | 6663 | 7X decrease |
| | 10 units | Klenow Fragment of *E. coli* Pol. I | 11272 | 2845 | 4X decrease |
| 2 | 5 units | Taq Polymerase | 338 | 2539 | 8X increase |
| | 5 units | T4 Polymerase | *46001 | 10418 | >4X decrease |
| | 5 units | Klenow Fragment of *E. coli* Pol. I. | 8757 | 408 | 22X decrease |
| | 5 units | *T. litoralis* Polymerase | 8573 | 795 | 11X decrease |

*Nonlinear range of assay

3. Response of *T. litoralis* DNA Polymerase to Alteration from a Balanced Deoxynucleotide State to an Unbalanced State Polymerization is dependent on equal levels of all four deoxynucleotides present during DNA synthesis. If the deoxynucleotide levels are not equal, polymerases have decreased polymerization rates and are more likely to insert incorrect bases. Such conditions greatly increase proofreading 3'-5' exonuclease activities while decreasing 5'-3' exonuclease activities. Lehman, I.R., ARB (1967) 36:645.

The *T. litoralis* DNA polymerase was incubated with both balanced deoxynucleotide levels (30 uM) and two levels of imbalance characterized by dCTP present at 1/10 or 1/100 the level of the other three deoxynucleotides. The response of the *T. litoralis* DNA polymerase was then compared to that of three polymerases possessing either the 3'-5' or the 5'-3' exonuclease functions. All assays were performed as described in (1) except for dCTP concentrations listed below. As seen in Table 3 below, the *T. litoralis* DNA polymerase follows the expected behavior for a proofreading 3'-5' exonuclease-containing polymerase; an imbalance in deoxynucleotide pools increased the exonuclease activity in a similar manner as that of the proofreading polymerases of T4 DNA polymerase or Klenow fragment of *E. coli* DNA polymerase I. In contrast to this response, the exonuclease of the Taq DNA polymerase was not affected until the imbalance was heightened to the point that polymerization was inhibited.

TABLE 3

| | Acid-soluble CPM (Exonuclease Activity) | | | |
|---|---|---|---|---|
| Type of DNA Polymerase (5 units @) | no dNTPS | 30 uM dNTPS | 30 uM/3 uM* | 30 uM/0.3 uM** |
| Taq Polymerase | 338 | 2539 | 2243 | 656 |

TABLE 3-continued

| Type of DNA Polymerase (5 units @) | Acid-soluble CPM (Exonuclease Activity) | | | |
|---|---|---|---|---|
| | no dNTPS | 30 uM dNTPS | 30 uM/3 uM* | 30 uM/0.3 uM** |
| T4 Polymerase | ***46001 | 10418 | ***43850 | ***46585 |
| Klenow Fragment of E. coli Pol. I | 8757 | 408 | 1291 | 1755 |
| T. litoralis Polymerase | 8573 | 795 | 3471 | 3339 |

*3 uM dCTP, 30 uM all other dNTPs
**0.3 uM dctp, 30 uM all other dNTPs
***nonlinear range of assay 4. Directionality of Exonuclease Activity A proofreading exonuclease has a 3'-5' directionality on DNA while nonproofreading exonuclease associated with DNA polymerases have a 5'-3' directionality. To discern the direction of the exonuclease activity of T. litoralis DNA polymerase, the 5' blocked DNA of adenovirus was utilized. Since the 5' end of this DNA is blocked by protein, enzymic activities that are 5'-3' in directionality cannot digest this double-stranded DNA; however, enzymic activities that are 3'-5', such as exonuclease III or proofreading exonuclease-containing polymerases, can digest adenovirus DNA.

Twenty-five units of exonuclease III or 20 units of either T. litoralis DNA polymerase, T4 DNA polymerase (possessing a well characterized 3'-5' exonuclease activity), or Taq DNA polymerase (lacking such an activity) were incubated with 5 μg adenovirus DNA for time periods up to 30 minutes duration at either 37° C. (T4 polymerase and exonuclease III) or 70° C. (Taq polymerase and T. litoralis polymerase) in the presence of 70 mM tris-HCl pH 8.8 at 25° C., 2 mM MgCl$_2$ and 100 μg/ml BSA. At the end of each incubation time period, enzymic activity was stopped by phenol extraction of the adenovirus DNA, followed by Hpat digestion for one hour at 37° C. in 20 mM tris, pH 7.9 at 25° C., 10 mM Magnesium acetate 50 mM potassium acetate and 1 mM DTT. The DNA fragments were subjected to agarose gel electrophoresis and the resulting pattern of time-dependent degradation and subsequent loss of double-stranded DNA fragments were assessed.

The 3'-5' exonuclease activities of exonuclease III, of T. litoralis DNA polymerase and T4 DNA polymerase caused the disappearance of the double-strand DNA fragments originating from the 5' blocked end of the adenovirus DNA, indicating vulnerability of its 3' end. In contrast, the Taq DNA polymerase with its 5'-3' polymerization-dependent exonuclease activity, showed no disappearance of the DNA fragment.

EXAMPLE IX

PERFORMANCE OF T. litoralis DNA POLYMERASE IN THE PCR PROCESS

The ability of the T. litoralis DNA polymerase to perform the polymerase chain reaction (PCR) was also examined. In 100 μl volumes containing the buffer described in Example IV, varying amounts of M13mp18 DNA cut by ClaI digestion, generating 2 fragments of 4355 bp and 2895 bp, were incubated with 200 ng of calf thymus DNA present as carrier DNA to decrease any nonspecific adsorption effects. The forward and reverse primers were present at 1 μM (forward primer=5'd(-CCAGCAAGGCCGATAGTTTGAGTT)3' and the reverse primer=5' d(CGCCAGGGTTTTCCCAGT-CACGAC)3'). These primers flank a 1 kb DNA sequence on the 4355 bp fragment described above, with the sequence representing 14% of the total M13mp18 DNA. Also present were 200 μM each dNTP, 100 μg/ml BSA, 10% DMSO and 2.5 units of either T. aquaticus DNA polymerase (in the presence or absence of 0.5% NP40 and 0.05% Tween 20), or T. litoralis DNA polymerase (in the presence or absence of 0.10% Triton X-100). The initial cycle consisted of 5 min at 95° C., 5 min at 50° C. (during which polymerase and BSA additions were made) and 5 min at 70° C. The segments of each subsequent PCR cycle were the following: 1 min at 93° C., 1 min at 50° C. and 5 min at 70° C. After 0, 13, 23 and 40 cycles, 20 μl amounts of 100 μl volumes were removed and subjected to agarose gel electrophoresis with ethidium bromide present to quantitate the amplification of the 1 kb DNA sequence.

Initial experiments with this target DNA sequence present at 28 ng and 2.8 ng established the ability of the T. litoralis DNA polymerase to catalyze the polymerase chain reaction; yields were comparable or not more than twofold greater than the seen with T. aquaticus DNA polymerase.

However, it was at the lower levels of target DNA sequence, 2.8 femtograms, that differences in polymerase function were most apparent. Under these conditions requiring maximal polymerase stability and/or efficiency at elongation of DNA during each cycle,the T. litoralis DNA polymerase produced greater than fourfold more amplified DNA than that of T. aquaticus DNA polymerase within 23 cycles.

This ability to amplify very small amounts of DNA with fewer cycles is important for many applications of PCR since employing large cycle numbers for amplification is associated with the generation of undesirable artifacts during the PCR process.

EXAMPLE X

PURIFICATION OF RECOMBINANT T. LITORALIS INTRON-ENCODED ENDONUCLEASE

E. coli NEB671 (ATCC No. 68447), grown as described in Example IV, were thawed (70 grams) and suspended in Buffer A containing 200 μg of lysozyme per ml to a final volume of 300 ml. The mixture was incubated at 37° C. for 2 minutes and then 75° C. for 30 minutes. The heated mixture was centrifuged at 22,000 x g for 30 minutes and the supernatant was collected for further purification of the thermostable endonuclease. Since all of the nucleases from E. coli were inactivated by the heat treatment, the preparation at this stage could be used for characterization of the intron-encoded endonuclease. To separate this enzyme from the recombinant T. litoralis DNA polymerase also present in the 75° C. supernatant solution, the solution was passed through a DEAE-sepharose column (5 cm×5 cm, 100 ml bed volume) and washed with 200 ml of Buffer A. Essentially all of the DNA polymerase activity passes through the column while the endonuclease activity sticks. The endonuclease activity was eluted with a one liter linear gradient of NaCl from 0.1M to 0.8 M formed in Buffer A. The endonuclease activity eluted at about 0.4 M NaCl, and was assayed in a buffer containing 10 mM KCl, 20 mM Tris-HCl (pH 8.8 at 24° C.), 10 mM (NH4)4SO4, 10 mM MgSO4, 0.1MgS04, 0.1% Triton X-100 and 1 μg of pBR322 DNA per 0.05 ml of reaction mixture. The reaction mixture was incubated at 75° C. and the extent of DNA cleavage was determined by agarose gel electrophorese. At lower temperatures little or no endonuclease activity was detected. The tubes containing the peak activity were pooled, dialyzed overnight against Buffer A and then applied to phosphocellulose column (2.5 cm×6.5 cm, 32 ml bed volume), washed with Buffer A and the endonuclease activity eluted with a linear gradient of NaCl from 0.1M to 1.5 M formed in Buffer A. The enzyme eluted at about 0.8 M NaCl. Active fractions were pooled and dialyzed overnight against Buffer A and then passed through a HPLC Mono-S column (Pharmacia) and eluted with a linear gradient of NaCl from 0.05 M to 1.0 M. The activity eluted as a single peak and was homogeneous by SDS-PAGE: a single 42–47 kd band was detected by Commasie blue staining and when this band was eluted from the gel and renatured it contained the only endonuclease activity detected on the gel.

The enzyme has preferred cutting sites on various DNAs. When used in vast excess and in Vent polymerase buffer (New England Biolabs, Beverly, Ma.), the enzyme has cutting sites on lambda DNA and 3 sites on pBR322. Two of the rapid sites on pBR322 have been sequenced:

Region including cut site at position 164:

5' TTGGTTATGCCGGTAC TGCCGGCCTCTT 3'
3' AACCAATACGGC CATGACGGCCGGAGAA 5'

Region including cut site at position 2411:

5' TTGAGTGAGCTGATAC CGCTCGCCGCAG 3'
3' AACTCACTCGAC TATGGCGAGCGGCGTC 5'

When IVS2 was deleted from pPR969, the resultant plasmid, pAKK4 (Example XI) now contains a very sensitive fast site at the exon junction:
Region including the cut site at IVS2 junction:

5' GGTTCTTTATGCGGAC* AC/ TGACGGCTTTATG 3'
3' CCAAGAAATACGCC/ TG* TGACTGCCGAAATAC 5'

The astericks denote the boundary between the left exon and the right exon which have been brought together by deletion of IVS2.
Cleavage at the I-Tli I homing site occurs 100-fold more rapidly than at the "star" sites using reaction conditions of 50ram TRIS, (pH 7.9), 10mM MgCl2, 100mM NaCl and I mM DTT at 50° C. Under these conditions, the enzyme cut E. coli DNA 6–10 times. "Star" cleavage is enhance by NH4 (10 mM), higher temperatures (70–80° C.), and higher pH (8.8–10).

Thus, the endonuclease from T. litoralis resembles other intron encoded endonucleases reported in that there is often a four base 3' extension at the cut site and there can be degeneracy in the recognition sequence.

The cut site in the intron minus gene is referred to as the homing site of the intron encoded endonuclease. It is believed in the art that the intron encoded endonuclease recognizes its cut site in the gene lacking the intron, and that the cutting of that DNA by the endonuclease leads to insertion of the intron at the homing site.

The thermostable endonuclease of the present invention can be used in genetic manipulation techniques where such activity is desired.

EXAMPLE XI

Construction of T. litoralis DNA Polymerase Expression Vectors with a Deleted IVS2

Analysis of the deduced amino acid sequence of the T. litoralis gene in comparison to other alpha class DNA polymerases and to the endonuclease in the 1170 bp intervening sequence suggested that this intron interrupted the alpha polymeras Region I. If the first 3 amino acids preceding the endonuclease (Tyr Ala Asp) were joined to the Thr at aa 1472, then a good consensus Region I would be established (where underlined residues indicate identity):

| Region I: | TYR | GLY | ASP | THR | ASP | SER |
|---|---|---|---|---|---|---|
| Left junction: | TYR | ALA | ASP | SER | VAL | SER |
| Right junction: | VAL | HIS | ASN | THR | ASP | GLY |
| Vent Pol Region I: | TYR | ALA | ASP | THR | ASP | GLY |

To facilitate this construction, a ScaI site was created in the PCR primers by changing the codon usage for Lys 1076 and Val 1077 as follows:

| Amino acids: | PHE | LYS | VAL | LEU | TYR | ALA | ASP |
|---|---|---|---|---|---|---|---|
| Original sequence: | TTT | AAG | GTT | CTT | | | |
| Altered sequence: | TTT | AAA | GTA | CTT | | | |
| Sca I site: | | A | GTA | CT | | | |

The expression plasmid pAKK4 was created in a three-way ligation derived from the following components:

1) An about 7959 bp fragment of pPR96g was derived by cleavage with HindIII and EcoRI. 9 μg of pPR969 DNA was incubated with 1X NEBuffer 2 in a total volume of 0.1 ml with 40 units of HindIII endonuclease and 40 units of EcoRI endonuclease for 1 hour at 37° C. Cleavage products were separated on a 0.7% GTG grade agarose gel (FMC) run in Tris Borate EDTA buffer. The appropriate band, about 8 kbp, was isolated by electroelution using an Elutrap elution apparatus (Schleicher and Schuell) using the manufacturer's recommended running conditions. Following elution, the fragment was concentrated by ethanol precipitation and the recovery quantified by comparison with known weight standards on agarose gel electrophoresis.

2) An about 638 bp fragment with ScaI and EcoRI termini derived from a PCR product. The reaction mixture contained 1X NEB Vent Polymerase Buffer, 0.1 mg/ml bovine serum alumen, 0.2 mM dNTPs (equimolar, each nucleotide), 0.9 μg/ml pV174.181 plasmid DNA template, and 0.01A26-0U/ml of primer 72–150 (5'ATAAAGTACTT-TAAAGCCGAACTTTTCCTCTA3') and primer "JACK" (5'CGGCGCATATGATACT-GGACACTGATTAC3'). 0.1 ml of the reaction mix was placed into each of five tubes, and the samples heated to 95° C. for 3–5 minutes in a Perkin-Elmer Thermocycler. 1U of Vent DNA polymerase was added to each reaction tube, and 15 cycles were run on the thermocycler consisting of 94° C.- 0.5 minutes, 50° C. - 0.5 minutes, and 72° C.

- 2 minutes. The samples were pooled, phenol extracted and ethanol precipitated. The sample was resuspended in 50 μl Tris-EDTA buffer and mixed with 40 μl of dH20, 10 μl of 10X NEBuffer 3, 60 units of ScaI endonuclease and 60 units of EcoRI endonuclease. After incubation at 37° C. for 1.75 h, the reaction products were separated on a 1.5% agarose gel and the ca. 638 bp fragment was electroeluted, and quantified as described above.

3) An about 358 bp fragment with HindIII and Scai termini derived from a PCR product. The reaction mixture contained 1 X NEB Vent Polymerase Buffer, 0.1 mg/ml bovine serum albumin, 0.2 mM dNTPs (equimolar, each nucleotide), 0.9 μg/ml pV174.181 plasmid DNA template, and 0.02 $A_{260}$ oU/ml of primer 698 (5'GAGACTCGC-GGAGAAACTTGGACT3') and primer 73–143 (5'TACAGTACTTTATGCGGACACT-GACGGCTTTTATGCCAC3'). 0.1 ml of the reaction mix was placed into each of five tubes, and the samples heated to 95° C. for 3–5 minutes in a Perkin-Elmer Thermocycler. 1 U of Vent DNA polymerase was added to each reaction tube, and 20 cycles were run on the thermocycler consisting of 94° C. - 0.5 minutes, 50° C. - 0.5 minutes, and 72° C. - 1 minute. The samples were pooled, phenol extracted and ethanol precipitated. The sample was resuspended in 50 μl Tris-EDTA buffer and cleaved with HindIII and ScaI endonucleases. The reaction products were separated on a 1.5% agarose gel and the 358 bp fragment was electroeluted, and quantified as described above.

The ligation reaction contained approximately 1 μg/ml of the pPR969 fragment described above, 0.8 μg/ml of the 638 bp fragment described above, 0.4 μg/ml of the 358 bp fragment described above, 1X NEB ligation buffer and 100,000 units/ml T4 DNA ligase. Ligation occurred at 16° C. for 5 hours Correctly constructed recombinants were identified by the ScaI digestion pattern, and transformed into BL21(DE3) plysS to screen for inducible activity, as described above. Two such isolates, pAKK4 and pAKK15 were used in subsequent studies. These two isolates appear to be identical, although they were isolated from independent isolates.

Expression from the new construct pAKK4 appears to yield 3-10-fold more active *T. litoralis* DNA polymerase than pPR969 without expression of the endonuclease from the 1170 bp intron.

An expression vector for production of the exonuclease deficient variant of the *T. litoralis* polymerase was constructed by replacing a 1417 bp ClaI-SphI fragment from pAKK15 with an analogous 1417 bp fragment from pCBA1, the original exonuclease-deficient *T. litoralis* DNA polymerase construct. One such recombinant was named pAKM8 and was characterized further.

EXAMPLE XII

PURIFICATION OF A THERMOSTABLE DNA POLYMERASE FROM PYROCOCCUS SPECIES

Pyrococcus sp. strain GB-D (ATCC No. 55239) was grown in the media described by Belkin, et al., supra, containing 10 g/1 of elemental sulfur in 8 one liter bottles at 94° C. for two days. The cells were cooled to room temperature, separated from unused sulfur by decanting and collected by centrifugation and stored at −70° C. The yield of cells was 1.4 g per liter.

11.5 g of cells obtained as described above, were suspended in 28 ml of buffer A (10 mM KP04 buffer, pH 7.4; 0.1 mM EDTA, 1.0 mM beta-mercaptoethanol) containing 0.1 M NaCl and sonicated for 5 minutes at 4° C.. The lysate was centrifuged at 15,000 g for 30 minutes at 4° C. The supernatant solution was passed through a 18 ml Affigel blue column (Biorad). The column was then washed with 50 ml of buffer A containing 0.1 M NaCl. The column was eluted with a 300 ml linear gradient from 0.1 to 2.0 M NaCl in buffer A. The DNA polymerase eluted as a single peak at approximately 1.3 M NaCl and represented 90% of the activity applied. The peak activity of DNA polymerase (25 ml) was dialyzed against I liter of buffer A containing 100 mM NaCl, and then applied to 15 ml Phosphocellulose column, equilibrated with buffer A containing 100 mM NaCl. The column was washed with 50 ml of buffer A containing 100 mM NaCl, and the enzyme activity was eluted with 200 ml linear gradient of 0.1 to 1.0 M NaCl in buffer A. The activity eluted as a single peak at 0.6 M NaCl and represented 70% of the activity applied. The pooled activity (42 ml) was dialyzed against 500 ml of buffer A and applied to a 25 ml DEAE column. The column was washed with 50 ml of buffer A containing 0.1 M NaCl, and two-thirds of the enzyme activity passed through the column. The active fractions were pooled (30 ml) and applied to an 1.0 ml HPLC mono-S column (Pharmacia) and eluted with a 100 ml linear gradient in buffer A from 0.05 to 1.0 M NaCl. The activity eluted as a single peak at 0.22 M NaCl and represented 80% of the activity applied.

Purified *Pyrococcus sp.* polymerase was electrophoresed in SDS 10–20% polyacrylamide gel and stained with either Coomassie Blue or the colloidal stain (ISS Problue) previously described to detect protein. A faintly staining protein band was seen at about 92,000 to 97,000 daltons; this molecular weight determination was obtained by comparison on the same gel to the migration of the following marker proteins (Bethesda Research Laboratories): myosin, 200,000 daltons; phosphorylase B, 97,400 daltons; BSA, 68,000 daltons; ovalbumin, 43,000 daltons, carbonic anhydrase 29,000 daltons; b-lactoglobulin, 18,400 daltons; lysoyzme 14,300 daltons.

EXAMPLE XIII

CLONING OF PYROCOCCUS SPECIES DNA POLYMERASE GENE

Cross hybridization of a *Pyrococcus* genomic DNA library using radioactive probes prepared from the DNA polymerase gene of *T. litoralis* allowed for the identification and isolation of a DNA encoding the *Pyrococcus* DNA polymerase. This was accomplished as set forth below.

In order to determine which restriction enzymes would be most useful in preparation of the Pyrococcus genomic library, *Pyrococcus sp.* DNA was cut to completion with Eco RI, BamHI and HindIII. This DNA was subject to agarose gel electrophoresis (FIG. 13A) and Southern hybridization (FIG. 138) using a DNA probe prepared as follows. A reaction mixture containing 1 μg of the first EcoRI fragment of the *T. litoralis* DNA polymerase gene (bp 1-1274, obtainable from bacteriophage NEB#618, ATCC No. 40794) as a template in a commercial random priming kit (New England Biolabs, Inc.) was incubated for 1 hour at 37° C. to produce a DNA probe of high specific activity. The probe was hybridized to *Pyrococcus sp.* DNA prepared above under moderately stringent conditions (Hybridization: overnight at 50° C., 4X SET, 0.1M sodium phosphate, pH 7, 0.1% Na pyrophosphate, 0.1% SDS, 1X Denhardts solution; Wash Conditions: wash 3×20-30 min. 45° C., 0.1X SET, 0.1M sodium phosphate, (pH 1), 0.1% Na pyrophosphate, 0.1% SDS. Maniatis, et al., supra). A single major band at about 5 Kb was detected in BamH I cut *Pyrococcus* DNA. EcoR I and Hind III gave multiple bands with this probe, indicating that these enzymes cut within the *Pyrococcus* polymerase gene.

Based on these results, a BamHI genomic library was constructed using the phage vector λDASH (Stratagene). Partial and complete BamHI digests of *Pyrococcus* DNA were prepared. A mixture of the partial and completely BamHI digested DNA was ligated into the BamHI site of λDASH. The ligation mixture was packaged using Gigapack Gold (Stratagene) according to manufacturer's instructions and plated on *E. coli* ER1458. The packaged phage library contained $1 \times 10^6$ phage per ml.

$^{32}$P-labelled DNA probes of the 3 fragments (bp 1-1274, 1656-2660 and 3069-3737) of the *T. litoralis* DNA polymerase gene (obtainable from NEB#619, ATCC No. 40795) were prepared using a random primer kit (New England Biolabs, Inc.) . The probes were used according to the method of Benton & Davis (Maniatis, et al. supra) to screen the *Pyrococcus* genomic library using hybridization conditions described above. About one per cent of the plaques were positive and ten positive plaques were picked and purified by reinfection and replating 3 times (until 90-100% of the plaques were positive for each isolate). Large amounts of phage were prepared from each isolate and used to infect *E. coli* cultures. Specifically, plate lysates (Maniatis et al. supre) of phage were prepared from each isolate and used to infect *E. coli* cells. 0.1 ml of each plate lysate was mixed with *E. coli* with 0.2 ml of cells ($OD_{600}=2$). The bacterial cells were harvested just before lysis and suspended in 0.05 M NaCl, 0.01 M Tris (pH 8.0), 0.1 mM EDTA, 0.1% Triton X-100 and 200 µg/ml lysozyme (3 volumes per volume of cells) and heated to 37° C. for about 1 minute or until cell lysis occurred. The lysed extracts were immediately heated at 75° C. for 30 minutes, centrifuged and the supernatant solution assayed for heat stable DNA polymerase activity, according to the method described above. Three of the ten isolates showed significant polymerase activity and the clone (Bg) showing the most activity was investigated further.

Figure 14:
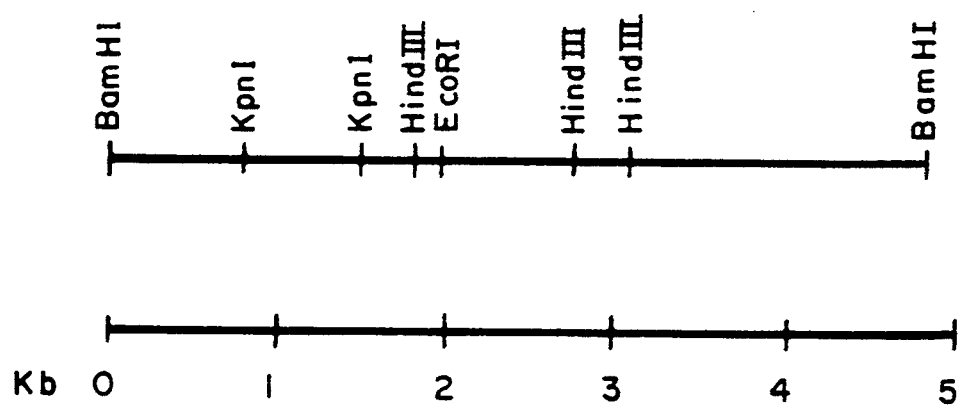
FIG. 14 is a restriction site map of the 4.8 Kb BamH I fragment containing the gene containing the Pyrococcus sp. DNA polymerase in the pUC19 plasmid of *E. coli* 2207 (NEB#720).

The phage DNA was isolated from B9 and the insert DNA was examined by restriction enzyme digestion. Digestion with Sal I gave the expected two arms of λDASH plus a 15 Kb insert. Digestion with BamH I gave the two arms of λDASH plus three insert fragments of 7, 4.8 and 3 Kb. Each of these fragments were purified by agerose gel electrophoresis, eluted and ligated into the BamH I site of pUC19. The ligation mixture was used to transform *E. coli* ER2207 which gives white colonies when plasmids contain an insert and blue colonies with no inserts on indicator agar media (X-gal plus IPTG). No white transformants were obtained with the 7 Kb fragment. Three whites and twenty-seven blue transformants were obtained with the 4.8 Kb fragment and twenty white and twenty-one blue transformants were obtained with the 3 Kb fragment. All three 4.8 Kb white colony transformants expressed heat stable DNA polymerase activity. None of the transformants with the 3 Kb fragment expressed heat stable polymerase activity. The three clones carrying the 4.8 Kb *Pyrococcus* DNA fragment all had about the same specific activity for heat stable DNA polymerase and one was picked for further study (NEB#720) . This clone designated NEB#720 was deposited with the American Type Culture Collection on Oct. 1, 1991 and bears ATCC No. 68723. A restriction endonuclease mad of the 4.8 Kb BamH I fragment containing the *Pyrococcus sp.* DNA polymerase gene is shown in FIG. 14. A partial DNA nucleotide sequence coding for *Pyrococcus sp.* DNA polymerase (NEB720) is set forth in FIG. 18, including the start of the polymerase gene at bp 363 and a portion of the intervening nucleotide sequence (bp 1839-3420). NEB#720 yielded 1700 units of DNA polymerase activity per gram of cells and was used for the large scale preparation of this enzyme.

A portion of the *Pyrococcus sp.* DNA polymerase clone has been sequenced (FIG. 18, bp 1-3420). The sequence of the *Pyrococcus sp.* DNA polymerase is very similar to the *T. litoralis* DNA polymerase at both the DNA and protein level (similarity calculated using the GCG Bestfit Program, Smith and Waterman, *Advances in Applied Mathmatics*, 2:482 (1981)). Overall, the genes are 66% identical, with 69% identity in the mature DNA polymerase amino termini regions (bp 363-1838 in *Pyrococcus sp.* DNA polymerase) and 63% identical in the portion of IVS1 sequenced to date (bp 1839-3420 in *Pyrococcus sp.* DNA polymerase). The upstream regions (bp 1-362 in *Pyrococcus sp.* DNA polymerase, FIG. 18 and bp 1-290 in *T. litoralis* DNA polymerase, FIG. 6) show no similarity according to the Bestfit Program.

Similarity at the protein level is even higher. In the 1019 amino acid *Pyrococcus sp.* DNA polymerase coding region, the two polymerases have 83% similarity and 68% identity (FIG. 19). When broken down into the mature polymerase amino terminus and IVSI, the polymerase coding exons are more similar than the intervening sequence, with the mature polymerase amino termini (aa 1-492 in *Pyrococcus sp.* DNA polymerase) being 89% similar, and 78% identical, and IVS1 (aa 493-1019 in *Pyrococcus sp.* DNA polymerase) being 78% similar and 60% identical.

EXAMPLE XIV

ARCHAEBACTERIA DNA POLYMERASE SIMILARITIES AT THE DNA LEVEL

The degree of cross-hybridization between the *T. litoralis* DNA Polymerase gene and the DNA polymerase genes from 3 other thermophyllic archaebacteria and from Taq DNA was assessed by Southern blot hybridization (Maniatis, supra). Chromosomal DNA from *T. litoralis* and *Pyrococcus sp.* (Strain GB-D), from a Balanced Deoxynucleotide State to an Unbalanced State *T.aquaticus,* and two other Pyrococcus strains, G-1-J and G-1-H, were cleaved with either EcoRI or BamHI. 5 µg of each DNA was incubated with 1x NEBuffer (EcoRI buffer for EcoRI endonuclease and BamHI buffer+1X BSA for BamHI endonuclease) in a total volume of 60 µl with 20 units of EcoRI endonuclease or 20 units of BamHI endonuclease for 2 hours at 37° C. Four quadruplicate 0.75 µg samples of each of the cleaved DNAs were loaded and run on a 1% agarose (SeaKem LE) gel in Tris Acetate EDTA buffer (Maniatis, *supra*). The gel was stained with Ethidium Bromide (1 μg/ml) for 20 minutes at room temperature and a photograph taken with a ruler besides the gel.

The DNA was transferred from the gel onto nitrocellulose paper using the method developed by Southern (Maniatis supra). Nitrocellulose filter paper (0.45 μm) was cut to the size of the gel and soaked in 200ml of 6x SSC (0.9M NaCl, 0.09M Sodium Citrate) for greater than 1 hour at 37° C. Meanwhile, the gel was incubated for 15 minutes in 200ml of 0.25M Hydrochloric acid at room temperature, then rinsed with distilled water. The gel was then incubated for 30 minutes in 200ml 0.5M Sodium Hydroxide, 1M Sodium Chloride at room temperature, then rinsed with distilled water. The gel was then incubated for 30 minutes in 200-mls 1M Tris HCl, pH7.5, 3M Sodium Chloride at room temperature. Transfer of the DNA from the gel onto the nitrocellulose was carried out at 4° C. in IBX SSC (2.7M Sodium Chloride, 0.27M Sodium Citrate), 1M Ammonium Acetate. After 6 hours the nitrocellulose was removed and washed in 1x SSC (0.15M Sodium Chloride and 0.015M Sodium Citrate) for 30 seconds. The nitrocellulose filter was air dried and then vacuum dried at 80° C. for a further 2 hours and then stored at room temperature.

Figure 15:
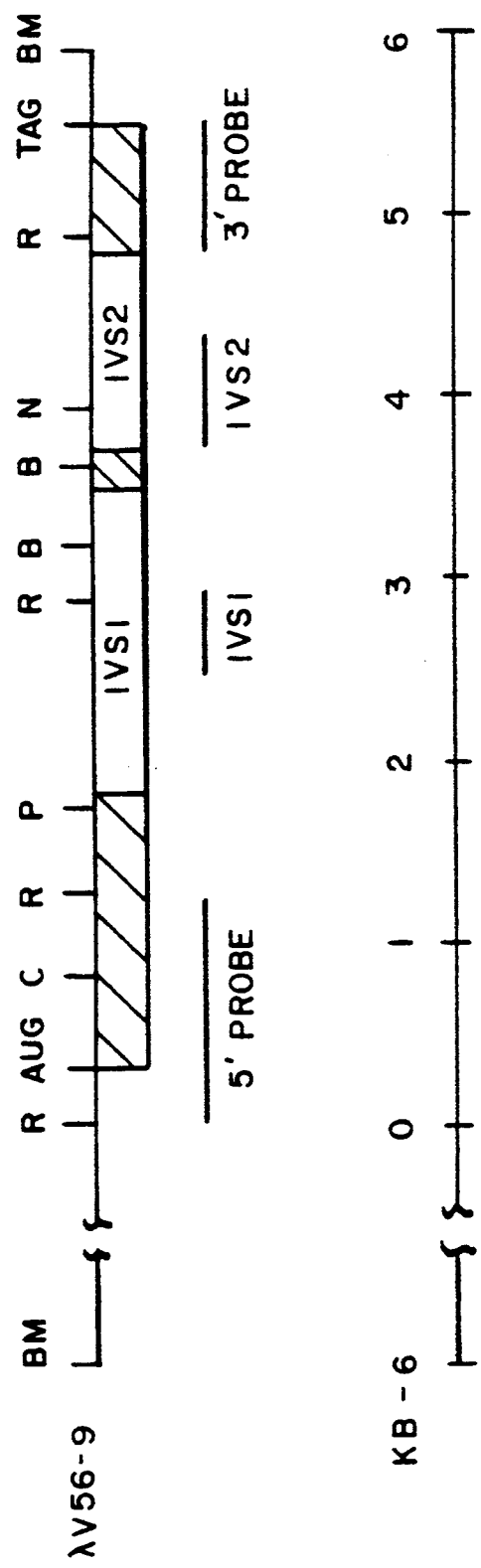
FIG. 15 illustrates the probes used to analyze the similarity of DNA for other target archaebacteria 5' polymerase coding region probe: bp 1-1274; IVS 1 probe: bp 2448-2882; IVS 2 probe: bp 3666-4242; 3' polymerase coding region probe: bp 4718-5437.
Figure 16A:
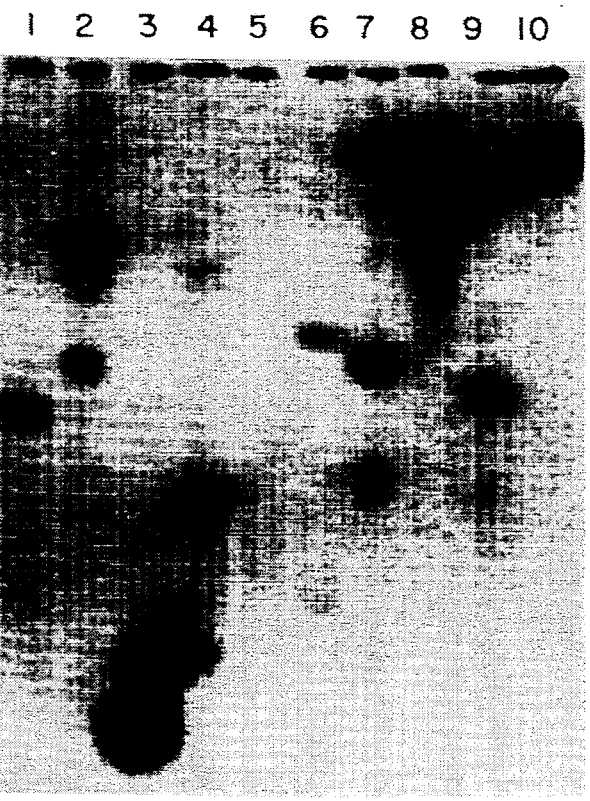
FIGS. 16A–16D are autoradio-graphs of quadruplicate Southern blots described in Example XIV illustrating the hybridization of probes to *T. litoralis* and *Pyrococcus sp.* DNA but not to *T. aquaticus* DNA.
Figure 16B:
Figures 1, 16C:
Figures 2, 16C:
Figures 1, 16D:
Figures 2, 16D:

Four gel purified fragments of T. litoralis DNA polymerase DNA, (1.3 kb Eco RI fragment from bp 1–1274 representing the 5' polymerase coding region; bp 4718–5437, representing the 3' polymerase coding region; bp 2448–2882, representing part of IVS1; and bp 3666–4242, representing part of IVS2, FIGS. 6 and 15) were radiolabelled using the New England Biolabs Random Primer Kit. 100ng of the above template DNAs, each in a volume of 35.5 μl, were boiled for 5 minutes in a boiling water bath and then cooled on ice for 5 minutes and spun down. The template DNAs were incubated with 1X labelling buffer (includes random hexanucleotides), 1/10 volume dNTP mix, 25 μCi $\alpha^{32}P$ dCTP and 5 units DNA Polymerase I-Klenow fragment in a total volume of 50 μl for 1 hour at 37° C. The reactions were stopped with 0.018M EDTA. The probes were purified using an Elutip minicolumn (Schleicher and Schuell) following the manufacturers recommended elution conditions. The total number of counts were calculated for all purified probes. The 1.3 kb Eco RI fragment probe (bp 1–1274) yielded $24 \times 10^6$cpm, the 3' polymerase probe (bp 4718–5436) yielded $22 \times 10^6$cpm, the IVS1 probe yielded $54 \times 10^6$cpm, and the IVS2 probe yielded $47 \times 10^6$cpm.

Hybridization was carried out as follows (Maniatis supra). The nitrocellulose filter was incubated for 30 minutes in 5mls prehybridization buffer (0.75M Sodium Chloride, 0.15M Tris, 10mM EDTA, 0.1% Sodium Pyrophosphate, 0.1% Sodium Lauryl Sulphate, 0.2% Bovine Serum Albumin, 0.2% Ficoll 400, 0.2% PVP and 100 μg/ml boiled calf thymus DNA) at 50° C. Each nitrocellulose filter was then placed in separate bags with 5mls hybridation buffer (as above except 0.03% Bovine serum albumin, 0.03% Ficoll 400, and 0.03% PVP). Each section was hybridized with $22-25 \times 10^6$cpm of denatured probe overnight at 50° C.

The nitrocellulose filters were removed from the bags and incubated 3 × 30 minutes with 0.1X SET Wash (15mM NaCl, 3mM Tris base, 0.2mM EDTA, 0.1% SDS, 0.1% Sodium Pyrophosphate and 0.1M Phosphate Buffer) at 45° C. The filters were kept moist, wrapped in Saran Wrap and exposed to X-ray film for various times ranging from 4 hours to 3 days.

The results are shown in FIG. 16. In FIG. 16, parts A through D are autoradiographs of quadruplicate Southern blots. Lanes 1–5, DNA cut with EcoRI. Lanes 6–10, DNA cut with BamHI. Lanes 1 & 6, Pyrococcus sp. G-1-J DNA; Lanes 2 & 7, Pyrococcus sp. G-1-H DNA; Lanes 3 & 8, T. litoralis DNA; Lanes 4 and 9, Pyrococcus sp. GB-0 DNA, Lanes 5 & 10, T. aquaticus DNA. The hybridization probes are as follows: part A, 5' coding region of T. litoralis DNA polymerase gene, bp 1–1274; part B, 3' coding region of T. litoralis DNA polymerase gene, bp 4718–5437; Part C, partial IVS2 probe, bp 3666–4242; Part D, partial IVS1 probe, bp 2448–2882. The upper and lower panels of parts C and D represent shorter and longer exposures, respectfully, of the same blots.

None of the 4 probes hybridized to Taq DNA. Both polymerase coding region probes hybridize to specific bands in all Thermococcus and Pyrococcus DNAs, but not Taq DNA. Good signals were obtained with both probes indicating strong conservation of both the amino and carboxy terminal ends of the T. litoralis DNA Polymerase coding region. The amino terminal regions of T. litoralis and Pyrococcus sp. GB-D are about 69% identical (see, e.g. FIGS. 6 and 18) and very similar at the protein level (FIG. 19). The IVS1 probe hybridized strongly to T. litoralis and Pyrococcus sp. GB-D DNAs (about 63% identical over a 1582 bp region) and weakly to Pyrococcus sp. G-1-H DNA. The IVS2 probe hybridized strongly to T. litoralis DNA and weakly to Pyrococcus sp. G-1-H DNA.

EXAMPLE XV

ARCHAEBACTERIA DNA POLYMERASE SIMILARITIES AT THE ANTIBODY LEVEL

Pellets from I ml cultures of T. litoralis, and Pyrococcus strains were resuspended in 100 μl Urea lysis buffer (4M Urea, 0.12M Tris, 4% Sodium Lauryl Sulphate, 10% β-mercaptoethanol, 20% glycerol and 0.002% Bromophenol Blue) and boiled for 3 minutes. The boiled samples were sheared with 25G5/8 needle to reduce the viscosity of the samples. Duplicate 10 μl samples of T. litoralis, and Pyrococcus strains G-1-J and G-1-H, and also samples of purified Taq DNA polymerase, E. coli DNA polymerase and purified DNA polymerase from Pyrococcus sp. (GB-D) were loaded onto 10–20% SDS-PAGE gels and run in Protein Running Buffer (0.1% Sodium Lauryl Sulphate, 0.19M Glycine, and 0.025M Tris Base). Nitrocellulose filters (45μm) were soaked in distilled water for 5 minutes and then soaked in Transfer buffer (0.15% ethanolamine, 20mM Glycine and 20% Methanol) for 30 minutes. The protein on the gels were electroeluted (30 volts, overnight at 4° C.) onto the nitrocellulose filters in Transfer buffer (Towbin, et al. PNAS (1979) 76:4350–4354).

Figures 17A, 17B:
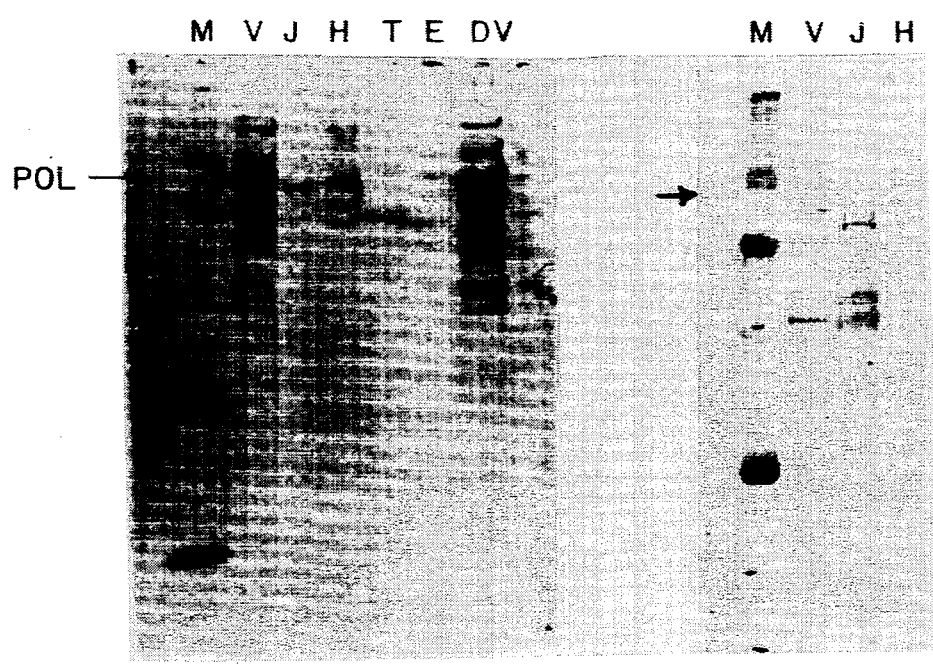
FIG. 17A is a Western blot of crude lysates from *T. litoralis* (V), *Pyrococcus sp.* G-I-J (J), *Pyrococcus sp.* G-I-H (H), or purified polymerase from *Pyrococcus species* GB-D (DV), *T. aquaticus* (T) or *E. coli* (E) reactive with antibody purified anti-Vent DNA polymerase antibody. M represents the marker proteins. The arrow indicates the position of the *T. litoralis* and *Pyrococcus* species DNA polymerase proteins.
FIG. 17B is a Western blot of crude lysates as indicated in FIG. 17A reactive with affinity purified anti-Taq DNA polymerase antibody. The reactivity is to background proteins and not to the DNA polymerases as seen in FIG. 17A.

The nitrocellulose was removed, marked with a ball point pen and washed for 5 minutes in TBSTT (20mM Tris, 150mM Sodium Chloride, 0.2% Tween 20, and 0.05% Triton X-100). The filters were blocked for 30 minutes in TBSTT +3% nonfat dry milk (Carnation), and washed 3×3 minutes in TBSTT. The anti-T. litoralis DNA polymerase antisera was raised against a partially purified native DNA polymerase preparation. T. litoralis DNA polymerase specific sera was prepared by affinity purification on Western blot strips of purified native enzyme (Beall et al., J. Immunological Methods 86:217–233 (1983)). Affinity purified anti-T. litoralis DNA polymerase mouse antibody (V76−2+3) and monoclonal anti-Taq polymerase antibody (diluted 1:100 in TBSTT) were added separately to each nitrocellulose filter for 5 hours at room temperature, The filers were washed 3×3 minutes with TBSTT and then reacted with a 1:7500 dilution of anti-mouse secondary antibody conjugated with alkaline phosphatase (Promega) in TBSTT for 1 hour at room temperature. The nitrocellulose filter was developed with NBT/BCIP as instructed by the manufacturers (Peromega). The results using Taq monoclonal are shown in FIG. 17. FIG. 17 is a Western blot of crude lysates from *T. litoralis* (V), *Prococcus sp.* G-1-J (J), and *Pyrococcus sp.* G-1-H (H), or purified polymerases from *Pyrococcus sp.* GB-D (DV), *T. aquaticus* (T) or *E. coli* (E) reacted with affinity purified anit-*T. litoralis* DNA Polymerase antibody in Part A or anti-Taq DNA polymerase monoclonal antibody in Part B. The arrow indicates the position of the *T. litoralis* and *Pyrococcus sp.* DNA Polymarase proteins. The reactivity in Part B is to background proteins and not to the DNA polymerases as seen in part A.

monoclonal antibody specific to Taq DNA polymerase does not cross-react with protein from the pi Pyrococcus and *Thermococcus* strains tested.

However, the 90–95,000 dalton DNA polymerase proteins from *T. litoralis* and the 3 *Pyrococcus* strains reacted with the affinity purified anit-*T. litoralis* DNA polymerase antibody. This is not surprising, considering he high degree of both similarity and identify between *T. litoralis* and *Pyrococcus sp.* GB-D DNA polymerases (FIG. 19).

FIG. 19 is a comparison of a portion of the deduced amino acid sequences of recombinant *T. litoralis* and the partial sequence of recombinant *Pyrococcus sp.* DNA polymerase. The p*Pyrococcus* DNA polymerase deduced amino acid is listed on the upper line, and the deduced amino acid sequence of recombinant *T. litoralis* DNA polymerase is listed on the lower line. Identifies are indicated by vertical lines, similarities are indicated by 1 or 2 dots, non conserved substitutions are indicated by blank spaces between the two sequences.

EXAMPLE XVI

In order to obtain recombinant thermostable DNA polymerase from a target archaebacterium, several basic approaches to cloning the target DNA polymerase gene can be followed. Initially, one attempts to determine immunologically whether the new polymerase is a member of the Pol α or Pol I family by Western blot analysis of purified polymerase (although crude polymerase lysates may work with reduced sensitivity) using anti-Taq DNA polymerase or anti-*T. litoralis* DNA polymerase sera, as described in Example XV of this invention (FIG. 17). If the new polymerase reacts with anti-Taq Polymerase monoclonal, then it probably cannot be easily cloned using reagents generated from *T. litoralis* DNA Polymerase. If the new polymerase cross-reacts with anti-*T. litoralis* sera, then one should be able to clone it with the following procedures. If the new polymerase fails to react with either sera, then the experiment is considered inconclusive and one should go onto the next step, DNA cross-hybridization.

Optimum probes and DNA hybridization conditions must be experimentally determined for each new organism. At the same time, various restriction digests of DNA from the new organism are tested in order to find enzymes which yield fragments which hybridize to the *T. litoralis* probe and are large enough to encode the new polymerase.

Probe selection can vary with respect to size and regions of the *T. litoralis* DNA Polymerase gene. Optimum probes can be determined by performing test Southern blots as described below with large or small DNA fragments, or even oligomers. One could select probes that are totally from within the IVS sequences to look for the presence of IVSs in new archaebacterium DNA polymerase genes, or probes could be limited to mature polymerase coding regions. Using the entire *T. litoralis* DNA Polymerase gene region as the probe has several advantages and disadvantages. The major disadvantage is that the larger the probe, the more likely to yield spurious hybridization at very low stringency. Among the advantages of using larger probes are (1) they are more likely to cross-hybridize to another polymerase which may have diverged greatly from the *T. litoralis* DNA Polymerase gene in one small portion of the polymerase, and (2) they are more likely to-detect internal restriction sites in the new polymerase gene since the probe spans the amino- and carboxy-termini of the *T. litoralis* DNA Polymerase gene. It is important at the initial stages of probing to use several restriction enzymes to cleave the DNA from the new archaebacterium to find one or more enzymes which yield preferably one, or possibly 2 bands, which hybridize to the *T. litoralis* DNA Polymerase probe and which are large enough to encode the new polymerase. The minimum coding sequence required for the new polymerase can be estimated from the size of the new polymerase determined by Western blots (assuming a factor for IVSs, if desired) or, by guessing at greater than 4 KB as a first approximation. Maximum fragment size is limited by the cloning capacity of the desired vector.

Optimum hybridization conditions are experimentally determined by performing test Southern blots at various wash temperatures. Hybridization is carried out at 50° C. in 4X SET, 0.1M sodium phosphate, pH 7, 0.1% Na pyrophosphate, 0.1% SDS, 1X Denhardts solution, although any low stringency hybridization condition would also be suitable (Maniatis). Wash conditions are varied from 37°–55° C., 3×30 minutes with 0.1X SET wash (15mM NaCI, 3mM Tris base, 0.2mM EDTA, 0.1% SDS, 0.1% Sodium Pyrophosphate and 0.1M Phosphate Buffer), although any standard low stringency wash conditions can also be used. The point of this part of the experiment is to hybridize the probe and wash the Southern blot at low stringency to insure some level of cross-hybridization which may even include non-specific cross-hybridization. Next, one increases the wash stringency, for example, increasing the wash temperature in 3°–5° C. increments and then monitoring the disappearance of hybridized probe as determined by a decrease in signal upon autoradiography. Initially, one expects to see many bands hybridizing to the probe at low stringency. As the wash stringency increases, weakly hybridizing sequences melt off and disappear from the autoradiograph. As wash stringency is increased, conditions are established at which only one or a few bands still hybridize to the probe. These are the conditions to be used in future experiments. As stringency increases beyond this point, all hybridization signal is lost. The goal is to determine the most stringent condition where one or a few bands per digest still hybridize to the probe before all hybridization signal is lost.

If initial probing with a large *T. litoralis* DNA polymerase gene fragment fails to give a clear pattern using any hybridization conditions, then smaller probes can be tested until a good partnership of probe size and hybridization conditions are established. Alternatively, Example XIV of the present invention shows that several fragments spanning different regions of the *T. litoralis* DNA polymerase gene (amino terminus, IVS1, IVS2 and carboxy terminus, FIGS. 15 and 16)) can be used in separate Southern blots, but tested in parallel at the same time.

Libraries are constructed with the optimum restriction digests and hybridized with the optimized probe. A parallel approach is to clone in expression vectors and directly screen with anti-*T. litoralis* sera. Either primary approach may yield active or inactive product. If no active polymerase is detected, the clone is checked for insert size and reactivity to anti-*T. litoralis* sera. If there is no reactivity to anti-*T. litoralis* sera, then the polymerase may not be expressed from its own control sequences in *E. coli* and the plasmid insert must be sequenced to operably link the new polymerase to an *E. coli* promoter and perhaps translation signals.

In the present invention, we have identified introns or intervening sequences in Pol α conserved region motifs in both *T. litoralis* and *Pyrococcus sp.* DNA polymerase genes. We therefore predict that other Archae DNA polymerase genes may have introns in conserved motifs also. If the new polymerase clone is inactive, it should be checked for the presence of intervening sequences. These introns can be identified in 2 ways. If these introns are related to introns found in *T. litoralis* and *Pyrococcus sp.* DNA polymerase genes, they can be identified by low stringency hybridization to DNA probes derived from intron sequences of *T. litoralis* and *Pyrococcus sp.* DNA polymerase genes. If IVSs are found, the clone is sequenced to develop strategies for removal of the IVS. If the clone is inactive and no cross-hybridizing IVSs are found, then the plasmid is sequenced to look for new IVSs. The archaebacterium DNA polymerase gene can be sequenced at the DNA level and the sequenced compared to (1) other DNA polymerases to identify non-similar segments (2) conserved motifs to look for the absence of Regions I–VI, followed by identification of interruption points in Regions which are absent. Once identified, introns can be removed in vitro by any number of techniques known in the art, some of which are described in this application with respect to removal of IVS1 and IVS2 from the *T. litoralis* DNA polymerase gene.

If the primary library screening fails to produce a clone synthesizing active thermostable DNA polymerase, but does result in a partial gene clone as determined by (1) cross-hybridization at the DNA level, (2) cross-reactivity at the antibody level, and (3) similarity to other DNA polymerases at the DNA sequence or deduced amino acid sequence levels, then more genomic Southern blots are probed with the initial clone to identify restriction enzymes to be selected for making the next library. The second library should contain larger fragments which are more likely to encode the entire polymerase gene. The library is screened with either antibody or preferably, the initial new polymerase cloned sequence. The resultant positives are checked for thermostable DNA polymerase activity. If no active thermostable DNA polymerase is detected in this second round, then intervening sequences can be screened for by cross-hybridization and DNA sequencing. DNA sequencing can also indicate whether the cloned gene is complete by establishing the presence of all the conserved polymerase motifs and a stop codon in the polymerase open reading frame. Several rounds of screening and rescreening may be necessary before finally cloning an active thermostable DNA polymerase.

It should also be noted that the above screening and rescreening procedure may not be sufficient for cloning the new thermostable polymerase gene because of toxic elements present in the gene. In this case, cross-reactivity at the DNA or protein level is an excellent method of cloning because only partial, inactive products can initially be cloned which will allow subsequent cloning of the complete gene. If obtaining the complete gene is not straightforward using the strategy outlined above, one should look for the presence of intervening sequences like IVS2 which are very toxic when cloned. This is accomplished by either looking for deletions and rearrangements in polymerase clones or by probing for known toxic *T. litoralis* IVS sequences. Duplicate Southern blots are probed with polymerase coding regions and IVS sequences to locate toxic IVSs in proximity to the polymerase coding region. If rearrangements or toxic IVSs are found, then the appropriate strategy would be to first operably link the amino terminal of the polymerase to a very tightly controlled expression system as described in this present application. Once accomplished, the remainder of the polymerase gene can be cloned and ligated to the amino terminus, reducing expression of toxic elements such as the *T. litoralis* IVS2 sequence. Alternatively, cross-hybridizing sub-fragments of the polymerase gene can be isolated, checked for IVSs by hybridization or DNA sequencing, IVSs can be removed in vitro from these regions by methods known in the art. The complete polymerase gene can then be constructed by ligation of sub-fragments from which toxic elements have been removed.

What is claimed is:

1. An isolated DNA which codes for a recombinant DNA polymerase from thermophilic archaebacteria, consisting essentially of a DNA fragment which hybridizes in a Southern blot to an isolated DNA fragment selected from the group consisting of a DNA fragment consisting essentially of nucleotides 1–1274 of SEQ ID NO:1, a DNA fragment consisting essentially of nucleotides 291–1772 of SEQ ID NO: 1, a DNA fragment consisting essentially of nucleotides 3387–3533 of SEQ ID NO:1, a DNA fragment consisting essentially of nucleotides 4704–5396 of SEQ ID NO: 1, and a DNA fragment consisting essentially of nucleotides 4718–5437 of SEQ ID NO:1, wherein hybridization is conduction under the following conditions:

a) hybridization: 0.75M NaCl, 0.15 Tris, 10mM EDTA, 0.1% Sodium Pyrophosphate, 0.1% SLS, 0.03% BSA, 0.03% Ficoll 400, 0.03% PVP and 100ug/ml boiled calf thymus DNA at 50° C. for about 12 hours and;

b) wash: 3×30 minutes with 0.1X SET, 0.1% SDS, 0.1% sodium pryrophosphate and 0.1M phosphate buffer at 45° C.

2. A cloning vector comprising the isolated DNA of claim 1.

3. A host cell transformed by the vector of claim 2.

4. A method for producing a recombinant thermostable DNA polymerase from archaebacteria comprising culturing a host cell transformed with the vector of claim 2 under conditions suitable for the expression of the DNA polymerase.

5. A DNA probe which hybridizes to the DNA sequence coding for the archaebacteria thermostable DNA polymerase of claim 1, wherein the DNA probe is selected from the group consisting of a DNA fragment consisting essentially of nucleotides 1-4771 of SEQ ID NO: 1, a DNA fragment consisting essentially of nucleotides 1-1274 of SEQ ID NO:1, a DNA fragment consisting essentially of nucleotides 1269-2856 of SEQ ID NO:1, and a DNA fragment consisting essentially of nucleotides 2851-4771 of SEQ ID NO: 1.

6. A method for isolating a target DNA fragment consisting essentially of a DNA coding for a thermostable DNA polymerase from thermophilic archaebacterium comprising the steps of:
   (a) forming a genomic library from the archaebacterium;
   (b) transforming or transfecting an appropriate host cell with the library of step (a);
   (c) contacting DNA from the transformed or transfected host cell with a DNA probe which hybridizes to a DNA fragment selected from the group consisting of a DNA fragment consisting essentially of nucleotides 1-1274 of SEQ ID NO:1, a DNA fragment consisting essentially of nucleotides 291-1772 of SEQ ID NO:1, a DNA fragment consisting essentially of nucleotides 3387-3533 of SEQ ID NO:1, a DNA fragment consisting essentially of nucleotides 4704-5396 of SEQ ID NO: 1, and a DNA fragment consisting essentially of nucleotides 4718-5437 of SEQ ID NO:1, wherein hybridization is conducted under the following conditions:
   a) hybridization: 0.75M NaCl, 0.15 Tris, 10mM EDTA, 0.1% Sodium Pyrophosphate, 0.1% SLS, 0.03% BSA, 0.03% Ficoll 400, 0.03% PVP and 100ug/ml boiled calf thymus DNA at 50° C. for about 12 hours and;
   b) wash: 3×30 minutes with 0.1X SET, 0. 1% SDS, 0.1% sodium pryrophosphate and 0.1M phosphate buffer at 37°-55° C.;
   (d) assaying the transformed or transfected cell of step (c) which hybridizes to the DNA probe for DNA polymerase activity;
   (e) isolating a target DNA fragment which codes for the thermostable DNA polymerase.

7. A method for isolating a DNA fragment consisting essentially of a DNA coding for a thermostable DNA polymerase from thermophilic archaebacterium comprising the steps of:
   (a) forming a genomic library from the archaebacterium;
   (b) transforming or transfecting an appropriate host cell with the library of step (a);
   (c) contacting cellular polypeptide extract from the transformed or transfected host cell with an antibody probe which has specific affinity for *T. litoralis* DNA polymerase;
   (d) assaying the transformed or transfected cell of step (c) which is cross-reactive to the antibody probe for DNA polymerase activity; and
   (e) isolating a DNA fragment which codes for the thermostable DNA polymerase.

8. A method for increasing the recombinant, heterologous expression in a host cell of a thermostable DNA polymerase from a thermophilic archaebacteria comprising the steps of:
   (a) identifying and locating an intervening nucleotide sequence of the isolated DNA of claim 1; and
   (b) removing the intervening nucleotide sequence from the isolated DNA.

9. The method of claim 8, wherein the archaebacteria comprises *T. litoralis*.

10. The method of claim 9, wherein the intervening nucleotide sequence is selected from the group of IVS1, IVS2 or IVS1 and IVS2.

11. The method of claim 8, wherein the intervening nucleotide sequence is identified and located with a DNA probe coding for an intron from the DNA sequence encoding *T. litoralis* DNA polymerase.

12. The method of claim 11, wherein the DNA probe is selected from the group consisting of a DNA fragment consisting essentially of the 1614 bp nucleotide sequence of SEQ ID NO:1 from nucleotide 1776 to nucleotide 3389, a DNA fragment consisting essentially of a portion of the 1614 bp nucleotide sequence of SEQ ID NO:1 from nucleotide 1776 to nucleotide 3389, a DNA fragment consisting essentially of 1160 bp nucleotide sequence of SEQ ID NO: 1 from nucleotide 3544 to nucleotide 4703, and a DNA fragment consisting essentially of a portion of the 1160 bp nucleotide sequence of SEQ ID NO:1 from nucleotide 3544 to nucleotide 4703.

* * * * *

UNITED STATES PATENT AND TRADEMARK OFFICE
CERTIFICATE OF CORRECTION

PATENT NO. : 5,352,778　　　　　　　　　　　　Page 1 of 11
DATED　　　 : October 4, 1994
INVENTOR(S) : Comb, et al It is certified that error appears in the above-indentified patent and that said Letters Patent is hereby corrected as shown below:

Section [57] ABSTRACT, line 1, replace "polymeraset" with --polymerases--

Section [57] ABSTRACT, line 2, replace "polymeraset" with --polymerases--

Section [57] ABSTRACT, line 4, replace "probet" with --probes--

Section [57] ABSTRACT, line 5, replace "polymerate" with --polymerase--

Section [57] ABSTRACT, line 6, replace "polymerate" with --polymerase--

Section [57] ABSTRACT, line 6, replace "meshocs" with --methods--

Section [57] ABSTRACT, line 9, replace "polymeraset" with --polymerases--

Column 2, line 38, replace "at;" with --at--

Column 2, line 51, replace "encodes-an" with --encodes an--

Column 3, line 23-24, replace "quantitatives" with --quantities--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 4, line 3, replace "}" with --)--

Column 4, line 7, replace "32P" with --$^{32}$P--

Column 4, line 9, replace "litaralis" with --litoralis--

Column 1, line 24, after "polymerases" insert --.--

Column 3, line 19, replace "coding coding" with --coding--

Column 6, line 12, replace "inocculated" with --inoculated--

Column 7, line 3, replace "DNA;" with --DNA--

Column 8, line 19, replace "for coding" with --coding--

Column 9, line 14, replace "Enzomology" with --*Enzymology*--

Column 11, line 23, replace "*Enymology*" with --*Enzymology*--

Column 13, line 53, replace "an" with --a--

Column 13, line 65, replace "The" with --the--

Column 15, ilne 25, replace "dedioxy" with --dideoxy--

Column 17, line 35, replace "b-lactoglobulin" with --ß-lactoglobulin--

UNITED STATES PATENT AND TRADEMARK OFFICE
CERTIFICATE OF CORRECTION

PATENT NO. : 5,352,778
DATED : October 4, 1994
INVENTOR(S) : Comb, et al

Page 3 of 11

It is certified that error appears in the above-indentified patent and that said Letters Patent is hereby corrected as shown below:

Column 18, line 48, replace "MgCl2" with --$MgCl_2$--

Column 20, line 138, replace "MgCl2" with --$MgCl_2$--

Column 4, line 13, replace "XDBA" with --$\lambda$DNA--

Column 4, line 67, replace "*thermococcus*" with --*Thermococcus*--

Column 5, line 1, replace "Parent" with --Percent--

Column 5, line 15, replace "*litoratis*" with --*litoralis*--

Column 6, line 52, replace "ONA" with --DNA--

Column 8, line 52, replace "thermococcus" with --Thermococcus--

Column 9, line 3, replace "¢0166" with --40166--

Column 9, line 20, replace "*Experimentel*" with --*Experimental*--

Column 10, line 6, replace "sere" with --sera--

Column 10, line 14, replace "polymerasa" with --polymerase--

UNITED STATES PATENT AND TRADEMARK OFFICE
CERTIFICATE OF CORRECTION

PATENT NO. : 5,352,778
DATED : October 4, 1994
INVENTOR(S) : Comb, et al

Page 4 of 11

It is certified that error appears in the above-indentified patent and that said Letters Patent is hereby corrected as shown below:

Column 10, line 16, replace "MI3" with --M13--

Column 10, line 21, replace "Encodino" with --Encoding--

Column 10, line 25, replace "*litoralis* Ils" with --*litoralis*--

Column 10, line 46, replace "Becillus subtills" with --*Bacillus subtilis*--

Column 10, line 49, replace "*tumefeciens*" with --*tumefaciens*--

Column 11, line 58, replace "*Aced*" with --*Acad*--

Column 12, line 19, replace "Maniatie" with --Maniatis--

Column 13, line 3, replace "el uted" with --eluted--

Column 13, line 3, replace "l i near" with --linear--

Column 13, line 4, replace "0.I M" with --0.1 M--

Column 13, line 8, replace "I5" with --15--

Column 13, line 35, replace "gone" with --gene--

Column 13, line 55, replace "gone" with --gene--

Column 14, line 38, replace "oligomerso" with --oligomers.--

UNITED STATES PATENT AND TRADEMARK OFFICE
CERTIFICATE OF CORRECTION

PATENT NO. : 5,352,778                    Page 5 of 11
DATED      : October 4, 1994
INVENTOR(S): Comb, et al It is certified that error appears in the above-indentified patent and that said Letters Patent is hereby corrected as shown below:

Column 16, line 2, replace "Thermoccoccus" with --Thermococcus--

Column 17, line 5, replace "100/µg/ml" with --100 µg/ml--

Column 18, line 1, replace "0.05Tri ton-X" with
    --0.05% Triton-X--

Column 18, line 32, replace "MgCl2" with --MgCl$_2$--

Column 18, line 47, replace "I" with --1--
Column 19, line 11, replace "beta-gal actosidase" with
    --beta galactosidase--

Column 19, line 35, replace "ONA" with --DNA--

Column 20, line 15, replace "g U SpeI" with --9 U SpeI--

Column 20, line 22, replace "Bali" with --BalI--

Column 20, line 34, replace "Bali" with --BalI--

Column 20, line 34, replace "HinctI" with --HincII--

Column 22, line 26, replace "F-co" with --Eco--

Column 22, line 27, replace "F-co" with --Eco--

Column 22, line 58, replace "Screen" with --Screening--

Column 23, line 4, replace "55" with --65--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 24, line 16, replace "Ash" with --Asn--

Column 24, line 19, replace "Ash" with --Asn--

Column 24, line 66, replace "Junction" with --junction--

Column 25, line 31, replace "181" with --1B1--

Column 25, line 33, replace "181" with --1B1--

Column 26, line 6, replace "t. Litoralis" with --T. Litoralis--

Column 26, line 9-10, replace "try-prone" with --tryptone--

Column 20, line 19, replace "HapI" with --HpaI--

Column 24, lines 45-46, replace "Enzomology" with --Enzymology--

Column 25, lines 9-10, replace "Enzomology" with --Enzymology--

Column 26, line 41, replace "ph" with --pH--

Column 28, line 39, replace "Enymology" with --Enzymology--

Column 29, line 9, replace "Enzomology" with --Enzymology--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 29, line 28, replace "Tris-Hcl" with --Tris-HCl--

Column 34, line 27, replace "than the" with --than that--

Column 35, line 21, replace "Commasie" with --Coomasie--

Column 38, line 2, replace "KPO4" with --KP0$_4$--

Column 38, line 43, replace "b-lactoglobulin" with
    --ß-lactoglobulin--

Column 40, line 25, replace "*Mathmatics*" with
    --*Mathematics*--

Column 40, line 53, replace "thermophyllic" with
    --thermophilic--

Column 26, line 11, replace "rag" with --mg--

Column 26, line 20, replace "Gaul in" with --Gaulin--

Column 26, line 39, replace "5" with --75--

Column 29, line 28, replace "pHB.8" with --pH8.8--

Column 29, line 31, replace "//" with --/--

Column 30, line 56, replace "ARB" with --*Annual Review of
    Biochemistry*--

Column 33, ** note in table, replace "dctp" with
    --dCTP--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 33, line 33, replace "Hpat" with --HpaI--

Column 33, line 62, replace "3' and" with --3' (SEQ ID NO:6) and--

Column 33, line 64, replace "3')" with --3' (SEQ ID NO:7))--

Column 34, line 21, replace "quantirate" with --quantitate--

Column 35, line 3, replace "1.0 MgSO4" with --10 MgSO$_4$--

Column 35, line 15, replace "0.1M" with --0.1 M--

Column 35, line 52, replace "I-Tli" with --exon2/exon3 junction also refered to as the I-Tli--

Column 35, line 54, replace "50ram" with --50mM--

Column 36, line 12, replace "polymeras" with --polymerase--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 36, line 56, replace "alumen" with --albumin--

Column 36, line 58, replace "pV174.181" with --pV174-1B1--
Column 36, line 58-59, replace "0.01A26-0U/ml" with --0.01 $A_{260}$U/ml--

Column 37, line 4, replace "dH20" with --$dH_2O$"

Column 37, line 10, replace "Scai" with --ScaI--

Column 37, line 15, replace "pV174.181" with --pV174.1B1--

Column 38, line 14, replace "I liter" with --1 liter--

Figures 13A, 13B:
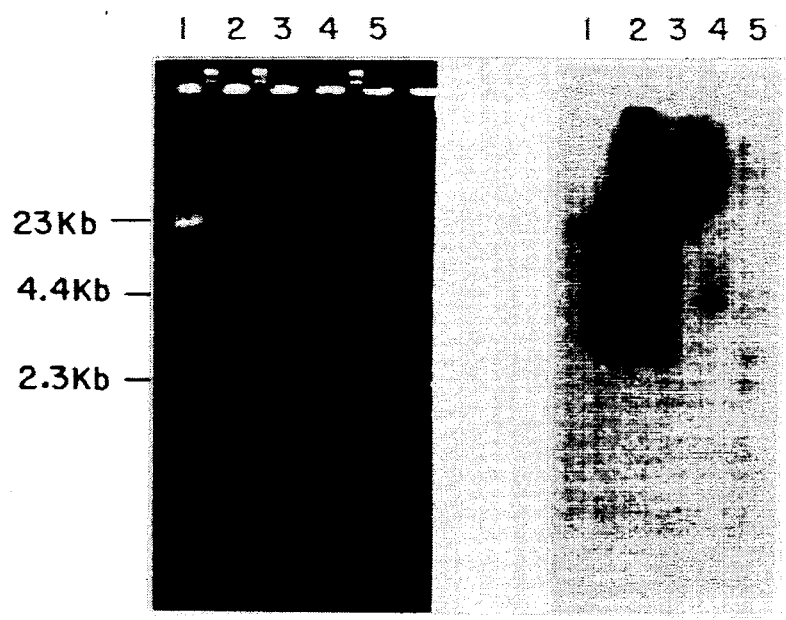
FIG. 13A is the ethidium bromide stained agarose gel of *Pyrococcus* sp. DNA cut with EcoR I (lane 3 ), BamH I (lane 4) and Hind III (lane 5}. Lane 1 is λDNA cut with Hind III as markers and lane 2 is pBR322 as a marker.
FIG. 13B is an autoradiography of a Southern hybridization of the same gel in FIG. 13A. The 32P-DNA probe was prepared from a 1.3 Kb Eco RI fragment that encodes the amino terminal portion of the *T. litaralis* DNA polymerase. Note that the BamH I cut Pyrococcus sp. DNA gives a single band of about 4–5 Kb with the probe. The fact that the 23 Kd band of Hind III cut XDNA shows up on the film is due to nonspecific hybridization to the large amount of DNA present in that band. The fact that the plasmid pBR322 lights up is due to homologous sequences in the probe.

Column 38, line 61, replace "FIG.138" with --FIG. 13B--

Column 39, line 6, replace "pH 1" with --pH 7--

Column 39, line 37, replace "supre" with --supra--

Column 39, line 50, replace "Bg" with --B9--

Column 40, lines 56-58, delete "from a Balanced Deoxynucleotide State to an Unbalanced State"

Column 41, line 11, replace "0.SM" with --0.5M--

Column 41, line 17, replace "IBX" with --18X--

Column 42, line 5, replace "GB-O" with --GB-D--

Column 42, line 37, replace "0,002%" with --0.002%--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 43, line 1, replace "temperature," with --temperature.--

Column 43, line 2, replace "filers" with --filters--

Column 43, line 8, replace "Peromega" with --Promega--

Column 43, line 10, replace "Prococcus" with --Pyrococcus--

Column 43, line 13, replace "anit" with --anti--

Column 43, line 20, replace "monoclonal" with --Monoclonal--

Column 43, line 21, delete "pi"

Column 43, line 25, replace "anit" with --anti--

Column 43, line 27, replace "he" with --the--

Column 43, line 33, replace "pPyrococcus" with --Pyrococcus--

Column 43, line 36, replace "Identifies" with --Identities--

Column 44, line 42, replace "NaCI" with --NaCl--

Column 47, line 31, replace "NaCI" with --NaCl--

UNITED STATES PATENT AND TRADEMARK OFFICE
CERTIFICATE OF CORRECTION

PATENT NO. : 5,352,778
DATED : October 4, 1994
INVENTOR(S) : Comb, et al

It is certified that error appears in the above-indentified patent and that said Letters Patent is hereby corrected as shown below:

Column 41, line 56, replace "hybridation" with
    --hybridization--

Column 42, lines 64-65, replace "Methods86:217-233"
    with --Methods 86:217-233--

Column 46, line 50, replace "conduction" with
    --conducted--

Column 46, line 57, replace "pryrophosphate" with
    --pyrophosphate--

Signed and Sealed this

Sixth Day of August, 1996

Attest:

BRUCE LEHMAN

Attesting Officer    Commissioner of Patents and Trademarks